(12) United States Patent
Karin et al.

(10) Patent No.: US 6,706,509 B2
(45) Date of Patent: *Mar. 16, 2004

(54) ONCOPROTEIN PROTEIN KINASE

(75) Inventors: Michael Karin, La Jolla, CA (US); Masahiko Hibi, Hyogo (JP); Anning Lin, Chicago, IL (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/861,012

(22) Filed: May 18, 2001

(65) Prior Publication Data

US 2003/0190735 A1 Oct. 9, 2003

Related U.S. Application Data

(63) Continuation of application No. 09/461,649, filed on Dec. 14, 1999, now Pat. No. 6,342,595, which is a continuation of application No. 09/150,201, filed on Sep. 8, 1998, now Pat. No. 6,004,584, which is a division of application No. 08/799,913, filed on Feb. 19, 1997, now Pat. No. 5,804,399, which is a continuation of application No. 08/111,393, filed on May 19, 1995, now Pat. No. 5,605,808, which is a division of application No. 08/276,860, filed on Jul. 18, 1994, now Pat. No. 5,593,884, which is a continuation of application No. 08/220,602, filed on Mar. 25, 1994, now Pat. No. 6,514,745, which is a continuation-in-part of application No. 08/094,533, filed on Jul. 19, 1993, now Pat. No. 5,534,426.

(51) Int. Cl.$^7$ .............................. C12N 9/12; C12N 15/54

(52) U.S. Cl. ................ 435/194; 435/252.3; 435/320.1; 536/23.2

(58) Field of Search .......................... 435/320.1, 252.3, 435/194; 536/23.2

(56) References Cited

U.S. PATENT DOCUMENTS

| | | | |
|---|---|---|---|
| 5,534,426 A | 7/1996 | Karin et al. | 435/194 |
| 5,593,884 A | 1/1997 | Karin et al. | 435/252.3 |
| 5,605,808 A | 2/1997 | Karin et al. | 435/15 |
| 5,804,399 A | 9/1998 | Karin et al. | 435/15 |
| 5,837,244 A | 11/1998 | Karin et al. | 424/139.1 |
| 5,994,513 A | 11/1999 | Karin et al. | 530/387.9 |
| 6,001,584 A | 12/1999 | Karin et al. | 435/15 |
| 6,193,965 B1 | 2/2001 | Karin et al. | 424/131.1 |
| 6,342,595 B1 | 1/2002 | Karin et al. | 536/23.5 |
| 6,514,745 B1 | 2/2003 | Karin et al. | 435/252.3 |

FOREIGN PATENT DOCUMENTS

| | | |
|---|---|---|
| AU | 685484 | 2/1995 |
| AU | 700137 | 2/1995 |
| EP | 0 599 077 | 6/1994 |
| JP | 2925740 | 5/1999 |
| JP | 2986548 | 10/1999 |

OTHER PUBLICATIONS

Adler et al. Affinity purified c Jun amino terminal protein kinase requires serine/threonine phosphorylation for activity. J Biol Chem. Aug. 25, 1992;267(24):17001 5.

Pulverer et al. Co purification of mitogen activated protein kinases with phorbol ester induced c Jun kinase activity in U937 leukaemic cells. Oncogene. Feb. 1993;8(2):407 15.

Allegretto DNA binding activity of Jun is increased through its interaction with Fos. J Cell Biochem. Apr. 1990;42(4):193 206.

Bohmann et al. Human proto–oncogene c–jun encodes a DNA binding protein with structural and functional properties of transcription factor AP–1. Science. Dec. 4, 1987;238(4832):1386–92. Review.

Adler et al., "Phorbol Esters Stimulate the Phosphorylation of c–Jun But Not v–Jun: Regulation by the N–terminal δ Domain," *Proc. Natl. Acad. Sci. USA*, 89:5341–5345 (1992).

Anderson et al., "Requirement for Integration of Signals from Two Distinct Phosphorylation Pathways for Activation of MAP Kinase," *Nature*, 343:651–653 (1990).

Boulton et al., "ERKs: A Family of Protein–Serine/Threonine Kinases that are Activated and Tyrosine Phosphorylated in Response to Insulin and NGF" *Cell*, 65:663–675 (1991).

Boulton et al., "An Insulin–Stimulated Protein Kinase Similar to Yeast Kinases Involved in Cell Cycle Control," *Science*, 249:64–67 (1990).

Cano and Mahadevan, "Parallel Signal Processing Among Mammalian MAPKs," *TIBS*, 20:117–122 (1995).

Derijard et al., "JNK1: A Protein Kinase Stimulated by UV Light and Ha–Ras that Binds and Phosphorylates the c–Jun Activation Domain," *Cell*, 76:1–20, (1994).

Hattori et al., *Proc. Natl. Acad. Sci. USA*, 85:9148–9152 (1988).

Hibi et al., "Identification of an Oncoprotein– and UV–Responsive Protein Kinase that Binds and Potentiates the c–Jun Activation Domain," *Genes and Development*, 7:2135–2148 (1993).

Kyriakis et al., "pp 54 Microtubule–Associated Protein 2 Kinase," *The Journal of Biological Chemistry*, 265(28):17355–17363 (1990).

Lamph et al., *Nature*, 334:629–631 (1988).

Lee et al., *Science*, 239:1288–1290 (1988).

Minden et al., "c–Jun N–Terminal Phosphorylation Correlates with Activation of the JNK Subgroup but Not the ERK Subgroup of Mitogen–Activated Protein Kinases," *Molecular and Cellular Biology*, 14(10):6683–6688 (1994).

(List continued on next page.)

Primary Examiner—Charles L. Patterson, Jr.

(74) Attorney, Agent, or Firm—Gray Cary Ware & Freidenrich, LLP; Lisa A. Haile; Richard J. Imbra

(57) ABSTRACT

An isolated polypeptide (JNK) characterized by having a molecular weight of 46 kD as determined by reducing SDS-PAGE, having serine and threonine kinase activity, phosphorylating the c-Jun N-terminal activation domain and polynucleotide sequences and method of detection of JNK are provided herein. JNK phosphorylates c-Jun N-terminal activation domain which affects gene expression from AP-1 sites.

27 Claims, 48 Drawing Sheets

OTHER PUBLICATIONS

Pulverer et al., "Phosphorylation of c–Jun Mediated by MAP Kinases," *Nature*, 353:670–674, (1991).

Ryder et al., *Proc. Natl. Acad. Sci. USA*, 85:8464–8467 (1988).

Ryseck et al., *Nature* 334:535–537 (1988).

Segel, *Biochemical Calculations*, p. 246, John Wiley & Sons, Inc. (1976).

Suggs et al., *Proc. Natl. Acad. Sci. USA*, 78(11):6613–6617 (1981).

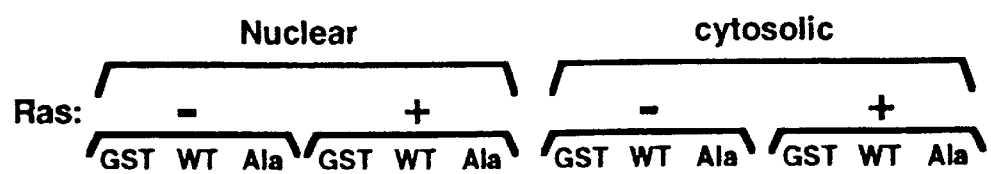
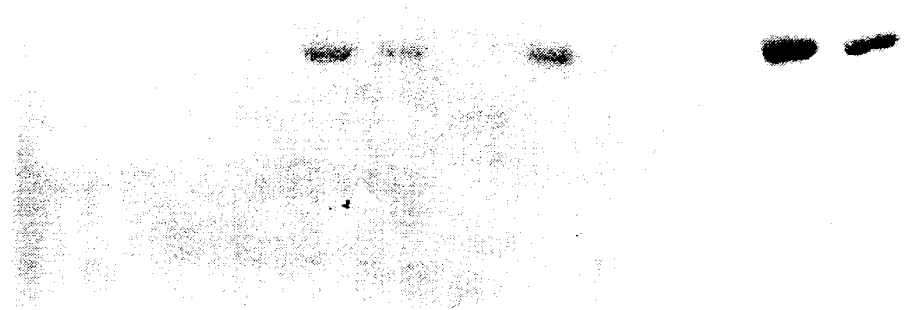
FIG. 1

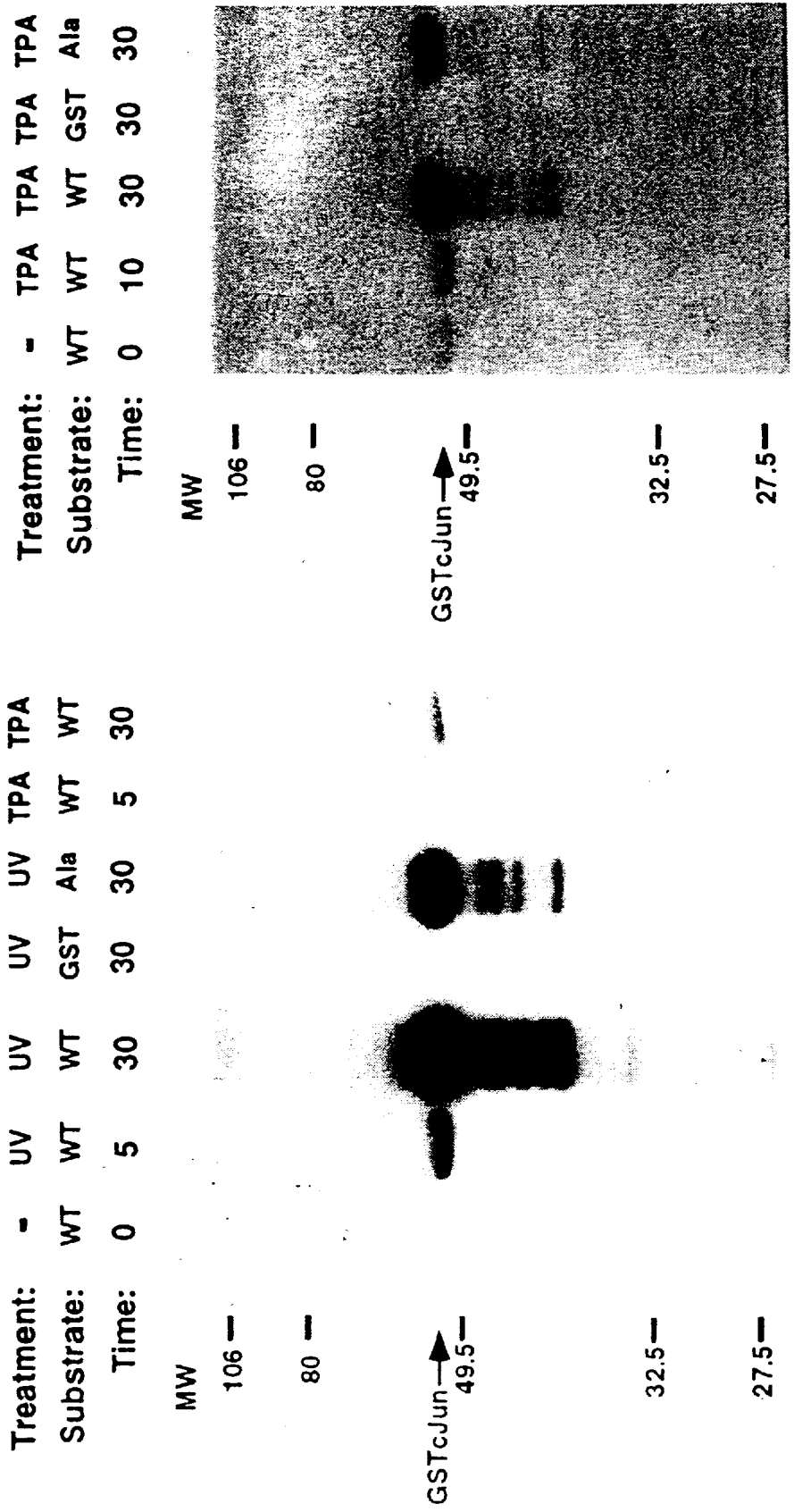

Protein Gel

32P-Immobilized Substrate

32P-Exogenous Substrate

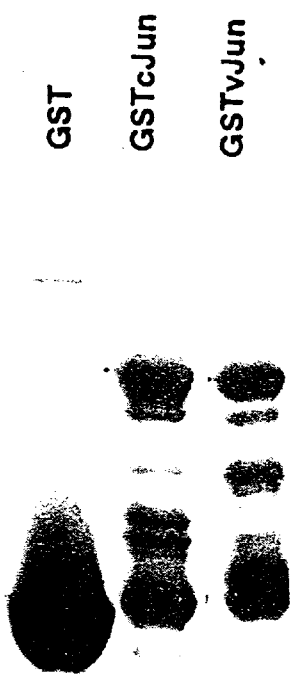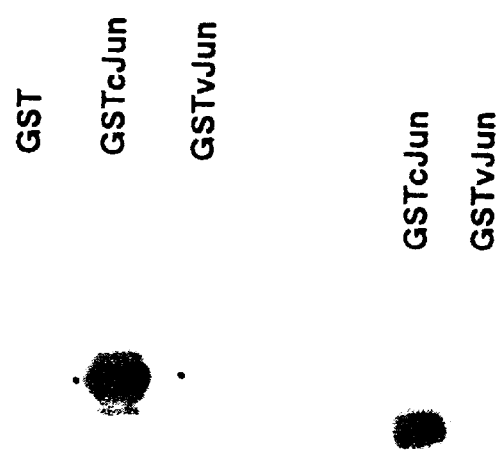
FIG. 7A　　FIG. 7B　　FIG. 7C

```
gaattccggg gcggccaaga cccgccgccg gccggccact gcagggtccg cactgatccg      60
ctccggcgga gagccgctgc tctgggaagt cagttcgcct gcggactccg aggaaccgct     120
gcgcacgaag agccgtcagt gagtgaccgc gactttcaa agccgggtag ggcgcgcgag      180
tcgacaagta agagtgcggg aggcatctta attaaccctg cgctccctgg agcagctggt    240
gaggagggcg cacggggacg acagccagcg ggtgcgtgcg ctcttagaga aactttccct    300
gtcaaaggct ccgggggggcg cgggtgtccc ccgcttgcca cagcccctgtt gcggccccga    360
aacttgtgcg cgcacgccaa actaacctca cgtgaagtga cggactgttc t atg act    417
                                                          Met Thr
                                                            1 gca aag atg gaa acg acc ttc tat gac gat gcc ctc aac gcc tcg ttc      465
Ala Lys Met Glu Thr Thr Phe Tyr Asp Asp Ala Leu Asn Ala Ser Phe
  5                  10                  15 ctc ccg tcc gag agc gga cct tat ggc tac agt aac ccc aag atc ctg      513
Leu Pro Ser Glu Ser Gly Pro Tyr Gly Tyr Ser Asn Pro Lys Ile Leu
 20                  25                  30 aaa cag agc atg acc ctg aac ctg gcc gac cca gtg ggg agc ctg aag      561
Lys Gln Ser Met Thr Leu Asn Leu Ala Asp Pro Val Gly Ser Leu Lys
 35                  40                  45                  50
```

FIG. 10A

| | | | | | | | | |
|---|---|---|---|---|---|---|---|---|
| ccg | cac | ctc | cgc | gcc | aag | aac | tcg | gac | gtg |
| Pro | His | Leu | Arg | Ala | Lys | Asn | Ser | Asp | Val |
| | | | 55 | | | 60 | | 65 | |
| | | | | | | | | | 609 | ccg cac ctc cgc gcc aag aac tcg gac ctc acc tcg ccc gac gtg   609
Pro His Leu Arg Ala Lys Asn Ser Asp Leu Thr Ser Pro Asp Val
                    55              60              65 ggg ctg ctc aag ctg gcg tcg ccc gag ctg cgc ctg ata atc cag   657
Gly Leu Leu Lys Leu Ala Ser Pro Glu Leu Arg Leu Ile Ile Gln
                    70              75                  80 tcc agc aac ggg cac atc acc acc acg ccc acc cag ttc ctg       705
Ser Ser Asn Gly His Ile Thr Thr Thr Pro Thr Gln Phe Leu
            85              90              95 tgc ccc aag aac gtg aca gat gag cag gag ggg ttc gcc gag ggc ttc   753
Cys Pro Lys Asn Val Thr Asp Glu Gln Glu Gly Phe Ala Glu Gly Phe
            100             105             110 gtg cgc ggc gcg ctg gcc gaa ctg cac ctg agc cag aac acg ctg gtc   801
Val Arg Gly Ala Leu Ala Glu Leu His Leu Ser Gln Asn Thr Leu Val
            115             120             125             130 acg tcg gcg gcg cag ccg gtc aac ggg gca ggc atg gtg gct ccc gcg   849
Thr Ser Ala Ala Gln Pro Val Asn Gly Ala Gly Met Val Ala Pro Ala
            135             140             145 gta gcc tcg gtg gca ggg ggc agc agc ggc ggc ggc ttc agc gcc agc   897
Val Ala Ser Val Ala Gly Gly Ser Ser Gly Gly Gly Phe Ser Ala Ser
            150             155             160

FIG. 10B

```
ctg cac agc gag ccg ccg gtc tac gca aac ctc agc aac ttc aac cca      945
Leu His Ser Glu Pro Pro Val Tyr Ala Asn Leu Ser Asn Phe Asn Pro
165                 170                 175 ggc gcg ctg agc agc ggg ggc ggc gcg ccc tcc tac ggc gcg gcc ggc      993
Gly Ala Leu Ser Ser Gly Gly Gly Ala Pro Ser Tyr Gly Ala Ala Gly
180                 185                 190 ctg gcc ttt ccc gcg caa cag cag cag cag cag cag ccg cac cac         1041
Leu Ala Phe Pro Ala Gln Gln Gln Gln Gln Gln Gln Pro His His
195                 200                 205                 210 ctg ccc cag cag atg ccc gag gtg cag cac ccg cgg ctg cag gcc aag     1089
Leu Pro Gln Gln Met Pro Glu Val Gln His Pro Arg Leu Gln Ala Lys
215                 220                 225 gag gag cct cag aca gtg acc ggc atg ccc ggc gag aca ccc ccc ctg     1137
Glu Glu Pro Gln Thr Val Thr Gly Met Pro Gly Glu Thr Pro Pro Leu
230                 235                 240 tcc ccc atc gac atg gag tcc cag gag cgg atc aag gcg gag agg aag     1185
Ser Pro Ile Asp Met Glu Ser Gln Glu Arg Ile Lys Ala Glu Arg Lys
245                 250                 255 cgc atg agg aac cgc atc gct gcc tcc aag tgc cga aaa agg aag ctg     1233
Arg Met Arg Asn Arg Ile Ala Ala Ser Lys Cys Arg Lys Arg Lys Leu
260                 265                 270
```

FIG. 10C

```
gag aga atc gcc cgg ctg gag gaa aaa gtg aaa acc ttg aaa gct cag    1281
Glu Arg Ile Ala Arg Leu Glu Glu Lys Val Lys Thr Leu Lys Ala Gln
275                 280                 285                 290 aac tcg gag ctg gcg tcc acg gcc aac atg ctc agg gaa cag gtg gca    1329
Asn Ser Glu Leu Ala Ser Thr Ala Asn Met Leu Arg Glu Gln Val Ala
            295                 300                 305 cag ctt aaa cag aaa gtc atg aac cac gtt aac agt ggg tgc caa ctc    1377
Gln Leu Lys Gln Lys Val Met Asn His Val Asn Ser Gly Cys Gln Leu
310                 315                 320 atg cta acg cag cag ttg caa aca ttt tgaagagaga ccgtcggggg          1424
Met Leu Thr Gln Gln Leu Gln Thr Phe
325                 330 ctgaggggca acgaagaaaa aaaataacac agagagacag acttgagaac ttgacaagtt  1484
gcgacggaga gaaaaaagaa gtgtccgaga actaaagcca agggtatcca agttggactg  1544
ggttcggtct gacgcgcccc ccagtgtgca cgagtgggaa ggacctggtc gcgcccctcc  1604
ttggcgtgga gccagggagc ggccgcctgc gggctgcccc gctttgcgga cgggctgtcc  1664
ccgcgcgaac ggaacgttgg actttcgtta acattgacca agaactgcat ggacctaaca  1724
```

FIG. 10D

```
ttcgatctca ttcagtatta aaggggggcag ggggaggggg ttacaaactg caatagagac  1784
tgtagattgc ttctgtagta ctccttaaga acacaaagcg ggggagggt tggggagggg  1844
cggcaggagg gaggtttgtg agagcgaggc tgagcctaca gatgaactct ttctggcctg  1904
ctttcgttaa ctgtgtatgt acatatatat atttttaat ttgattaaag ctgattactg  1964
tcaataaaca gcttcatgcc tttgtaagtt atttccttgtt tgtttgtttg ggatcctgcc  2024
cagtgttgtt tgtaaataag agatttggag cactctgagt ttaccatttg taataaagta  2084
tataattttt tt                                                      2096
```

FIG. 10E

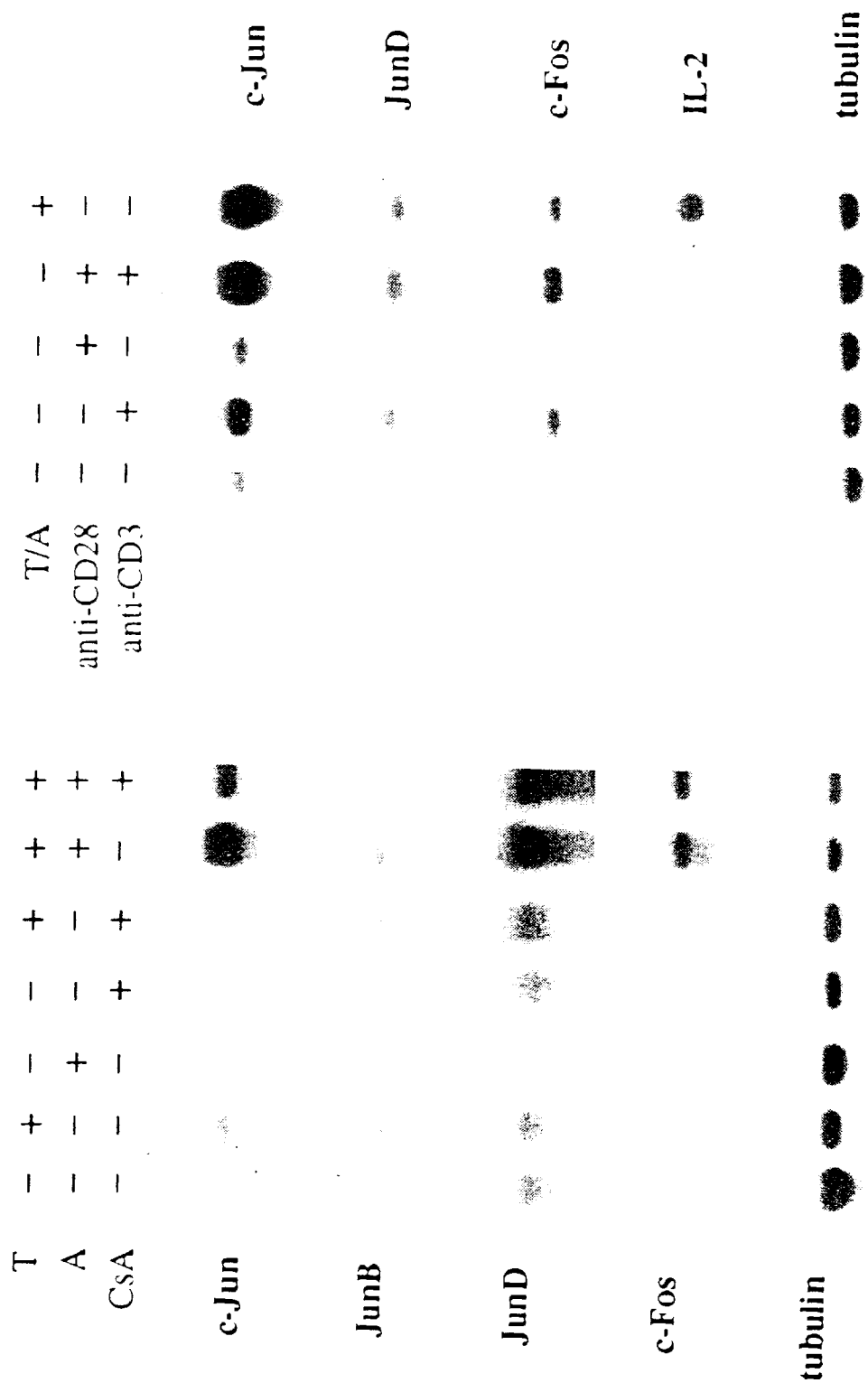

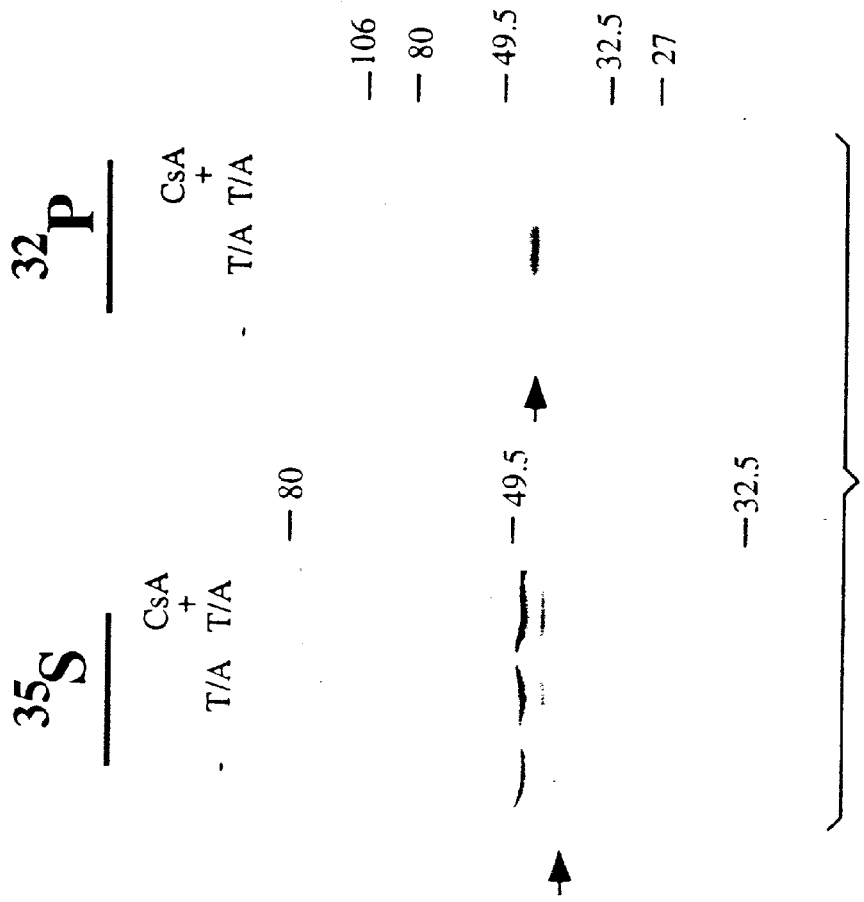
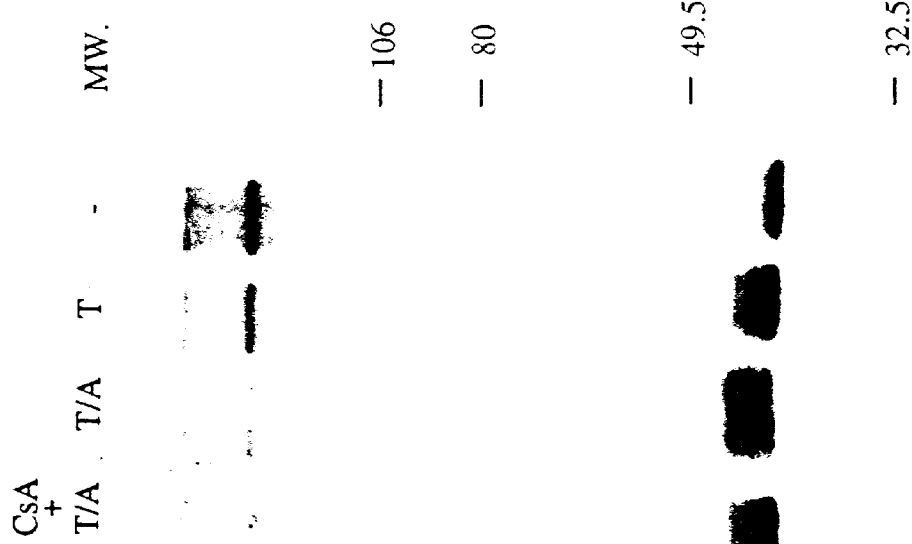
FIG.12A
FIG.12B

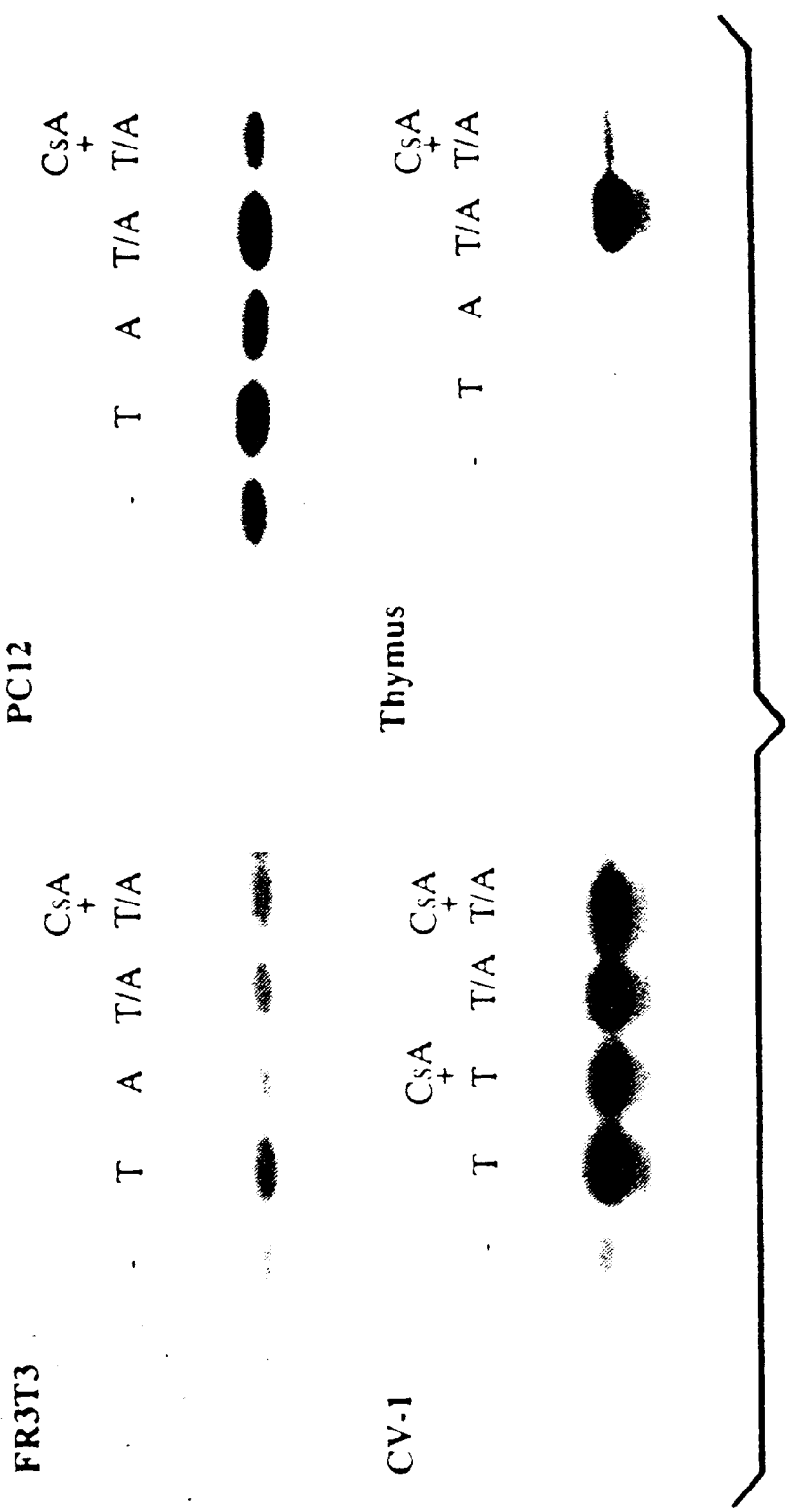

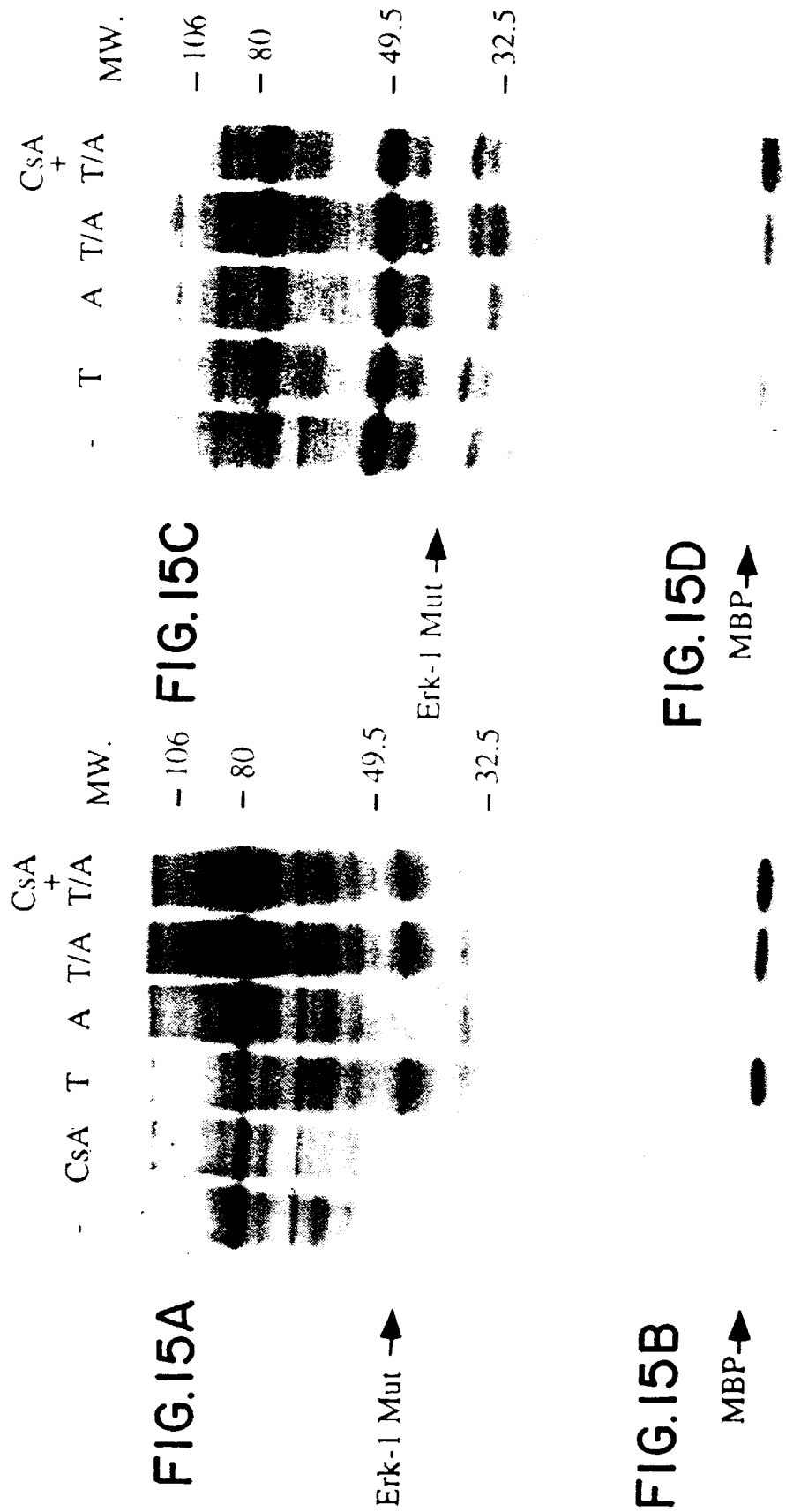

```
CATTAATTGC TTGCCATC ATG AGC AGA AGC AAG CGT GAC AAC AAT TTT TAT      51
                    Met Ser Arg Ser Lys Arg Asp Asn Asn Phe Tyr
                     1           5                      10
AGT GTA GAG ATT GGA GAT TCT ACA TTC ACA GTC CTG AAA CGA TAT CAG      99
Ser Val Glu Ile Gly Asp Ser Thr Phe Thr Val Leu Lys Arg Tyr Gln
            15              20                  25
AAT TTA AAA CCT ATA GGC TCA GGA GCT CAA GGA ATA GTA TGC GCA GCT     147
Asn Leu Lys Pro Ile Gly Ser Gly Ala Gln Gly Ile Val Cys Ala Ala
            30              35                  40
TAT GAT GCC ATT CTT GAA AGA AAT GTT GCA ATC AAG AAG CTA AGC CGA     195
Tyr Asp Ala Ile Leu Glu Arg Asn Val Ala Ile Lys Lys Leu Ser Arg
            45              50                  55
CCA TTT CAG AAT CAG ACT CAT GCC AAG CGG GCC TAC AGA GAG CTA GTT     243
Pro Phe Gln Asn Gln Thr His Ala Lys Arg Ala Tyr Arg Glu Leu Val
 60             65              70                  75
CTT ATG AAA TGT GTT AAT CAC AAA AAT ATA ATT GGC CTT TTG AAT GTT     291
Leu Met Lys Cys Val Asn His Lys Asn Ile Ile Gly Leu Leu Asn Val
                80              85                  90
TTC ACA CCA CAG AAA TCC CTA GAA GAA TTT CAA GAT GTT TAC ATA GTC     339
Phe Thr Pro Gln Lys Ser Leu Glu Glu Phe Gln Asp Val Tyr Ile Val
            95              100                 105
ATG GAG CTC ATG GAT GCA AAT CTT TGC CAA GTG ATT CAG ATG GAG CTA     387
Met Glu Leu Met Asp Ala Asn Leu Cys Gln Val Ile Gln Met Glu Leu
            110             115                 120
GAT CAT GAA AGA ATG TCC TAC CTT CTC TAT CAG ATG CTG TGT GGA ATC     435
Asp His Glu Arg Met Ser Tyr Leu Leu Tyr Gln Met Leu Cys Gly Ile
    125             130                 135
AAG CAC CTT CAT TCT GCT GGA ATT ATT CAT CGG GAC TTA AAG CCC AGT     483
Lys His Leu His Ser Ala Gly Ile Ile His Arg Asp Leu Lys Pro Ser
140             145                 150                 155
AAT ATA GTA GTA AAA TCT GAT TGC ACT TTG AAG ATT CTT GAC TTC GGT     531
Asn Ile Val Val Lys Ser Asp Cys Thr Leu Lys Ile Leu Asp Phe Gly
            160                 165                 170
CTG GCC AGG ACT GCA GGA ACG AGT TTT ATG ATG ACG CCT TAT GTA GTG     579
Leu Ala Arg Thr Ala Gly Thr Ser Phe Met Met Thr Pro Tyr Val Val
            175             180                 185
ACT CGC TAC TAE AGA GCA CCC GAG GTC ATC CTT GGC ATG GGC TAC AAG     627
Thr Arg Tyr Tyr Arg Ala Pro Glu Val Ile Leu Gly Met Gly Tyr Lys
            190             195                 200
GAA AAC GTG GAT TTA TGG TCT GTG GGG TGC ATT ATG GGA GAA ATG GTT     675
Glu Asn Val Asp Leu Trp Ser Val Gly Cys Ile Met Gly Glu Met Val
 205                210                 215
```

FIG. 18D

```
TGC CAC AAA ATC CTC TTT CCA GGA AGG GAC TAT ATT GAT CAG TGG AAT    723
Cys His Lys Ile Leu Phe Pro Gly Arg Asp Tyr Ile Asp Gln Trp Asn
220             225             230             235
AAA GTT ATT GAA CAG CTT GGA ACA CCA TGT CCT GAA TTC ATG AAG AAA    771
Lys Val Ile Glu Gln Leu Gly Thr Pro Cys Pro Glu Phe Met Lys Lys
            240             245             250
CTG CAA CCA ACA GTA AGG ACT TAC GTT GAA AAC AGA CCT AAA TAT GCT    819
Leu Gln Pro Thr Val Arg Thr Tyr Val Glu Asn Arg Pro Lys Tyr Ala
            255             260             265
GGA TAT AGC TTT GAG AAA CTC TTC CCT GAT GTC CTT TTC CCA GCT GAC    867
Gly Tyr Ser Phe Glu Lys Leu Phe Pro Asp Val Leu Phe Pro Ala Asp
            270             275             280
TCA GAA CAC AAC AAA CTT AAA GCC AGT CAG GCA AGG GAT TTG TTA TCC    915
Ser Glu His Asn Lys Leu Lys Ala Ser Gln Ala Arg Asp Leu Leu Ser
285             290             295
AAA ATG CTG GTA ATA GAT GCA TCT AAA AGG ATC TCT GTA GAT GAA GCT    963
Lys Met Leu Val Ile Asp Ala Ser Lys Arg Ile Ser Val Asp Glu Ala
300             305             310             315
CTC CAA CAC CCG TAC ATC AAT GTC TGG TAT GAT CCT TCT GAA GCA GAA   1011
Leu Gln His Pro Tyr Ile Asn Val Trp Tyr Asp Pro Ser Glu Ala Glu
            320             325             330
GCT CCA CCA CCA AAG ATC CCT GAC AAG CAG TTA GAT GAA AGG GAA CAC   1059
Ala Pro Pro Pro Lys Ile Pro Asp Lys Gln Leu Asp Glu Arg Glu His
            335             340             345
ACA ATA GAA GAG TGG AAA GAA TTG ATA TAT AAG GAA GTT ATG GAC TTG   1107
Thr Ile Glu Glu Trp Lys Glu Leu Ile Tyr Lys Glu Val Met Asp Leu
            350             355             360
GAG GAG AGA ACC AAG AAT GGA GTT ATA CGG GGG CAG CCC TCT CCT TTA   1155
Glu Glu Arg Thr Lys Asn Gly Val Ile Arg Gly Gln Pro Ser Pro Leu
365             370             375
GCA CAG GTG CAG CAG TGATCAATGG CTCTCAGCAT CCATCATCAT CGTCGTCTGT   1210
Ala Gln Val Gln Gln
380

CAATGATGTG TCTTCAATGT CAACAGATCC GACTTTGGCC TCTGATACAG ACAGCAGTCT 1270

AGAAGCAGCA GCTGGGCCTC TGGGCTGCTG TAGATGACTA CTTGGGCCAT CGGGGGGTGG 1330

GAGGGATGGG GAGTCGGTTA GTCATTGATA GAACTACTTT GAAAACAATT CAGTGGTCTT 1390

ATTTTTGGGT GATTTTTCAA AAAATGTA                                   1418
```

FIG. 18E

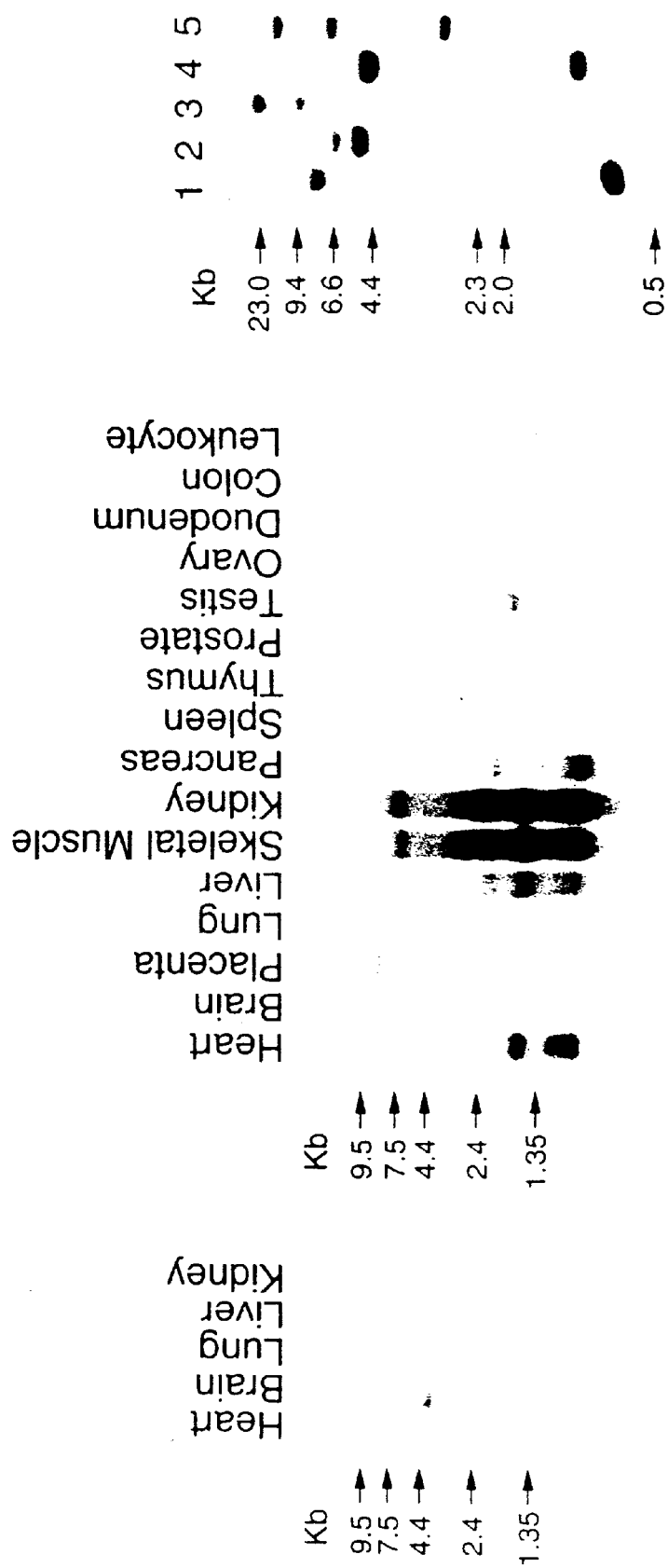

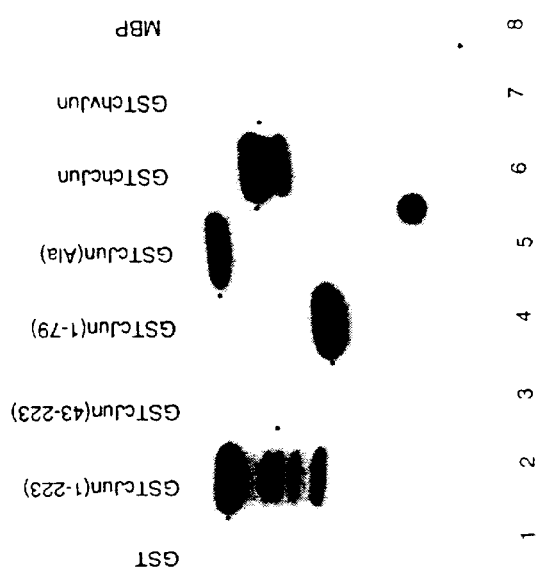
FIG. 23A
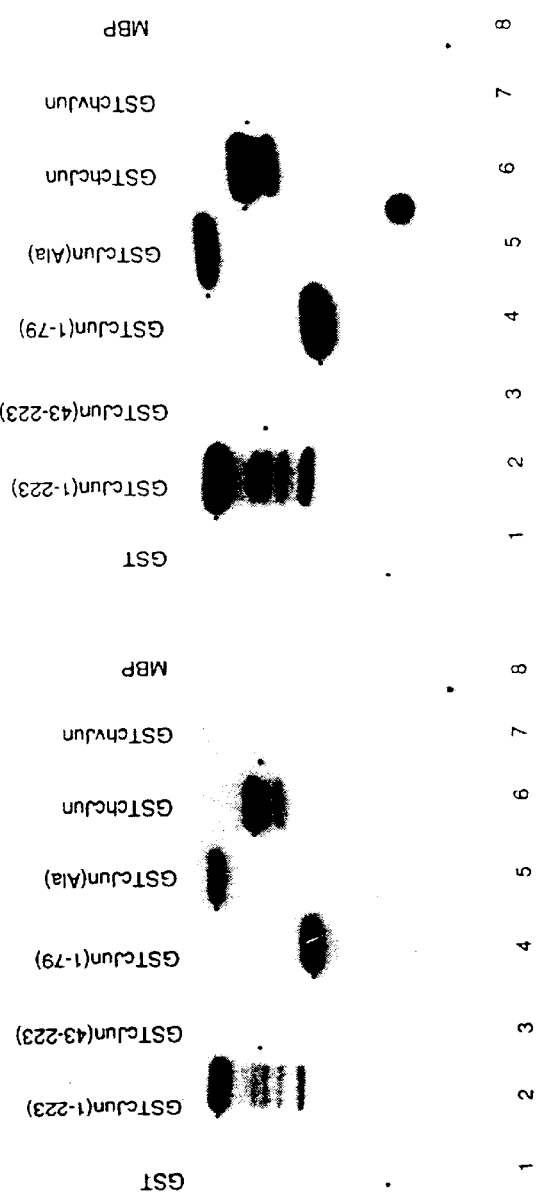
FIG. 23B
FIG. 23C
FIG. 23D

FIG. 24A  FIG. 24B  FIG. 24C

GSTcJun(1-223)    GSTcJun(1-223/Ala-63,73)    GSTcJun(1-79)

c-Jun
+JNK1 c-Jun
+JNK46

FIG. 24D    FIG. 24E

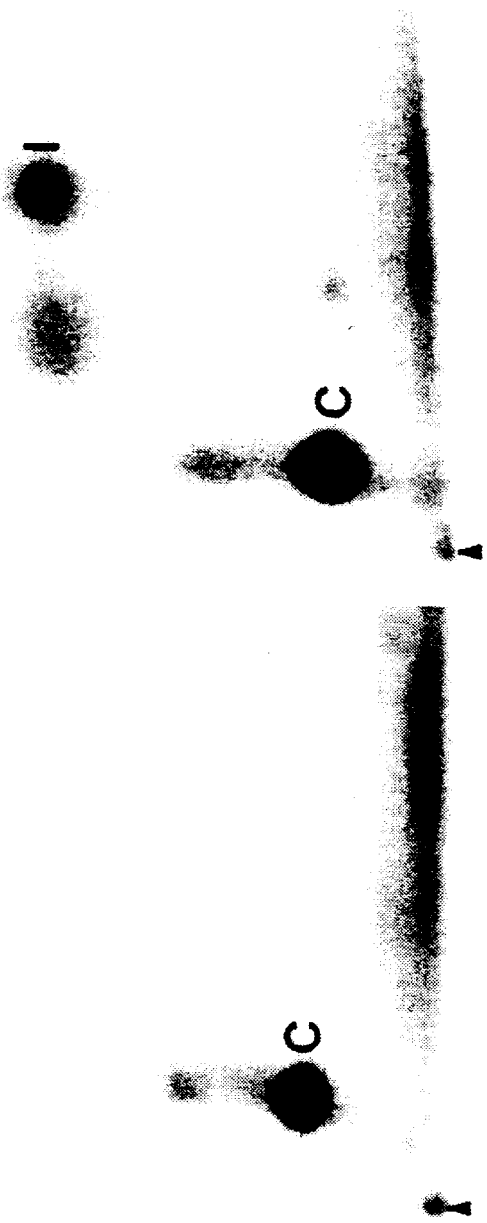

```
(1)                                                       GGGCGGGCGAGGGATCTGAAACTTGCCCACCCTTCGGGATATTGCAGGACGCTGCATC

(59)    ATG AGC GAC AGT AAA TGT GAC AGT CAG TTT TAT AGT GTG CAA GTG GCA GAC TCA ACC TTC ACT GTC CTA AAA CGT TAC
(1)      M   S   D   S   K   C   D   S   Q   F   Y   S   V   Q   V   A   D   S   T   F   T   V   L   K   R   Y (137)   CAG CAG CTG AAA CCA ATT GGC TCT GGG GCC CAA GGG ATT GTT TGT GCT GCA TTT GAT ACA GTT CTT GGG ATA AGT GTT
(27)     Q   Q   L   K   P   I   G   S   G   A   Q   G   I   V   C   A   A   F   D   T   V   L   G   I   S   V (215)   GCA GTC AAG AAA CTA AGC CGT CCT TTT CAG AAC CAA ACT CAT GCA AAG AGA GCT TAT CGT GAA CTT GTC CTC TTA AAA
(53)     A   V   K   K   L   S   R   P   P   Q   N   Q   T   H   A   K   R   A   Y   R   E   L   V   L   L   K (293)   TGT GTC AAT CAT AAA AAT ATA ATT AGT TTG TTA AAT GTG TTT ACA CCA CAA AAA ACT CTA GAA GAA TTT CAA GAT GTG
(79)     C   V   N   H   K   N   I   I   S   L   L   N   V   F   T   P   Q   K   T   L   E   E   F   Q   D   V (371)   TAT TTG GTT ATG GAA TTA ATG GAT GCT AAC TTA TGT CAG GTT ATT CAC ATG GAG CTG GAT CAT GAA AGA ATG TCC TAC
(105)    Y   L   V   M   E   L   M   D   A   N   L   C   Q   V   I   H   M   E   L   D   H   E   R   M   S   Y (449)   CTT CTT TAC CAG ATG CTT TGT GGT ATT AAA CAT CTG CAT TCA GCT GGT ATA ATT CAT AGA GAT TTG AAG CCT AGC AAC
(131)    L   L   Y   Q   M   L   C   G   I   K   H   L   H   S   A   G   I   I   H   R   D   L   K   P   S   N (527)   ATT GTT GTG AAA TCA GAC TGC ACC CTG AAG ATC CTT GAC TTT GGC CTG GCC CGG ACA GCG TGC ACT AAC TTC ATG ATG
(157)    I   V   V   K   S   D   C   T   L   K   I   L   D   F   G   L   A   R   T   A   C   T   N   F   M   M (605)   ACC CCT TAC GTG GTG ACA CGG TAC TAC CGG GCG CCC GAA GTC ATC CTG GGT ATG GGC TAC AAA GAG AAC GTT GAT ATC
(183)    T   P   Y   V   V   T   R   Y   Y   R   A   P   E   V   I   L   G   M   G   Y   K   E   N   V   D   I (683)   TGG TCA GTG GGT TGC ATC ATG GGA GAG CTG GTG AAA GGT TGT GTG ATA TTC CAA GGC ACT GAC CAT ATT GAT CAG TGG
(209)    W   S   V   G   C   I   M   G   E   L   V   K   G   C   V   I   F   Q   G   T   D   H   I   D   Q   W (761)   AAT AAA GTT ATT GAG CAG CTG GGA ACA CCA TCA GCA GAG TTC ATG AAG AAA CTT CAG CCA ACT GTG AGG AAT TAT GTC
(235)    N   K   V   I   E   Q   L   G   T   P   S   A   E   F   M   K   K   L   Q   P   T   V   R   N   Y   V (839)   GAA AAC AGA CCA AAG TAT CCT GGA ATC AAA TTT GAA GAA CTC TTT CCA GAT TGG ATA TTC CCA TCA GAA TCT GAG CGA
(261)    E   N   R   P   K   Y   P   G   I   K   F   E   E   L   F   P   D   W   I   F   P   S   E   S   R   R (917)   GAC AAA ATA AAA ACA AGT CAA GCC AGA GAT CTG TTA TCA AAA ATG TTA GTG ATT GAT CCT GAC AAG CGG ATC TCT GTA
(287)    D   K   I   K   T   S   Q   A   R   D   L   L   S   K   M   L   V   I   D   P   D   K   R   I   S   V (995)   GAC GAA GCT CTG CGT CAC CCA TAC ATC ACT GTT TGG TAT GAC CCC GCC GAA GCA GAA GCC CCA CCA CCT CAA ATT TAT
(313)    D   E   A   L   R   H   P   Y   I   T   V   W   Y   D   P   A   E   A   E   A   P   P   P   Q   I   Y (1073)  GAT GCC CAG TTG GAA GAA AGA GAA CAT GCA ATT GAA GAA TGG AAA GAG CTA ATT TAC AAA GAA GTC ATG GAT TGG GAA
(339)    D   A   Q   L   E   E   R   E   H   A   I   E   E   W   K   E   L   I   Y   K   E   V   M   D   W   E (1151)  GAA AGA AGC AAG AAT GGT GTT GTA AAA GAT CAG CCT TCA GAT GCA GCA GTA AGT AGC AAC GCC ACT CCT TCT CAG TCT
(365)    E   R   S   K   N   G   V   V   K   D   Q   P   S   D   A   A   V   S   S   N   A   T   P   S   Q   S (1229)  TCA TCG ATC AAT GAC ATT TCA TCC ATG TCC ACT GAG CAG ACG CTG GCC TCA GAC ACA GAC AGC AGT CTT GAT GCC TCG
(391)    S   S   I   N   D   I   S   S   M   S   T   E   Q   T   L   A   S   D   T   D   S   S   L   D   A   S (1307)  ACG GGA CCC CTT GAA GGC TGT CGA TGA TAGGTTAGAAATAGCAAACCTGTCAGCATTGAAGGAACTCTCACCTCCGTGGGCCTGAAATGCTTGG
(417)    T   G   P   L   E   G   C   R   *

(1401)  GAGTTGATGGAACCAAATAGAAAAACTCCATGTTCTGCATCTAAGAAACACAAATGCCTTGCCCTATTCAGACCTGATAGGATTGCCTGCTTAGATGATAAAAT
(1504)  GAGGCAGAATATGTCTGAAGAAAAAAATTGCAAGCCACACTTCTAGAGATTTTGTTCAAGATCATTTCAGGTGAGCAGTTAGAGTAGGTGAATTTGTTTCAAA
(1607)  TTGTACTAGTGACAGTTTCTCATCATCTGTAACTGTTGAGATGTATGTGCATGTGACCACAAATGCTTGCTTGGACTTGCCCATCTAGCACTTTGGAAATCAG
(1710)  TATTTAAATGCCAAATAATCTTCCAGGTAGTGCTGCTTCTGAAGTTATCTCTTAATCCTCTTAAGTAATTT
```

FIG. 28

```
  5        10         15        20         25        30         35        40         45        50
  *                   *                    *                    *                    *
MSDSKCDSQF YSVQVADSTF TVLKRYQQLK PIGSGAQGIV CAAFDTVLGI 55        60         65        70         75        80         85        90         95       100
  *                   *                    *                    *                    *
SVAVKKLSRP FQNQTHAKRA YRELVLLKCV NHKNIISLLN VFTPQKTLEE 105       110        115       120        125       130        135       140        145       150
  *                   *                    *                    *                    *
FQDVYLVMEL MDANLCQVIH MELDHERMSY LLYQMLCGIK HLHSAGIIHR 155       160        165       170        175       180        185       190        195       200
  *                   *                    *                    *                    *
DLKPSNIVVK SDCTLKILDF GLARTACTNF MMTPYVVTRY YRAPEVILGM 205       210        215       220        225       230        235       240        245       250
  *                   *                    *                    *                    *
GYKENVDIWS VGCIMGELVK GCVIFQGTDH IDQWNKVIEQ LGTPSAEFMK 255       260        265       270        275       280        285       290        295       300
  *                   *                    *                    *                    *
KLQPTVRNYV ENRPKYPGIK FEELFPDWIF PSESERDKIK TSQARDLISK 305       310        315       320        325       330        335       340        345       350
  *                   *                    *                    *                    *
MLVIDPDKRI SVDEALRHPY ITVWYDPAEA EAPPPQIYDA QLEEREHAIE 355       360        365       370        375       380        385       390        395       400
  *                   *                    *                    *                    *
EWKELIYKEV MDWEERSKNG VVKDQPSDAA VSSNATPSQS SSINDISSMS 405       410        415       420
  *                   *
TEQTLASDTD SSLDASTGPL EGCR
```

FIG. 29

ONCOPROTEIN PROTEIN KINASE

This application is a continuation application of U.S. application Ser. No. 09/461,649 filed Dec. 14, 1999, now issued as U.S. Pat. No. 6,342,595; which is a continuation application of U.S. application Ser. No. 09/150,201 filed Sep. 8, 1998, now issued as U.S. Pat. No. 6,001,584; which is a divisional application of U.S. application Ser. No. 08/799,913 filed Feb. 13, 1997, now issued as U.S. Pat. No. 5,804,399; which is a continuation application of U.S. application Ser. No. 08/444,393 filed May 19, 1995, now issued as U.S. Pat. No. 5,605,808; which is a divisional application of U.S. application Ser. No. 08/276,860 filed Jul. 18, 1994, now issued as U.S. Pat. No. 5,593,884; which is a continuation-in-part application of U.S. application Ser. No. 08/220,602 filed Mar. 25, 1994, now issued as U.S. Pat. No. 6,514,745; which is a continuation-in-part application of U.S. application Ser. No. 08/094,533 filed Jul. 19, 1993, now issued as U.S. Pat. No. 5,534,426.

This invention was made with support by Howard Hughes Medical Institute and Government support under Grant No. DE-86ER60429, awarded by the Department of Energy and Grant No. CA-50528 and CA-58396, awarded by the National Institute of Health. The Government has certain rights in this invention. Also supported by the Howard Hughes Medical Institute.

BACKGROUND OF THE INVENTION

1. Field of the Invention

This invention relates generally to the field of protein kinases, oncogenes and oncoproteins and, specifically, to a protein kinase which binds, phosphorylates and potentiates the c-Jun N-terminal activation domain.

2. Description of Related Art

A number of viral and cellular genes have been identified as potential cancer genes, collectively referred to as oncogenes. The cellular homologs of viral oncogenes, the proto-oncogenes or c-oncogenes, act in the control of cell growth and differentiation or mediate intracellular signaling systems. The products of oncogenes are classified according to their cellular location, for example, secreted, surface, cytoplasmic, and nuclear oncoproteins.

Proto-oncogenes which express proteins which are targeted to the cell nucleus make up a small fraction of oncogenes. These nuclear proto-oncoproteins typically act directly as transactivators and regulators of RNA and DNA synthesis. Nuclear oncogene products have the ability to induce alterations in gene regulation leading to abnormal cell growth and ultimately neoplasia. Examples of nuclear oncogenes include the myc, ski, myb, fos and jun genes.

The c-Jun protein, encoded by the c-jun proto-oncogene, is an important component of the dimeric, sequence specific, transcriptional activator, AP-1. Like other transcriptional activators, c-Jun contains two functional domains, including a DNA binding domain and a transactivation domain. The DNA binding domain is located at the C-terminus and is a BZip structure which consists of conserved basic (B) and leucine zipper (Zip) domains that are required for DNA binding and dimerization, respectively. The N-terminus contains the transactivation domain. Although c-Jun expression is rapidly induced by many extracellular signals, its activity is also regulated post-translationally by protein phosphorylation. Phosphorylation of sites clustered next to c-Jun's DNA binding domain inhibits DNA binding (Boyle, et al., *Cell*, 64:573, 1991; Lin, et al., *Cell*, 70:777, 1992). Phosphorylation of two other sites, Ser 63 and Ser 73, located within the transactivation domain, potentiates c-Jun's ability to activate transcription (Binetruy, et al., *Nature* 351:122, 1991; Smeal, et al., Nature 354:494, 1991). Phosphorylation rates of these sites are low in non-stimulated cells and are rapidly increased in response to growth factors such as platelet derived growth factor (PDGF) or v-Sis, or expression of oncogenically activated Src, Ras and Raf proteins. In myeloid and lymphoid cells, phosphorylation of these sites is stimulated by the phorbol ester, TPA, but not in fibroblasts and epithelial cells. These differences may be due to different modes of Ha-ras regulation in lymphoid cells versus fibroblasts.

Many proteins cooperate with each other in the activation of transcription from specific promoters. Through this cooperation, a gene can be transcribed and a protein product generated. Members of the Fos proto-oncogene family, along with members of the Jun gene family, form stable complexes which bind to DNA at an AP-1 site. The AP-1 site is located in the promoter region of a large number of genes. Binding of the Fos/Jun complex activates transcription of a gene associated with an AP-1 site. In cells that have lost their growth regulatory mechanisms, it is believed that this Fos/Jun complex may "sit" on the AP-1 site, causing overexpression of a particular gene. Since many proliferative disorders result from the overexpression of an otherwise normal gene, such as a proto-oncogene, it would be desirable to identify compositions which interfere with the excessive activation of these genes.

For many years, various drugs have been tested for their ability to alter the expression of genes or the translation of their messages into protein products. One problem with existing drug therapy is that it tends to act indiscriminately and affects healthy cells as well as neoplastic cells. This is a major problem with many forms of chemotherapy where there are severe side effects primarily due to the action of toxic drugs on healthy cells.

In view of the foregoing, there is a need to identify specific targets in the abnormal cell which are associated with the overexpression of genes whose expression products are implicated in cell proliferative disorders, in order to decrease potential negative effects on healthy cells. The present invention provides such a target.

SUMMARY OF THE INVENTION

The present invention provides a novel protein kinase (JNK) which phosphorylates the c-Jun N-terminal activation domain. JNK1 is characterized by having a molecular weight of 46 kD (as determined by reducing SDS-polyacrylamide gel electrophoresis (PAGE)) and having serine and threonine kinase activity. Specifically, JNK1 phosphorylates serine residues 63 and 73 of c-Jun.

Since the product of the jun proto-oncogene is a transactivator protein which binds at AP-1 sites, regulation of c-Jun activation may be important in affecting normal gene expression and growth control in a cell. The discovery of JNK provides a means for identifying compositions which affect JNK activity, thereby affecting c-Jun activation and subsequent activation of genes associated with AP-1 sites.

The identification of JNK now allows the detection of the level of specific kinase activity associated with activation of c-Jun and AP-1. In addition, the invention provides a method of treating a cell proliferative disorder associated with JNK by administering to a subject with the disorder, a therapeutically effective amount of a reagent which modulates JNK activity.

The invention also provides a synthetic peptide comprising the JNK binding region on c-Jun which corresponds to amino acids 33–79. The peptide is useful as a competitive inhibitor of the naturally occurring c-Jun in situations where it is desirable to decrease the amount of c-Jun activation by JNK.

The invention also describes JNK2, a novel protein kinase with activity similar to JNK1 and having a molecular weight of 55 kD.

BRIEF DESCRIPTION OF THE DRAWINGS

FIG. 1 shows an SDS-PAGE of nuclear and cytosolic extracts from FR3T3 (−) and Ha-ras-transformed FR3T3 (+) cells after incubation with $^{32}$P-ATP and GST-cJun (wt), GSTcJun(Ala63/73) or GST.

FIG. 2 shows an SDS-PAGE of A) HeLaS3 cells either untreated or irradiated with UV light and B) Jurkat cells either untreated or incubated with TPA. Cell extracts were incubated with $^{32}$P-ATP and GST-cJun (wt), GSTcjun-(Ala63/73) or GST.

FIG. 7A shows patterns of GST, GSTcJun and GSTvJun as expressed in *E coli*;

FIG. 7B shows the phosphorylated proteins of 7A from extracts of TPA-activated Jurkat cells incubated with GSH-beads;

FIG. 7C shows cJun protein after phosphorylation with protein bound to GSTcJun and GSTvJun beads.

FIGS. 10A–10E shows the nucleotide and deduced amino acid sequence of c-Jun. The arrows represent amino acid residues 33–79.

FIG. 11A shows a Northern blot of total cytoplasmic RNA from Jurkat cells. Cells were incubated with 50 ng/ml TPA (T), 1 µg/ml A23187 (A) or 100 ng/ml cyclosporin A (CsA) for 40 minutes, either alone or in combination, as indicated. Levels of c-jun, jun-B, jun-D, c-fos and α-tubulin expression were determined by hybridization to random primed cDNA probes.

FIG. 11B shows Jurkat cells after incubatation with soluble anti-CD3 (OKT3), 2 µg/ml soluble anti-CD28 (9.3) or a combination of 50 ng/ml TPA and 1 µg/ml A23817 (T/A) as indicated for 40 minutes. Total cytoplasmic RNA was isolated and 10 µg samples were analyzed using c-jun, jun-D and c-fos probes. IL-2 induction by the same treatments was measured after 6 hours of stimulation by blot hybridization using IL-2 and α-tubulin specific probes.

FIG. 12A shows Jurkat cells ($10^6$ cells per lane) transfected with 0.5 µg of a SRα-cJun expression vector and 24 hours later were labeled for 3 hours with $^{32}$P-orthophosphate (1 mCi/ml). After 15 minutes, treatment with 50 ng/ml TPA (T), 1 µg/ml A23187 (A) and 100 ng/ml CsA, either alone or in combination, as indicated, the cells were lysed in RIPA buffer and c-Jun was isolated by immunoprecipitation and analyzed by SDS-PAGE. The c-Jun bands are indicated.

FIG. 12B shows $2 \times 10^7$ Jurkat cells labeled for 3 hours with either $^{35}$S-methionine (900 µCi/ml) or $^{32}$P-orthophosphate (1 mCi/ml). After 15 minutes incubation with 50 ng/ml TPA+1 µg/ml A23178 (T/A) in the absence or presence of and 100 ng/ml CsA or no addition, as indicated, the cells were lysed in RIPA buffer and c-Jun isolated by immunoprecipitation and analyzed by SDS-PAGE. The c-Jun band is indicated.

FIG. 14 shows a phosphorylation assay of cultures of FR3T3, CV-1, PC12 and mouse thymocytes were incubated for 15 minutes in the presence of TPA (50 ng/ml, T), A23817 (1 μg/ml, A) and/or CsA (100 ng/ml), as indicated. WCE prepared from 2–4×10$^5$ cells for the established cell lines and 1.5×10$^6$ cells for primary thymocytes were incubated with GSTcJun(1-223)-GSH agarose beads. After washing, JNK activity was determined by solid-state phosphorylation assay.

FIG. 15 shows WCE (5 μg) of Jurkat (panel A) or mouse thymocytes (panel C) incubated with 1 μg of kinase-defective ERK1 in kinase buffer containing γ-$^{32}$P-ATP for 20 minutes. The phosphorylated proteins were separated by SDS-PAGE and the band corresponding to the mutant ERK1 is indicated. WCE (20 μg) of Jurkat (panel A) or mouse thymocytes (panel C) that were treated as described above were immunoprecipitated with anti-ERK antibodies. The immune complexes were washed and incubated in kinase buffer containing γ-$^{32}$P-ATP and 2 μg MBP for 15 minutes at 30° C. The phosphorylated proteins were separated by SDS-PAGE. The band corresponding to phosphorylated MBP is indicated in panels B and D.

FIGS. 18A and 18D show the nucleotide and deduced amino acid sequence of JNK1.

FIG. 18B shows a comparison of the deduced sequence of JNK1 with other MAP kinases.

FIG. 19A shows a Northern blot analysis of JNK1 in fetal brain.

FIG. 19B shows a Northern blot analysis of JNK1 in adult tissues.

FIG. 19C shows a Southern blot analysis of human genomic DNA hybridized with a JNK1 probe.

FIG. 23 shows immunoprecipitation studies of JNK1 expressed in COS cells and activated by UV (panel A), in Hela cells (panel B), or a mixture of purified ERK1 and ERK2 (panel C). The Coomasie blue stain of the protein substrates is shown in panel D.

FIGS. 24A, 24B, 24C, 24D, and 24E show phosphopeptide map mapping of c-Jun phosphorylated by JNK-46.

FIGS. 27A and 27B show the results of tryptic phosphopeptide mapping of JNK1 purified from F9 cells transfected with epitope tagged JNK1 cells.

FIG. 28 is the nucleotide and deduced amino acid sequence of JNK2.

FIG. 29 is the deduced amino acid sequence of JNK2.

DETAILED DESCRIPTION OF THE INVENTION

Figure 3A:
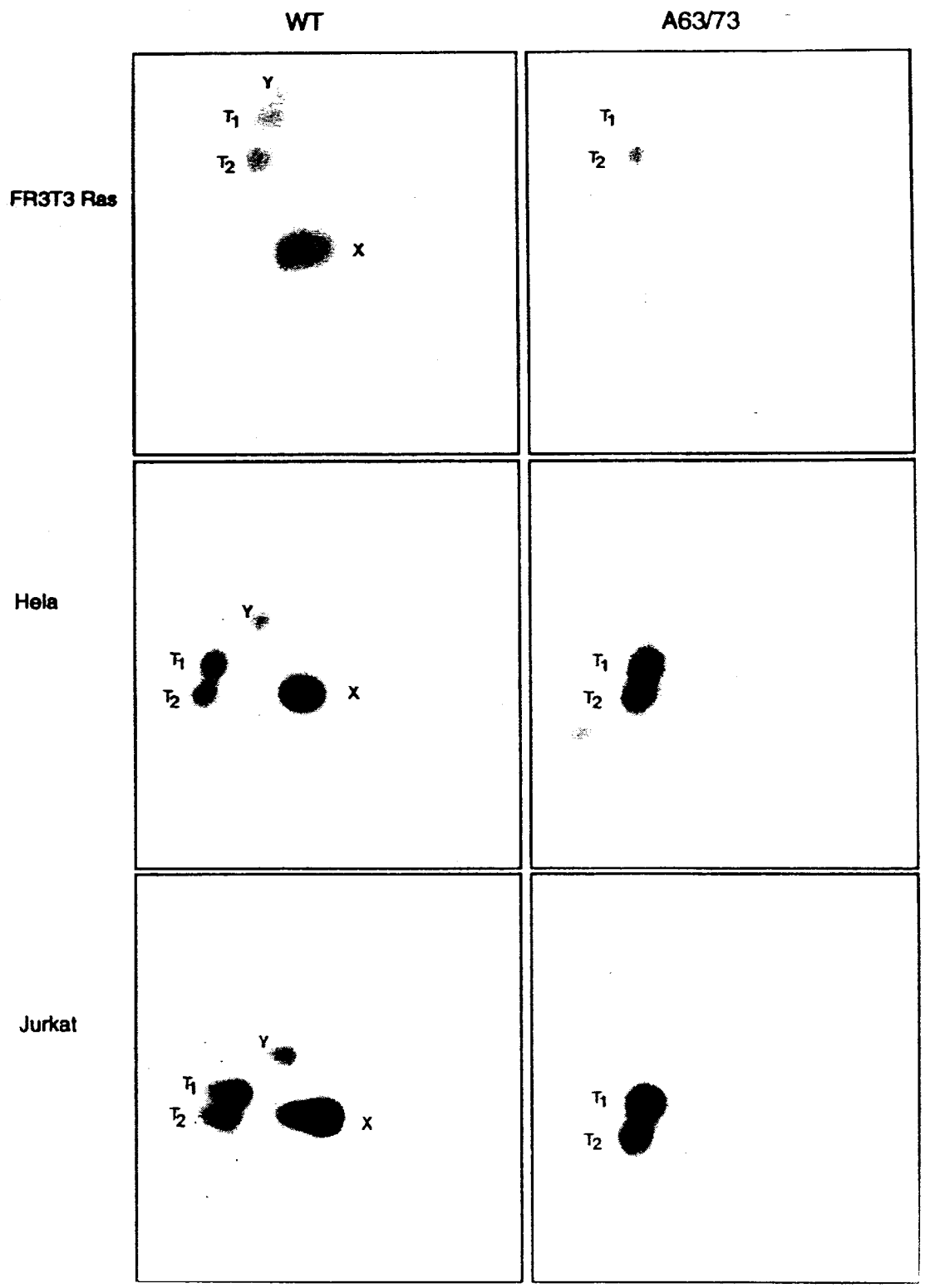
FIG. 3 shows phosphopeptide mapping of GST-cJun and c-Jun phosphorylated by JNK. 3(A) shows maps of GSTcJun and (B) shows maps of c-Jun.

The present invention provides a novel protein kinase (JNK) which binds to a well-defined region of the c-Jun proto-oncoprotein and phosphorylates two sites within its activation domain. The phosphorylation of these sites increases the ability of c-Jun to stimulate transcription and mediate oncogenic transformation.

The activity of c-Jun is regulated by phosphorylation. Various stimuli, including transforming oncogenes and UV light, induce the phosphorylation of serines 63 and 73 in c-Jun's N-terminal activation domain, thereby potentiating its transactivation function. The invention relates to an isolated polypeptide characterized by having a molecular weight of 46 kD as determined by reducing SDS-PAGE, having serine and threonine kinase activity and capable of phosphorylating the c-Jun N-terminal activation domain. This protein is referred to JNK1. In addition, a second JNK protein (55 kD) referred to as JNK2, is described The term "isolated" means any JNK polypeptide of the present invention, or any gene encoding a JNK polypeptide, which is essentially free of other polypeptides or genes, respectively, or of other contaminants with which the JNK polypeptide or gene might normally be found in nature.

The invention includes a functional polypeptide, JNK, and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. The biological function, for example, can vary from a polypeptide fragment as small as an epitope to which an antibody molecule can bind to a large polypeptide which is capable of participating in the characteristic induction or programming of phenotypic changes within a cell. An enzymatically functional polypeptide or fragment of JNK possesses c-Jun N-terminal activation domain kinase activity. A "functional polynucleotide" denotes a polynucleotide which encodes a functional polypeptide as described herein.

Minor modifications of the JNK primary amino acid sequence may result in proteins which have substantially equivalent activity as compared to the JNK polypeptide described herein. Such modifications may be deliberate, as by site-directed mutagenesis, or may be spontaneous. All of the polypeptides produced by these modifications are included herein as long as the kinase activity of JNK is present. Further, deletion of one or more amino acids can also result in a modification of the structure of the resultant molecule without significantly altering its kinase activity. This can lead to the development of a smaller active molecule which would have broader utility. For example, it is possible to remove amino or carboxy terminal amino acids which may not be required for JNK kinase activity.

The JNK polypeptide of the invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides a synthetic peptide which binds to the c-Jun N-terminal kinase, JNK. The amino acid sequence of SEQ ID NO: 1, and conservative variations, comprises the synthetic peptide of the invention. This sequence represents amino acids 33–79 of c-Jun polypeptide (Angel, et al., *Nature*, 332(6160):166, 1988) As used herein, the term "synthetic peptide" denotes a peptide which does not comprise an entire naturally occurring protein molecule. The peptide is "synthetic" in that it may be produced by human intervention using such techniques as chemical synthesis, recombinant genetic techniques, or fragmentation of whole antigen or the like.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods described Merrifield, *J. Am. Chem. Soc.*, 85:2149, 1962), and Stewart and Young, *Solid Phase Peptides Synthesis*, (Freeman, San Francisco, 1969, pp.27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention also provides polynucleotides which encode the JNK polypeptide of the invention and the synthetic peptide of SEQ ID NO: 1. As used herein, "polynucleotide" refers to a polymer of deoxyribonucleotides or ribonucleotides, in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. Preferably, the nucleotide sequence encoding JNK1 is the sequence of SEQ ID NO: 11 and JNK2 is the sequence in FIG. 28.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the poiypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

The development of specific DNA sequences encoding JNK can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to th e presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., *Nucl. Acid Res.* 11:2325, 1983).

A cDNA expression library, such as lambda gt11, can be screened indirectly for JNK polypeptide having at least one epitope, using antibodies specific for JNK. Such antibodies can be either polyclonally or monoclonally derived and used to detect expression product indicative of the presence of JNK cDNA.

A polynucleotide sequence can be deduced from the genetic code, however, the degeneracy of the code must be taken into account. Polynucleotides of the invention include sequences which are degenerate as a result of the genetic code. The polynucleotides of the invention include sequences that are degenerate as a result of the genetic code. There are 20 natural amino acids, most of which are specified by more than one codon. Therefore, as long as the amino acid sequence of JNK results in a functional polypeptide (at least, in the case of the sense polynucleotide strand), all degenerate nucleotide sequences are included in the invention.

The polynucleotide sequence for JNK also includes sequences complementary to the polynucleotide encoding JNK (antisense sequences). Antisense nucleic acids are DNA or RNA molecules that are complementary to at least a portion of a specific mRNA molecule (Weintraub, *Scientific American*, 262:40, 1990). The invention embraces all antisense polynucleotides capable of inhibiting production of JNK polypeptide. In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target JNK-producing cell. The use of antisense methods to inhibit the translation of genes is well known in the art (Marcus-Sakura, *Anal.Biochem.*, 172:289, 1988).

In addition, ribozyme nucleotide sequences for JNK are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med.-Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The JNK polypeptides of the invention can also be used to produce antibodies which are immunoreactive or bind to epitopes of the JNK polypeptides. Antibodies of the invention also include antibodies which bind to the synthetic peptide in SEO ID NO: 1. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the JNK polypeptide of the invention can be prepared using an intact polypeptide or fragments containing small peptides of interest as the immunizing antigen. The polypeptide or a peptide such as Sequence ID No.1 used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in the present invention, an anti-idiotype antibody produced from an antibody which binds to the synthetic peptide of the invention can bind to the site on JNK which binds to c-Jun, thereby preventing JNK from binding to and phosphorylating c-Jun.

Polynucleotide sequences encoding the polypeptide (SEQ ID NO:12 and FIG. 29) or the synthetic peptide (SEQ ID NO: 1) of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

DNA sequences encoding the polypeptides can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the JNK polynucleotide sequences may be inserted into a recombinant expression vector. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyl-transferase). Examples of such markers typically used in mammalian expression vectors include the gene for adenosine deaminase. (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XGPRT, gpt).

Transformation of a host cell with recombinant DNA may be carried out by conventional techniques which are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Examples of mammalian host cells include COS, BHK, 293, and CHO cells.

Isolation and purification of host cell expressed polypeptide, or fragments thereof, provided by the invention, may be carried out by conventional means including preparative chromatography and immunological separations involving monoclonal or polyclonal antibodies.

The JNK protein kinase of the invention is useful in a screening method for identifying compounds or compositions which affect the activity of the kinase. Thus, in another embodiment, the invention provides a method for identifying a composition which affects a c-Jun N-terminal kinase comprising incubating the components, which include the composition to be tested and the kinase or a polynucleotide encoding the kinase, under conditions sufficient to allow the components to interact, then subsequently measuring the effect the composition has on kinase activity or on the polynucleotide encoding the kinase. The observed effect on the kinase may be either inhibitory or stimulatory. For example, the increase or decrease of kinase activity can be measured by adding a radioactive compound to the mixture of components, such as $^{32}$P-ATP, and observing radioactive incorporation into c-Jun or other suitable substrate for JNK, to determine whether the compound inhibits or stimulates protein kinase activity. A polynucleotide encoding the kinase may be inserted into an expression vector and the effect of a composition on transcription of the kinase can be measured, for example, by Northern blot analysis.

In another embodiment, the invention provides a method of treating a cell proliferative disorder associated with JNK comprising administering to a subject with the disorder a therapeutically effective amount of reagent which modulates kinase activity. The term "therapeutically effective" means that the amount of monoclonal antibody or antisense nucleotide, for example, which is used, is of sufficient quantity to ameliorate the JNK associated disorder. The term "cell-proliferative disorder" denotes malignant as well as non-malignant cell populations which morphologically often appear to differ from the surrounding tissue. For example, the method may be useful in treating malignancies of the various organ systems, such as lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine and cancer of the esophagus.

The method is also useful in treating non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, rheumatoid arthritis, acquired immune deficiency syndrome, vasculitis, septic shock and other types of acute inflammation, and lipid histiocytosis. Especially preferred are immunopathological disorders. Essentially, any disorder which is etiologically linked to JNK kinase activity would be considered susceptible to treatment.

Treatment includes administration of a reagent which modulates JNK kinase activity. The term "modulate" envisions the suppression of expression of JNK when it is over-expressed, or augmentation of JNK expression when it is under-expressed. It also envisions suppression of phosphorylation of c-Jun, for example, by using the peptide of SEQ ID NO:1 as a competitive inhibitor of the natural c-Jun binding site in a cell. When a cell proliferative disorder is associated with JNK overexpression, such suppressive reagents as antisense JNK polynucleotide sequence or JNK binding antibody can be introduced to a cell. In addition, an anti-idiotype antibody which binds to a monoclonal antibody which binds a peptide of the invention may also be used in the therapeutic method of the invention. Alternatively, when a cell proliferative disorder is associated with underexpression or expression of a mutant JNK polypeptide, a sense polynucleotide sequence (the DNA coding strand) or JNK polypeptide can be introduced into the cell.

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a peptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Polynucleotide sequences, including antisense sequences, can be therapeutically administered by various techniques known to those of skill in the art. Such therapy would achieve its therapeutic effect by introduction of the JNK polynucleotide, into cells of animals having the proliferative disorder. Delivery of JNK polynucleotide can be achieved using free polynucleotide or a recombinant expression vector such as a chimeric virus or a colloidal dispersion system. Especially preferred for therapeutic delivery of nucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a JNK sequence into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the JNK polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsitation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for JNK polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The invention also provides a method for detecting a cell with JNK kinase activity or a cell proliferative disorder associated with JNK comprising contacting a cell component with c-Jun N-terminal kinase activity with a reagent which binds to the component and measuring the interaction of the reagent with the component. Such reagents can be used to measure relative levels of JNK expression compared to normal tissue. The cell component can be nucleic acid, such as DNA or RNA, or protein. When the component is nucleic acid, the reagent is a nucleic acid probe or PCR primer. The interaction of a nucleic acid reagent with a nucleic acid encoding a polypeptide with c-Jun N-terminal kinase activity is typically measured using radioactive labels, however, other types of labels will be known to those of skill in the art. When the cell component is protein, the reagent is typically an antibody probe. The probes are directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

Preferably the probe for identification of a cell with JNK kinase activity is a c-Jun protein. JNK activity within a cell is measured by the amount of phosphorylation of the c-Jun protein probe. For example, the amount of JNK activity in a cell extract can be measured by mixing the extract with c-Jun protein and adding a radioactive compound such as $^{32}$P-ATP to the mixture of components. The amount of radioactivity that is incorporated into the c-Jun probe is determined, for example by SDS-PAGE, and compared to a cell control containing c-Jun and a normal level of JNK kinase activity.

The c-Jun substrate can be immobilized onto a 96 well microtiter dish and extracts from treated cells added to the wells. The wells are then washed and an appropriate buffer containing $^{32}$P-ATP is added to the wells. The phosphorylation reaction proceeds for about 15 minutes and the wells are washed and counted. Modifications of the assay include immobilizing the substrate using beads or magnetic particles and non-radioactive procedures to measure the substrate phosphorylation, such as using monoclonal antibodies and a detection system (e.g., biotinilated antibodies and avidin peroxidase reaction).

The Jun protein used in the method of detection of the JNK kinase described above may exist as a single protein unit or a fusion protein. The fusion protein preferably consists of c-Jun and glutathione-S-transferase (GST) as a carrier protein. The c-jun nucleotide sequence is cloned 3' to the carrier protein in an expression vector, such as pGEX or such derivatives as pGEX2T or pGEX3X, the gene is expressed, the cells are lysed, and the extract is poured over a column containing a resin or mixed directly with a resin to which the carrier protein binds. When GST is the carrier, a glutathione (GSH) resin is used. When maltose-binding protein (MBP) is the carrier, an amylose resin is used. Other carrier proteins and the appropriate binding resin will be known to those of skill in the art.

The materials of the invention are ideally suited for the preparation of a kit. The kit is useful for the detection of the level of a c-Jun N-terminal kinase comprising an antibody which binds a c-Jun N-terminal kinase or a nucleic acid probe which hybridizes to JNK nucleotide, the kit comprising a carrier means being compartmentalized to receive in close confinement therein one or more containers such as vials, tubes, and the like, each of the container means comprising one of the separate elements to be used in the assay. For example, one of the container means may comprise a monoclonal antibody of the invention which is, or can be, detectably labelled. The kit may also have containers containing buffer(s) and/or a container comprising a reporter-means (for example, a biotin-binding protein, such as avidin or streptavidin) bound to a reporter molecule (for example, an enzymatic or fluorescent label).

The following examples are intended to illustrate but not limit the invention. While they are typical of those that might be used, other procedures known to those skilled in the art may alternatively be used.

EXAMPLE 1

Plasmids and Expression of GST Fusion Proteins

The glutathione-S-transferase (GST)-cJun expression vector, pGEX2T-cJun(wt), was constructed by inserting a filled-in BspHI-PstI fragment (encoding AA 1-223) from RSV-cJun(BspHI) into the SmaI site of pGEX2T (Pharmacia). RSV-cJun(BspHI) was constructed by changing the translation initiation sequence CT<u>ATGA</u> of RSV-cJun to TC<u>ATGA</u> by site-directed mutagenesis. The GSTcJun(Ala63/67)(BspHI) expression vector was derived in the same manner from RSV-cJun(Ala63/73) (Smeal, et al., supra, 1991) and was used to construct pGEX2T-cJun (Ala 63/67). The various GSTcJun truncation mutants were constructed using the polymerase chain reaction (PCR) to amplify various portions of c-Jun coding region. The sequences of the primers are indicated below:

N-terminal primers: TCTGCAGGATCCCC<u>ATG</u>ACTGCAAAGATGGAAACG (underlined codon: amino acid 1) (SEQ ID NO: 2); TCTGCAGGATCCCC<u>GAC</u>GATGCCCTCAACGCCTC (a.a. 11) (SEQ ID NO: 3); TCTGCAGGATCCCC<u>GAG</u>AGCGGACCTTATGGCTAC (a.a. 22) (SEQ ID NO: 4); TCTGCAGGATCCCC<u>GCC</u>GACCC- AGTGGGGAGCCTG (a.a. 43) (SEQ ID NO: 5); TCTGCAGGATCCCC<u>AAG</u>AACTCGGACCTCCTCACC (a.a. 56) (SEQ ID NO: 6) C-terminal primers: TGMTTCTG<u>CAG</u>GCGCTCCAGCTCGGGCGA (a.a. 79) (SEQ ID NO: 7); and TGAATTCCTGCA<u>GGT</u>CGGCGTG-GTGGTGATGTG (a.a. 93) (SEQ ID NO: 8).

The DNA fragments were amplified by using Pfu polymerase (Strategene, La Jolla, Calif.), digested with BamHI and PstI, and subcloned to BamHI, PstI sites of pBluescript SK+ (Strategene). The BamHI-EcoRI fragments were excised from pBluescript and subcloned to BamHI, PstI sites of pGEX3X (Pharmacia). Some constructs were made by inserting BamHI-AvaI fragments of the PCR products and the AvaI-EcoRI fragment of pGEX2T-cJun(wt) into BamHI, EcoRI sites of pGEX3X. pGEX3X-cJun(33-223) was constructed by inserting a XhoII-EcoRI fragment into pGEX3X.

The v-Jun and chick c-Jun sequences were derived from RCAS VC-3 and RCAS CJ-3 respectively (Bos, et al., *Genes Dev.*, 4:1677, 1990). GSTfusion vectors for v-Jun and chicken c-Jun were constructed by inserting NcoI fragments of RCAS VC-3 and RCAS CJ-3 into NcoI site of pGEX-KG (Guan and Dixon, *Anal. Biochem.*, 192:262, 1989). The same fragments contain various portions of the c-Jun and v-Jun coding regions were cloned into pSG424, a GAL4 DNA binding domain expression vector (Sadowski and Ptashne, *Nucl. Acids Res.*, 17:753, 1989).

The GST fusion protein expression vectors were transformed into the XL1-Blue or NM522 strains of *E. coli*. Protein induction and purification were performed as previously described (Smith and Johnson, *Gene*, 67:31, 1988). The amount of purified fusion protein was estimated by the Bio-Rad Protein Assay Kit. In some experiments GST fusion proteins were not eluted from the glutathione (GSH)-agarose beads and were retained on the beads for isolation of the c-Jun N-terminal kinase.

Cell Culture and Preparation of Cell Extracts

FR3T3, Ha-ras transformed FR3T3, HeLaS3 and QT6 cells were grown in Dulbecco's modified Eagle's Medium (DMEM) containing 10% fetal calf serum (FCS), 100 U/ml penicillin (Pc), and 100 µg/ml streptomycin (Sm). Jurkat, K562 and U937 cells were grown in RPMI 1640 supplemented with 10% FCS, 100 U/ml Pc, and 100 µg/ml Sm. F9 cells were grown in 45% DMEM, 45% Ham's F12, 10% FCS, 100 U/ml Pc and 100 µg/ml Sm. Nuclear and cytoplasmic extracts were prepared as described by Dignam, et al., (1983). To prepare whole cell extract (WCE), harvested cells were suspended in WCE buffer: 25 mM HEPES pH 7.7, 0.3 M NaCl; 1.5 mM MgCl$_2$0.2 mM EDTA, 0.1% Triton X-100, 0.5 mM DTT, 20 mM β-glycerophosphate, 0.1 mM N$_3$VO$_4$, 2 µg/ml leupeptin, 100 µg/ml PMSF. The cell suspension was rotated at 4° C. for 30 minutes and the extract was cleared by centrifugation at 10,000×g for 10 minutes. Protein amount was estimated by Bio-Rad Protein Assay Kit.

Transfection Experiments

Transfection experiments were performed using RSV-cJun, RSV-vJun and GAL4-Jun, GAL4-vJun and Ha-Ras (Leu 61) expression vectors as previously described (Boyle, et al., supra, 1991; Binetruy, et al., supra, 1991; Smeal, et al., supra, 1991). CAT activity was determined as described in Example 8 below. c-Jun and v-Jun protein expression and phosphorylation were analyzed as described by Smeal, et al., supra, 1991; Smeal, et al., *Mol. Cell Biol.*, 12:3507, 1992).

Protein Purification

GST-fusion proteins were purified by affinity chromatography on GSH-agarose as described (Smith, et al., *Gene*, 67:31–40, 1988). Purified MAP kinase (a mixture of ERK1 and ERK2) was obtained from Dr. M. Cobb (University of Texas Southwestern). JNK-46 was purified from UV-irradiated HeLa S3 cells by standard liquid chromatography. Epitope-tagged JNK was immunopurified from transiently transfected COS cells. Briefly, COS cells were solubilized with 20 mM Tris (pH 7.6), 0.5% NP-40, 250 mM NaCl, 3 mM β-glycerophosphate, 3 mM EDTA, 3 mM EGTA, 100 µM Na orthovanadate, 10 µg/ml leupeptin, 1 mM PMSF. JNK was isolated by immunoaffinity chromatography using the M2 monoclonal antibody bound to protein A-Sepharose. The beads were washed extensively with Buffer A (20 mM Hepes (ph 7.7), 50 mM NaCl, 0.1 mM EDTA, 0.05% Triton X-100). JNK was eluted from the column with 3 M urea in Buffer A and the dialyzed against Buffer A with 10% glycerol.

EXAMPLE 2

Kinase Assays

Solid Phase Kinase Assay

Cell extracts were diluted so that the final composition of the WCE buffer was 20 mM HEPES pH 7.7, 75 mM NaCl, 2.5 mM MgCl$_2$, 0.1 mM EDTA, 0.05% Triton X-100, 0.5 mM DTT, 20 mM β-glycerolphosphate, 0.1 mM Na$_3$VO$_4$, 2 µg/ml leupeptin, 100 µg/ml PMSF. The extracts were mixed with 10 µl of GSH-agarose suspension (Sigma) to which 10 µg of either GST or GST-Jun fusion proteins were bound. The mixture was rotated at 4° C. for 3 hours in a microfuge tube and pelleted by centrifugation at 10,000×g for 20 sec. After 4×1 ml washes in HEPES binding buffer (20 mM HEPES pH 7.7, 50 mM NaCl, 2.5 mM MgCl$_2$, 0.1 mM EDTA, 0.05% Triton X-100), the pelleted beads were resuspended in 30 µl of kinase buffer (20 mM HEPES pH 7.6, 20 mM MgCl$_2$, 20 mM β-glycerolphosphate, 20 µM p-nitrophenyl phosphate, 0.1 mM Na$_3$VO$_4$, 2 mM DTT) containing 20 µM ATP and 5 µCi γ-$^{32}$P-ATP. After 20 minutes at 30° C. the reaction was terminated by washing with HEPES binding buffer. Phosphorylated proteins were eluted with 30 µl of 1.5×Laemlli sample buffer and resolved on a 10% SDS polyacrylamide gel, followed by autoradiography. Quantitation of phosphate incorporated was determined by gel slicing and scintillation counting. Phosphorylated GST fusion proteins were eluted from gel slices and subjected to phosphopeptide mapping as described (Boyle, et al., supra, 1991).

In-Gel Kinase Assay

In-gel kinase assay was performed as described by Kameshita and Fujisawa, *Anal. Biochem.*, 183:139, (1989) with slight modifications. Briefly, c-Jun binding proteins were isolated from whole cell extracts by using GSH-agarose beads containing 80 µg GST-cJun as described above. Proteins were eluted in Laemlli sample buffer and resolved on 10% SDS-polyacrylamide gel, which was polymerized in the absence or presence of GST-cJun (40 µg/ml). After electrophoresis, the gel was washed twice, 30 minutes each time with 100 ml of 20% 2-propanol, 50 mM HEPES pH 7.6 to remove SDS. After the gel was washed twice, 30 minutes each time, with 100 ml of buffer A (50 mM HEPES pH 7.6, 5 mM β-mercaptoethanol), it was incubated in 200 ml of 6M urea in buffer A at room temperature for 1 hr, followed by serial incubations in buffer A containing 0.05% Tween 20 and either 3M, 1.5M or 0.75M urea. After the gel was washed several times, 1 hr each time, with 100 ml of buffer A containing 0.05% Tween 20 at 4° C., it was incubated with kinase buffer containing 50 µM ATP and 5 µCi/ml γ-$^{32}$P-ATP at 30° C. for 1 hour. After the reaction, the gel was washed with 100 ml of 5% tricholoroacetic acid and 1% sodium pyrophosphate at room temperature several times, followed by drying and autoradiography.

EXAMPLE 3

Binding of a Protein Kinase to GST-cJun-GSH-AGAROSE Beads

The fusion protein, GSTcJun(wt), can bind through its GST moiety to glutathione (GSH)-agarose beads to generate an affinity matrix for identification of c-Jun binding proteins, which may include protein kinases. Ha-ras transformation of FR3T3 cells results in increased phosphorylation of c-Jun on Ser 63 and 73 (Binetruy, et al., supra, 1991; Smeal, et al., supra, 1991). Preliminary experiments indicated that transformed cells contained higher levels of c-Jun N-terminal kinase activity, while the levels of c-Jun C-terminal kinase activity remained unchanged. To develop a more convenient assay for characterizing the c-Jun N-terminal kinase activity, nuclear and cytoplasmic extracts of untransformed and transformed FR3T3 cells were mixed with GSTcJun(wt)-GSH-agarose beads. FRT3T3(−) and Ha-ras-transformed FR3T3(+) cells were kept in 0.5% FCS for 24 hours and harvested to prepare nuclear and cytosolic extracts. These extracts (prepared from equal number of cells) were mixed with GSH-agarose beads containing 10 µg of GST-cJun(wt), GSTcJun(Ala63/73) or GST. After a 3 hour incubation, the beads were spun down, washed 4-times and incubated in kinase buffer containing γ-$^{32}$P-ATP for 20 minutes at 30° C. The reaction was terminated by washing in SDS sample buffer. The eluted proteins were resolved by SDS-PAGE. The location of the GSTcJun fusion proteins is indicated in FIG. 1. Similar results were obtained when protein concentration rather than cell number (300 µg of cytosolic extract and an equivalent amount of nuclear extract) was used to normalize the amounts of extracts used in this assay. This procedure resulted in phosphorylation of GSTcJun(wt), suggesting that a protein kinase bound to it and phosphorylated it while attached to GSH-agarose (FIG. 1). On the other hand, no phosphorylation of GST bound to GSH-agarose could be detected by this assay.

The same experiment was repeated using a GSTcJun (Ala63/73) fusion protein, in which both the serine at position 63 and 73 were converted to alanines in order to identify a kinase that targets Ser 63 and 73 of c-Jun. Phosphorylation of this protein was considerably lower than that of GSTcJun(wt) (FIG. 1). These experiments confirmed the previous observations that the kinase activity affecting the N-terminal sites of c-Jun was elevated upon Has-ras transformation and are consistent with the differences in the extent of c-Jun N-terminal phosphorylation between transformed and untransformed cells detected by in vivo labelling (Binetruy, et al., supra, 1991; Smeal, et al., supra, 1991, 1992). The kinase activity detected by this solid-phase assay was present in both the cytosolic and the nuclear fractions and was several-fold more abundant in the cytosol on a per-cell basis. However, it is possible that some of the kinase leaked from the nuclei to the cytosol during the cell fractionation.

The solid-phase assay was used to examine N-terminal c-Jun kinase activity in other cell types. Exposure of HeLa cells to UV activates the Ha-Ras signalling pathway and results in a large increase in N-terminal phosphorylation of c-Jun (Devary, et al., *Cell*, 71:1081, 1992). Treatment of HeLa cells with the phorbol ester, TPA, on the other hand, has only a marginal effect on N-terminal phosphorylation of c-Jun (Boyle, et al., 1991). HeLa S3 cells were serum starved for 12 hours and were either left untreated, irradiated with UV light (40 J/m$^2$) or incubated with TPA (100 ng/ml). The cells were harvested at the indicated times (min) after UV or TPA exposure. Whole cell extracts (approximately 800 µg protein) isolated form equal numbers of cells were mixed with GSH-agarose beads containing 10 µg of either GST, GSTcJun(wt), or GSTcJun(Ala 63/73). After 3 hours incubation, followed by extensive washing, the solid state phosphorylation assay was performed as described above. After a 20 minute reaction, the proteins were dissociated in SDS sample buffer and resolved by SDS-PAGE.

As shown in FIG. 2A, N-terminal c-Jun kinase activity was elevated within 5 minutes after UV irradiation and was 250-fold higher after 30 minutes than in unstimulated cells. The effect of TPA, however, was minor compared to that of UV. As found before, GSTcJun(wt) was more efficiently phosphorylated than GSTcJun(Ala63/73), whereas GST was not phosphorylated. These results are consistent with in vivo measurements of c-Jun phosphorylation (Boyle, et al., supra, 1991; Devary, et al., supra, 1992).

TPA treatment of Jurkat T cells, in contrast to HeLa cells, resulted in stimulation of c-Jun phosphorylation on Ser 63 and 73. Jurkat cells were serum starved for 2 hours and either left untreated or stimulated with TPA (50 ng/ml) for 10 or 30 minutes. Whole cell extracts prepared from 5×10$^6$ cells were mixed with GSH-agarose beads containing GST, GSTcJun(wt) or GSTcJun(Ala63/73). Phosphorylation of the GST proteins attached to the beads was performed as described above. The faster moving bands correspond to degradation products of the GSTcJun proteins.

In Jurkat cells, unlike HeLa cells, the N-terminal kinase activity was found to be strongly activated by TPA (25-fold after 30 minutes) (FIG. 2B). This kinase also preferred GSTcJun(wt) over GSTcJun(Ala63/73) and did not bind to or phosphorylate the GST moiety. Collectively, these findings suggest that the kinase detected by the solid-phase assay phosphorylates c-Jun on Ser 63 and 73 and that its regulation parallels that of c-Jun N-terminal phosphorylation examined by in vivo labelling.

EXAMPLE 4

Phosphorylation of Serines 63 and 73 by Bound Kinase, JNK

To determine the exact phosphoacceptor sites used by the kinase that binds to GSTcJun, the phosphorylated GSTcJun (wt) and GSTcJun(Ala63/73) proteins were subjected to two-dimensional tryptic phosphopeptide mapping. Whole cell extracts of Ha-ras-transformed FR3T3 cells (2.5 mg), UV irradiated HeLa cells (200 µg) or TPA-stimulated Jurkat cells (1.2 mg) were mixed with GSH-agarose beads, containing either GSTcJun(wt) or GSTcJun(Ala63/73). The GSTcJun proteins were phosphorylated as described above by the bound kinase, isolated by SDS-PAGE, excised from the gel, digested with trypsin and subjected to two-dimensional phosphopeptide mapping. The X, Y, T1, and T2 phosphopeptides are indicated. All the autoradiograms were exposed for the same length of time.

As shown in FIG. 3A, the kinases isolated from Ha-ras-transformed FR3T3 cells, UV-irradiated HeLa cells and TPA-stimulated Jurkat cells, phosphorylated GSTcJun on X, Y, and two other peptides, T1 and T2 X and Y correspond to phosphorylation of Ser-73 and Ser-63, respectively (Smeal, et al., supra, 1991) and were absent in digests of GSTcJun (A1a63/73), which contained higher relative levels of T1 and T2. Phosphoaminoacid analysis indicated that T1 and T2 contain only phosphothreonine. By deletion analysis these threonines were assigned to AA 91, 93 or 95 of c-Jun.

Figure 3B:
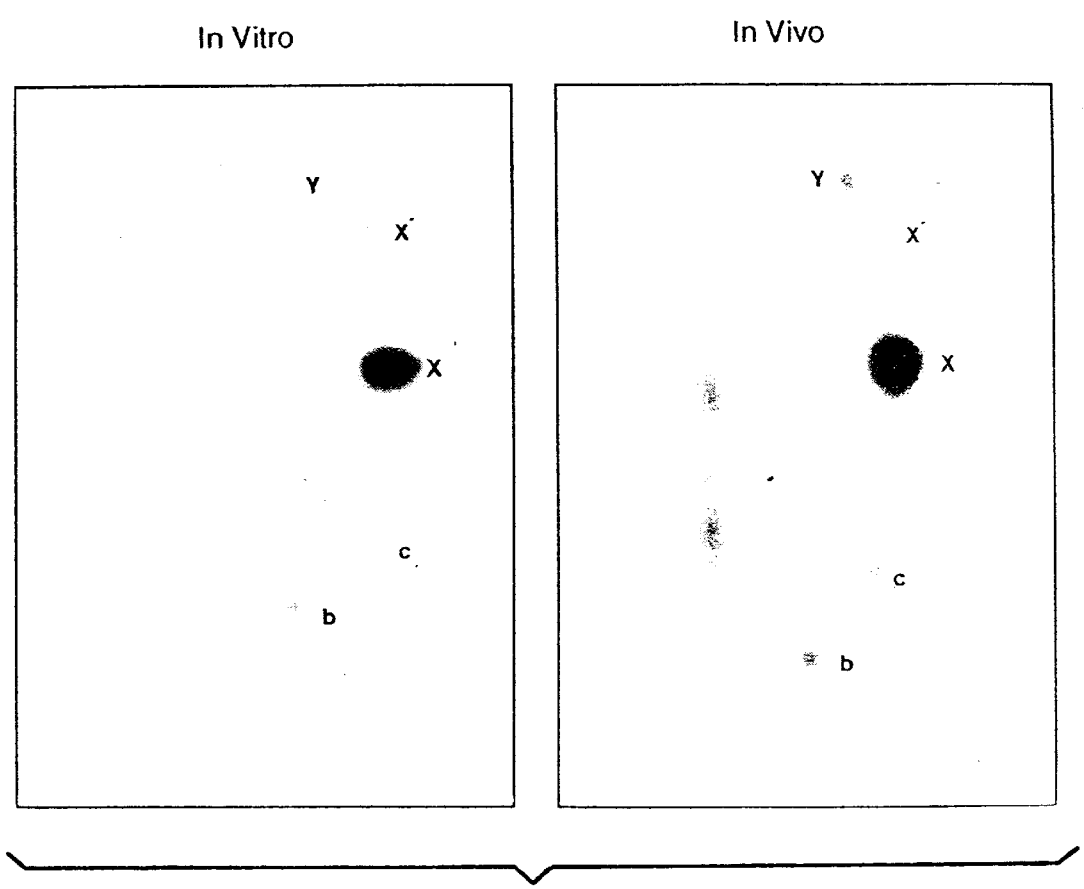

As described below, the kinase bound to GSTcJun was eluted from the beads and used to phosphorylate recombinant full-length c-Jun protein in solution (FIG. 3B). Recombinant c-Jun protein was phosphorylated in vitro by the c-Jun N-terminal kinase (JNK) eluted from GSTcJun(WT)-GSH-agarose beads. In addition, c-Jun was isolated by immuneprecipitation from $^{32}$P-labelled F9 cells that were cotransfected with c-Jun and Ha-Ras expression vectors (Smeal, et al., supra, 1991). Equal counts of each protein preparation were digested with trypsin and subjected to phosphopeptide mapping. The migration positions of the X, X' (a derivative of X generated by alkylation; Smeal, et al., supra, 1991) Y, b and c phosphopeptides are indicated.

As found in vivo, the bound kinase phosphorylated c-Jun mostly on Ser 73, followed by phosphorylation of Ser 63. In addition, the bound kinase activity phosphorylated c-Jun weakly on two of its C-terminal sites, resulting in appearance of phosphopeptides b and c. Since this is the first protein kinase that was detected with clear specificity for at least one of the N-terminal sites of c-Jun, it was named JNK, for cJun N-terminal protein-kinase.

EXAMPLE 5

Binding of JNK to cJun

To examine the stability of the interaction between GSTc-jun and JNK, extracts of TPA-stimulated Jurkat cells were incubated with GSTcJun(wt)-GSH-agarose beads. After extensive washing, the beads were subjected to elution with increasing concentrations of NaCl, urea, guanidine-HCl and SDS. Elution of JNK was examined by its ability to phosphorylate recombinant c-Jun in solution. GSTcjun(wt)-GSH-agarose beads were incubated for 3 hours with a whole cell extract of TPA-stimulated Jurkat cells and after four washes were subjected to elution in kinase buffer containing increasing concentrations of NaCl, urea, guanidine-HCl (in M) or SDS (in %)(FIG. 4). The eluted fractions (equal volumes) were dialyzed at 4° C. against kinase buffer containing 10% glycerol and no ATP and then incubated with recombinant c-Jun protein (250 ng) in the presence of 20 $\mu$M ATP and 5 $\mu$Ci of $\gamma$-$^{32}$P-ATP for 20 minutes at 30° C. The amount of kinase remaining on the beads after the elution steps (R lanes) was determined by incubation of the isolated beads with kinase buffer in the presence of 20 $\mu$M ATP and 5 $\mu$Ci $\gamma$-P-ATP for 20 minutes at 30° C. The phosphorylated proteins were analyzed by SDS-PAGE as described above and visualized by autoradiography. The migration positions of GSTcJun and c-Jun are indicated.

Figure 4A:
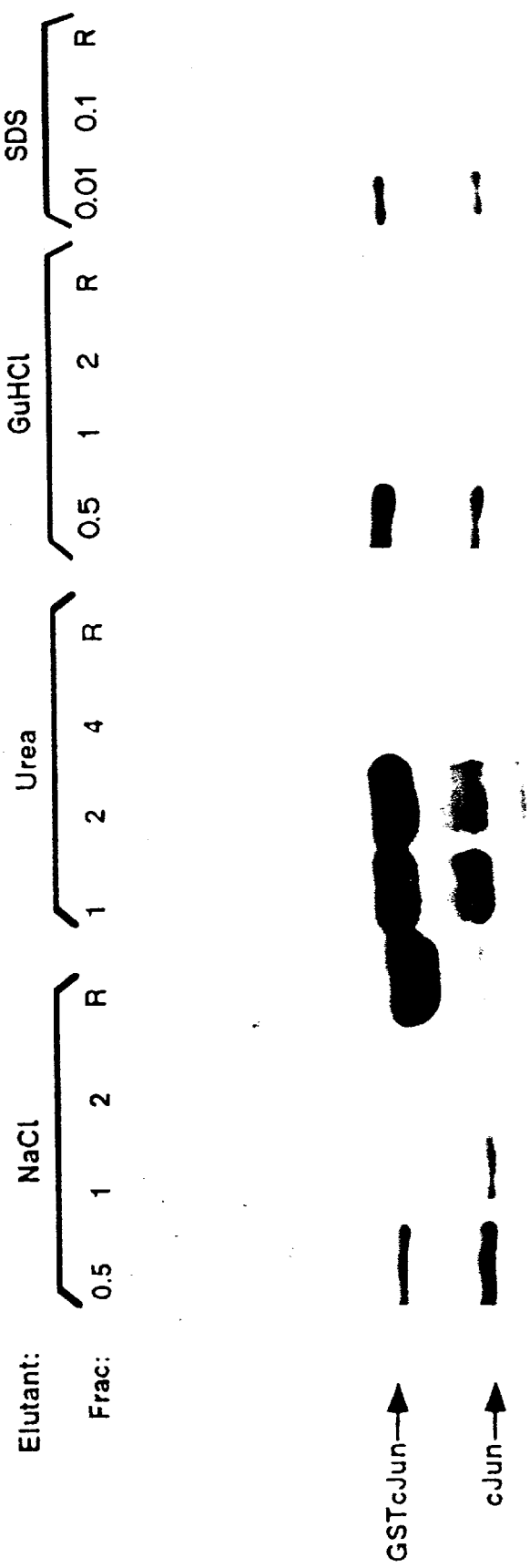
FIG. 4A shows an SDS-PAGE of phosphorylated proteins after elution of JNK from GSTc-Jun after washes of NaCl, Urea, Guanidine-HCl(GuHCl) or SDS.

Surprisingly, JNK was found to bind GSTcJun rather tightly; only a small fraction of kinase activity was eluted by 0.5M NaCl and even after elution with 2M NaCl, most of the kinase remained on the beads (FIG. 4A). Approximately 50% of the bound kinase was eluted by 1M urea and the rest was eluted by 2M urea. Nearly complete elution was achieved by either 0.5M guanidine-HCl or 0.01% SDS. Under all of these elution conditions, GSTcJun(wt) was also partially eluted from the GSH-agarose beads. This suggests that the stability of the JNK:c-Jun complex is similar to that of the GST:GSH complex.

GSTcJun(wt) was covalently linked to GSH-agarose beads, using cyanogenbromide, and incubated with a whole cell extract of TPA-stimulated Jurkat cells. After extensive washing, part of the beads were eluted with kinase buffer-containing: no ATP (FIG. 4B, lane 2), 20 $\mu$M ATP (lane 3) or 50 $\mu$M ATP (lane 4). The eluted fractions (equal volumes) were incubated with recombinant c-Jun protein (500 ng) as a substrate and 5 $\mu$Ci $\gamma$-$^{32}$P-ATP for 30 minutes. In addition, the beads after elution with either kinase buffer alone (lane 1) or kinase buffer containing 50 $\mu$M ATP (lane 5) were incubated with c-Jun protein (500 ng) in the presence of 5 $\mu$Ci $\gamma$-$^{32}$P-ATP for 30 minutes. Phosphorylation of c-Jun (indicted by the arrow) was analyzed by SDS-PAGE and autoradiography.

Figure 4B:
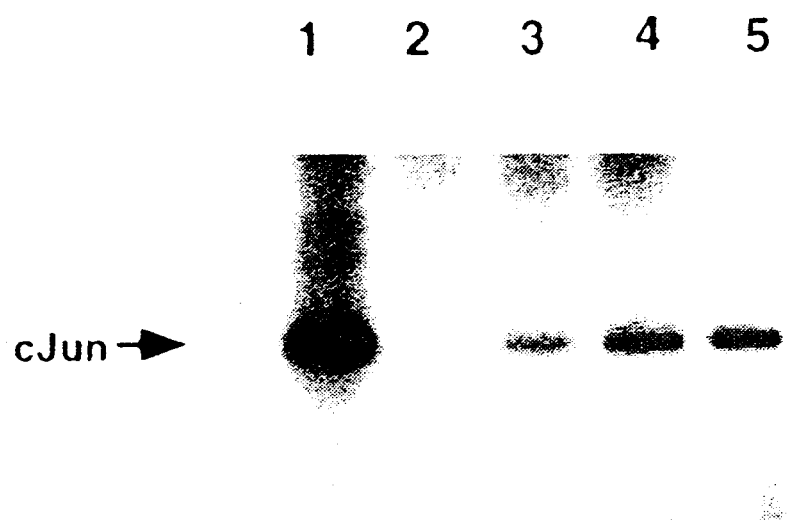
FIG. 4B shows an SDS-PAGE of phosphorylated c-Jun after GSTcJun(wt) was covalently linked to GSH-beads and incubated with whole cell extract of TPA-stimulated Jurkat cells.

Addition of exogenous c-Jun to kinase-loaded GSH-agarose beads to which GSTcJun was covalently linked results in its efficient phosphorylation (FIG. 4B, Lane 1). This suggests that after phosphorylating GSTcJun, JNK dissociates from it and phosphorylates exogenous c-Jun. In addition, incubation with kinase buffer containing ATP resulted in elution of JNK from the GSTcJun beads, as indicated by its ability to phosphorylate exogenous c-Jun (FIG. 4B, lanes 2–4). After incubation with 50 $\mu$M ATP less than 20% of the kinase remained on the beads (compare lanes 1 and 5, FIG. 4B).

EXAMPLE 6

JNK1 is a 46 kD Protein

An in-gel kinase assay was performed to determine the size of JNK. GSTcJun-GSH-agarose beads were incubated with a whole cell extract of TPA-stimulated Jurkat cells, washed extensively and the bound proteins were eluted in SDS sample buffer and separated on SDS-polyacrylamide gels that were polymerized in the absence (−) or presence (+) of GSTcJun(wt). After electrophoresis, the gel was incubated in 6 M urea and subjected to renaturation as described in Example 1. The renatured gels were incubated in kinase buffer containing 50 $\mu$M ATP and 5 $\mu$Ci/ml $\gamma$-$^{32}$P-ATP for 1 hour at 30° C., washed, fixed, and visualized by autoradiography.

Figures 5A, 5B:
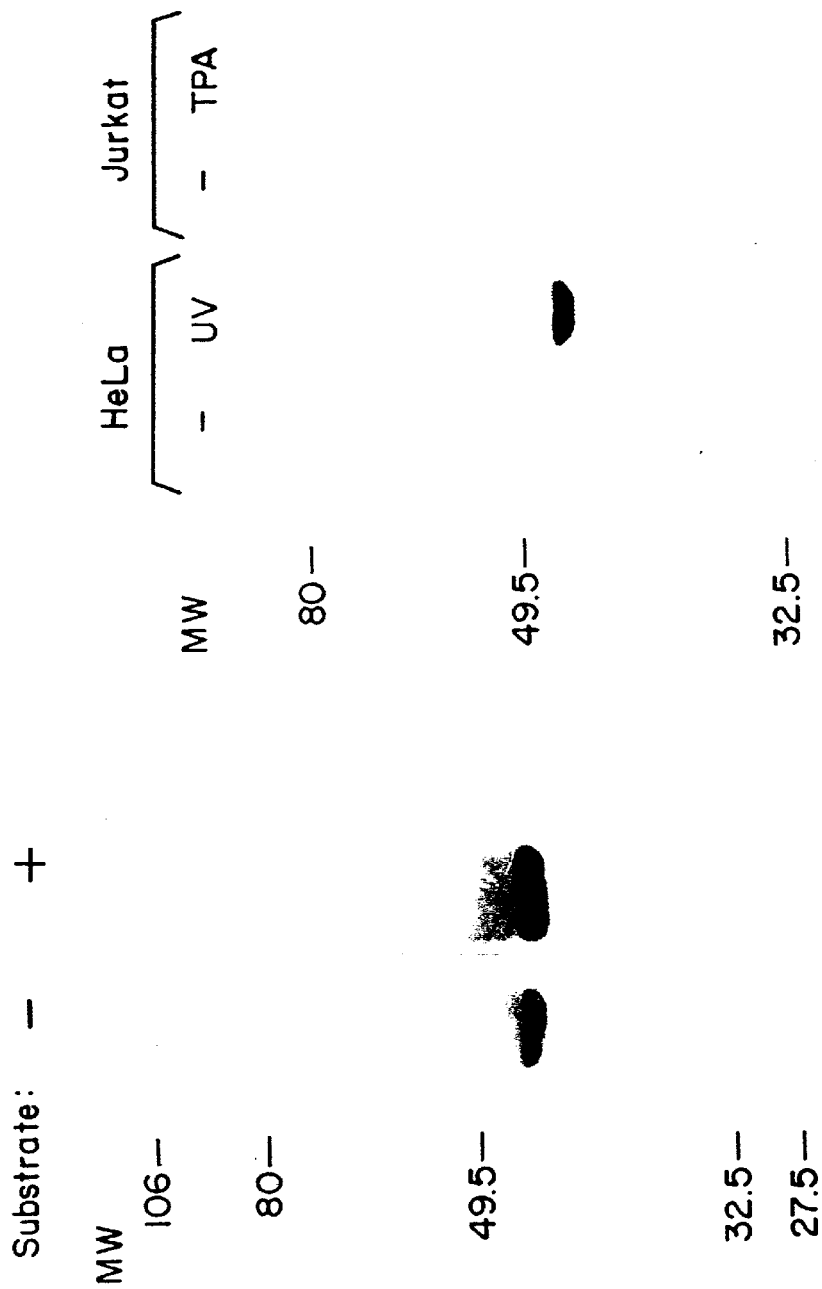
FIG. 5 shows an in-gel kinase assay. GSTcJun-GSH agarose beads were incubated with cell extracts from A) TPA-stimulated Jurkat cells on SDS gels that were polymerized in the absence (−) or presence (+) of GSTcJun (wt); B) extracts of unstimulated or UV stimulated HeLa cells and unstimulated or TPA-stimulated Jurkat cells; and C) extracts from cells of logarithmically growing K562 and Ha-ras-transformed FR3T3, TPA-stimulated Jurkat and U937 cells and UV-irradiated HeLa, F9 and QT6 cells.

In both cases a protein band whose apparent molecular weight was 46 kD was phosphorylated (FIG. 5A). Phosphorylation was 2-fold more efficient in the presence of GSTc-Jun. This indicates that 46 kD protein band is either autophosphorylated JNK or a comigrating protein. No $^{32}$P-labelled protein was detected in eluates of GST-GSH-agarose beads.

The same in-gel kinase assay was used to demonstrate increased JNK activity upon TPA stimulation of Jurkat cells or UV irradiation of HeLa cells (FIG. 5B). GSTcJun-GSH-agarose beads were incubated with whole cell extracts of unstimulated or UV-stimulated HeLa cells and unstimulated or TPA-stimulated Jurkat cells. After washing, the bound proteins were eluted in SDS sample buffer and separated by SDS-PAGE. After renaturation, the gel was incubated in kinase buffer containing 50 $\mu$M ATP and 5 $\mu$Ci/ml $\gamma$-$^{32}$P-ATP and the phosphorylated proteins were visualized by autoradiography.

Figure 5C:
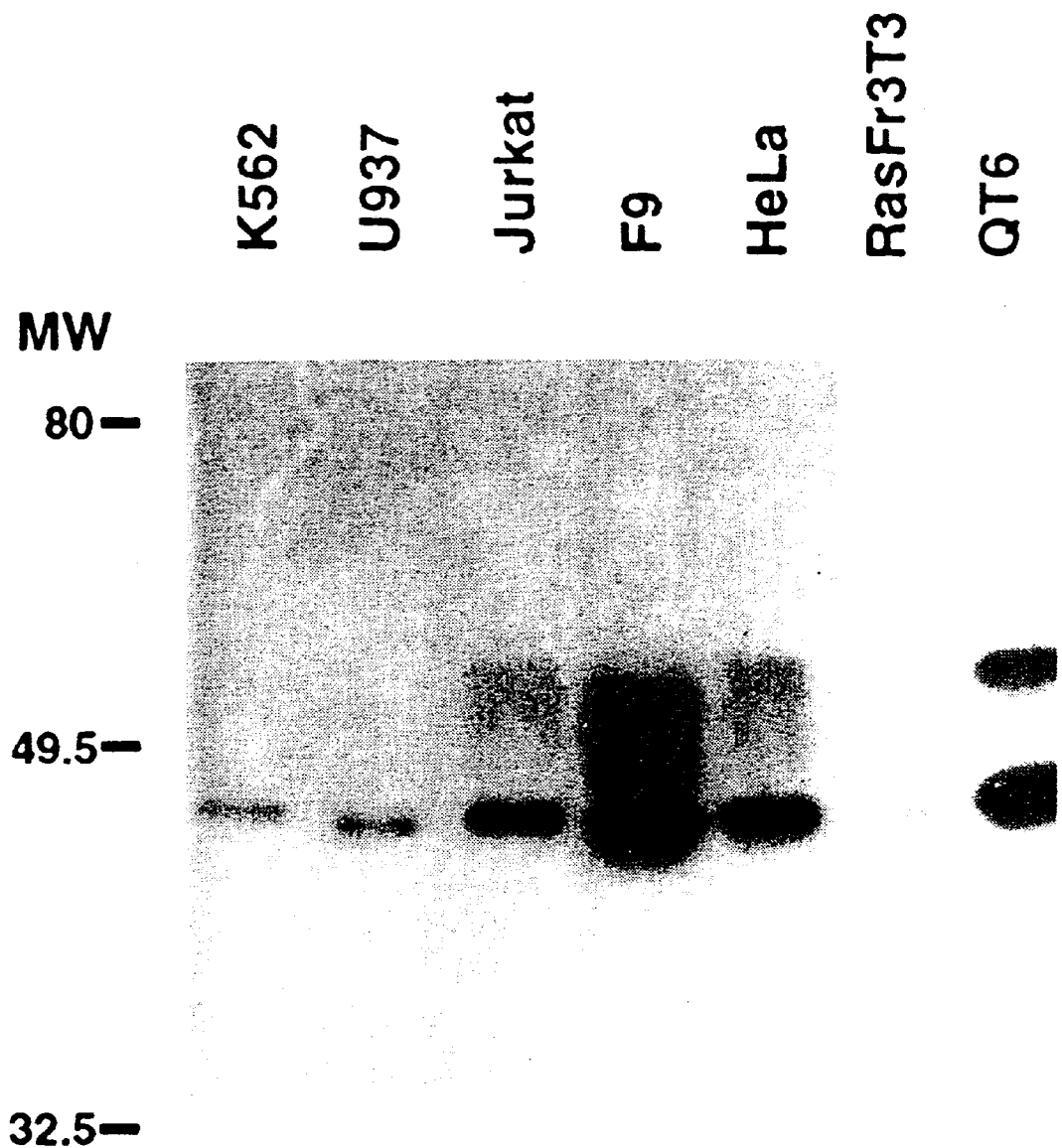

These results provide further evidence that the apparent molecular weight of JNK is 46 kD. To determine whether the same N-terminal c-Jun kinase is present in various cell types, the in-gel kinase assay was used to examine extracts of K562 human erythroleukemia cells, U937 human histiocytic leukemia cells, Jurkat cells, HeLa cells, F9 embryonal carcinoma cells, Ha-ras-trans-formed FR3T3 cells and QT6 quail fibroblasts. The HeLa, F9 and QT6 extracts were prepared form UV-irradiated cells and the U937 and Jurkat extracts were made from TPA-stimulated cells, while the K562 cells were not subjected to any special treatment. All cells contained a protein kinase that bound to GSTcJun and migrated around 46 kD (FIG. 5C). Some cells, especially QT6 cells, contained a second less abundant protein kinase species, migrating at about 55 kD. The activities of both kinases were induced by cell stimulation. GSTcJun(WT)-GSH-agarose beads were incubated with whole cell extracts of logarithmically growing K562 and Ha-ras transformed FR3T3 cells, TPA-stimulated Jurkat and U937 cells and UV-irradiated HeLa, F9 and QT6 cells. After washing, the bound proteins were eluted and analyzed by in-gel kinase assay as described above.

Further evidence that JNK is 46 kD in size was obtained by separating the GSTcJun-bound protein fraction of TPA-stimulated Jurkat cell extract by SDS-PAGE. After elution and renaturation of the fractionated proteins, the molecular weight of the major protein kinase bound to GSTcJun, capable of specific phosphorylation of Ser 63 and 73, was determined to be 46 kD. Although the sizes of ERK1 and ERK2, 44 and 42 kD, respectively, are close to that of JNK, Western blot analysis, using an antiserum that reacts with both ERK's, indicates that the 46 kD JNK is not immunologically related to either of them. In addition, JNK is not immunologically related to Raf-1. In addition, a 55 kD polypeptide was identified as exhibiting JNK activity, however, the 46 kD appears to bind c-Jun more efficiently (Hibi, et al., Genes Dev., 7:2135, 1993).

EXAMPLE 7

Delineation of the Kinase Binding Site

Figure 6A:
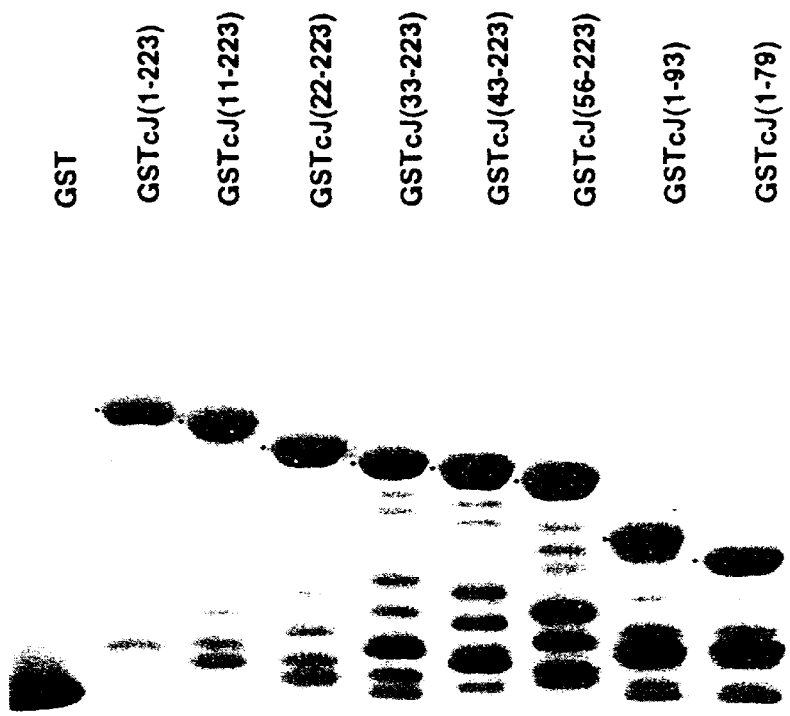
FIG. 6A is a protein gel of various GST c-Jun fusion proteins.

Deletion mutants of GSTcJun lacking either N-terminal or C-terminal sequences (FIG. 6A) were used to define the JNK binding site. GSTcJun fusion proteins containing various c-Jun sequences were expressed in E. coli and isolated by binding to GSH-agarose. The bound proteins were analyzed by SDS-PAGE and stained with Coomassie Blue. Numbers indicate the amino acids of c-Jun present in each fusion protein. The migration positions of the intact GST-fusion proteins are indicated by the dots. Faster migrating bands are degradation products.

These proteins were immobilized on GSH-agarose beads and incubated with an extract of UV-irradiated HeLa cells. Whole cell extracts of UV-irradiated HeLa S3 cells were mixed with GSH-agarose beads containing equal amounts of the various GST fusion proteins. After washing, the beads were incubated for 20 minutes in kinase buffer containing $\gamma$-$^{32}$P-ATP. The GST-fusion proteins were eluted from the beads and analyzed by SDS-PAGE and autoradiography. The migration positions of the intact GST fusion proteins are indicated by the dots. After incubation with whole cell extracts of UV-irradiated HeLa cells and washing, part of the bound JNK fraction was eluted with 1 M NaCl and examined for its ability to phosphorylate recombinant c-Jun (250 ng) in solution. Protein phosphbrylation was analyzed by SDS-PAGE and autoradiography.

Figure 6B:
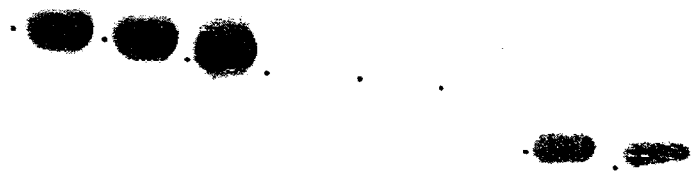
FIG. 6B shows an SDS-PAGE of whole cell extracts of UV-irradiated Hela S3 cells after passage over GSH-beads containing the GST fusion proteins as shown in FIG. 6A.
Figure 6C:
FIG. 6C shows an SDS-PAGE of phosphorylated GSTc-Jun fusion proteins eluted with 1MNaCl from GSH-agarose beads.

Binding of JNK was examined by its ability to phosphorylate the GSTcJun fusion proteins, all of which contained both Ser 63 and 73 (FIG. 6B). To exclude the possibility that any of the truncations may have altered the conformation of c-Jun affecting the presentation of its N-terminal phospho-acceptors without affecting JNK binding, the kinase eluted from these beads was examined for its ability to phospho-rylate exogenous full-length c-Jun in solution (FIG. 6C). The results obtained by both assays indicated that removal of amino acids (AA) 1–21 had no effect on JNK binding. Removal of AA 1–32 decreased phosphorylation of GSTc-Jun but had only a small effect on kinase binding. Removal of AA 1–42, however, completely eliminated kinase binding. In contrast to the N-terminal truncations, the two. C-terminal truncations, that were examined, had no effect on JNK binding and a GST fusion protein containing AA 1–79 of c-Jun exhibited full binding activity. Hence, AA 33–79 constitute the kinase binding site.

The JNK binding site encompasses the δ region, spanning AA 31–57 of c-Jun that are deleted in v-Jun (Vogt and Bos, 1990). To determine the involvement of the δ region in kinase binding, GST fusion proteins containing the N-terminal activation domain of chicken c-Jun (AA 1–144), or the equivalent region of v-Jun (FIG. 7A) were constructed. The activation domain (AA 1–144) of chicken (ch) c-Jun and the equivalent region of v-Jun were fused to GST and expressed in E. coli. GST fusion proteins were isolated on GSH-agarose beads and analyzed by SDS-PAGE and Coomassie Blue staining. The migration positions of the intact proteins are indicated by the dots. After loading these GST fusion proteins onto GSH-agarose the kinase binding assays were performed as described above.

Extracts of TPA-activated Jurkat cells were incubated with GSH-agarose beads containing GST, GSTcJun(Ch) or GSTvJun. After washing, the beads were incubated in kinase buffer containing $\gamma$-$^{32}$P-ATP and the phosphorylated GST fusion protein were analyzed as described for FIG. 6. The bound protein fraction was eluted from the GSTcJun(Ch) and GSTvJun beads and analyzed for its ability to phosphorylate c-Jun in solution, as described for FIG. 6. While chicken GSTcJun bound the kinase as efficiently as human GSTcJun, GSTvJun was defective in JNK binding (FIGS. 7B, C).

EXAMPLE 8

JNK Binding is Required for Ha-Ras and UV Responsiveness

Figure 8A:
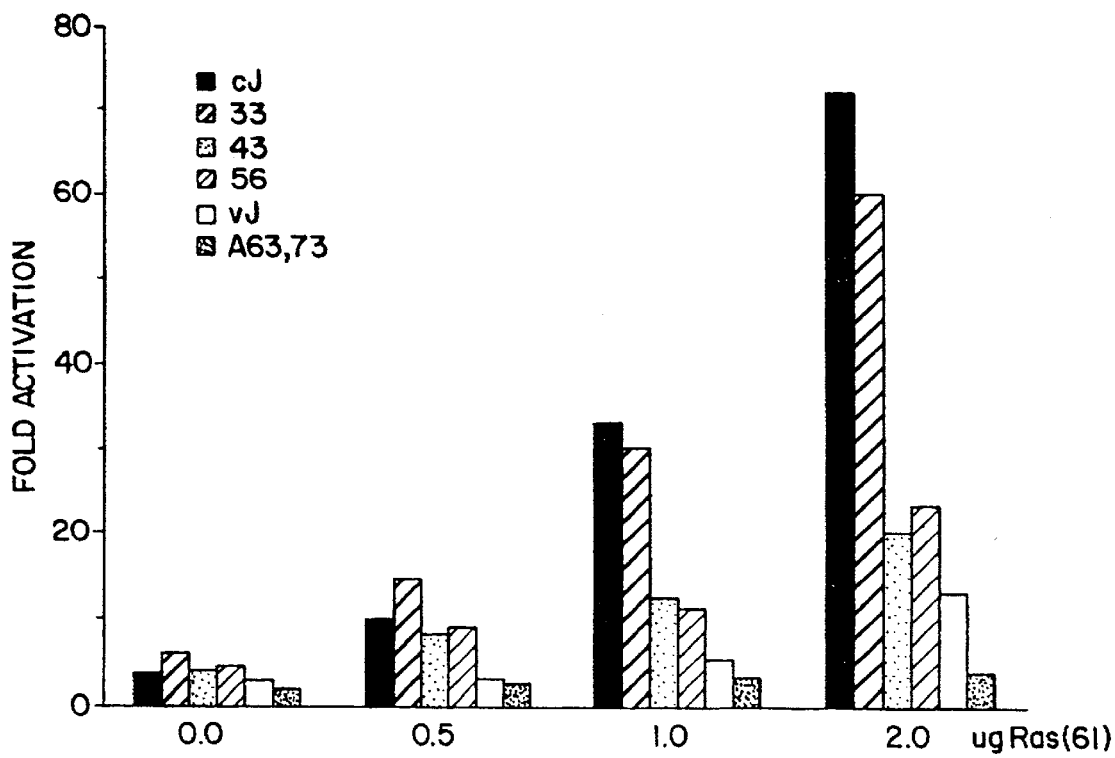
FIG. 8 shows CAT activity in cells containing various portions of the c-Jun activation domain (cJ=AA1-223; 33=AA33-223; 43=AA43-223; 56=AA56-223; A63,73= AA1-246(Ala63/73)) and a CAT reporter in the absence or presence of A) Ha-ras or B) UV treatment.

Phosphorylation of Ser 63 and 73 is necessary for potentiation of c-Jun mediated transactivation by Ha-Ras (Smeal, et al., supra, 1991). If binding of JNK has any role in this response, mutations that decrease kinase binding in vitro should attenuate the stimulation of c-Jun activity by Ha-Ras in vivo. This relationship was examined by cotransfection assays. Expression vectors were constructed to express chimeric GAL4-cJun and GAL4-vJun proteins, that consist of the DNA binding domain of the yeast activator GAL4 (Sadowski and Ptashne, 1989) and N-terminal sequences of c-Jun or v-Jun. The ability of these chimeras to activate the GAL4-dependent reporter 5×GAL4-Elb-CAT (Lillie and Green, 1989) was examined in the absence or presence of a cotransfected Ha-Ras expression vector (FIG. 8A). F9 cells were cotransfected with 1.0 µg of expression vector encoding the indicated GAL4-cJun chimeric proteins containing various portions of the c-Jun activation domain [cJ=AA1-223; 33-AA33-223; 56=AA56-223; A63, 73=AA1-246 (Ala63/73)] and 2.0 µg of a 5×GAL4-Elb-CAT reporter in the absence or presence of the indicated amounts (in µg) of pZIPNeoRas(Leu61). The total amount of expression vector was kept constant and the total amount of transfected DNA was brought to 15 µg using pUC18 and the appropriate amount of pZIPneo. Cells were harvested 28 hours after transfection and CAT activity was determined. Shown are the averages of two experiments, calculated as foldactivation over the level of reporter expression seen in the absence of the GAL4-Jun expressions vectors.

Figure 8B:
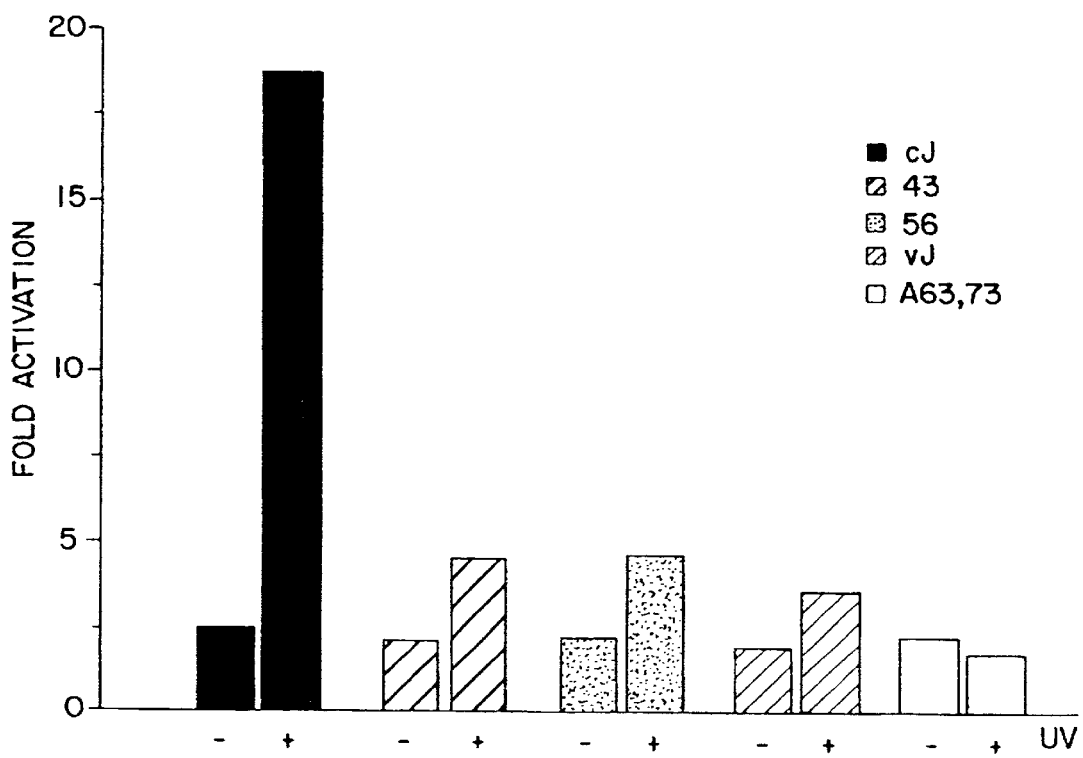

While deletion of AA 1–32 of c-Jun resulted in a small decrease in Ha-Ras responsiveness (9.8-fold induction vs. 19-fold induction for wt GAL4-cJun), deletion of AA 1–42 or 1–55 resulted in a greater decrease in Ha-Ras responsiveness (5.2-fold induction). A similar decrease in Ha-Ras responsiveness was observed upon substitution of c-Jun sequences with v-Jun sequences (4.7-fold induction). In fact, the GAL4-cJun(56-223) and GAL4-vJun chimeras were only 2-fold more responsive than GAL4-cJun(1-246;Ala63/73) in which Ser 63 and 73 were converted to alanines. That chimera exhibited only a marginal response (2-fold) to Ha-Ras. The same set of GAL4-cJun and GAL4-vJun fusion proteins was tested for UV responsiveness. F9 cells were transfected as described above except that instead of cotransfection with pZIPNeoRas, the cells were either exposed or not exposed to 40 J/m2 of UV-C 8 hours after transfection. The cells were harvested and assayed for CAT activity 20 hours later. FIG. 8B shows the averages of two experiments calculated as described above.

As shown in FIG. 8B, those proteins incapable of binding JNK in vitro, were non-responsive to UV in vivo. While the activity of GAL4-cJun(43-223) was stimulated 7.5-fold by UV, the activities of GAL4-cJun(43-233), GAL4-cJun(56-223) and GAL4-vJun were induced only 1.5-fold.

To reveal the role of JNK binding in c-Jun phosphorylation, F9 cells were transfected with c-Jun and v-Jun expression vectors in the absence or presence of an activated Ha-Ras expression vector. UV-irradiation was also used to activate the Ha-Ras pathway (Devary, et al., 1992). v-Jun and c-Jun were isolated by immunoprecipitation from $^{32}$S- or $^{32}$P-labelled F9 cells that were transfected with v-Jun and c-Jun expression vectors in the absence or presence of pZIPNeoRas (Leu61). The isolated proteins were analyzed by SDS-PAGE and autoradiography. Shown are the results of one typical experiment for each protein. Note that the $^{32}$P-labelled v-Jun autoradiogram was exposed 3 times longer than the corresponding c-Jun autoradiogram to generate signals of similar intensity. v-Jun and c-Jun were isolated from $^{32}$P and $^{32}$S-labelled F9 cells that were transfected with v-Jun or c-Jun expression vectors. One half of the cells were irradiated with UV-C(40 J/m$^2$) for 30 minutes prior to isolation of the Jun proteins by immunoprecipitation. In this case, the c-Jun and v-Jun lanes represent equal autoradiographic exposures. The two arrowheads indicate the migration positions of the two forms of c-Jun (Devary, et al., 1992), whereas the square indicates the migration position of v-Jun.

Figure 9A:
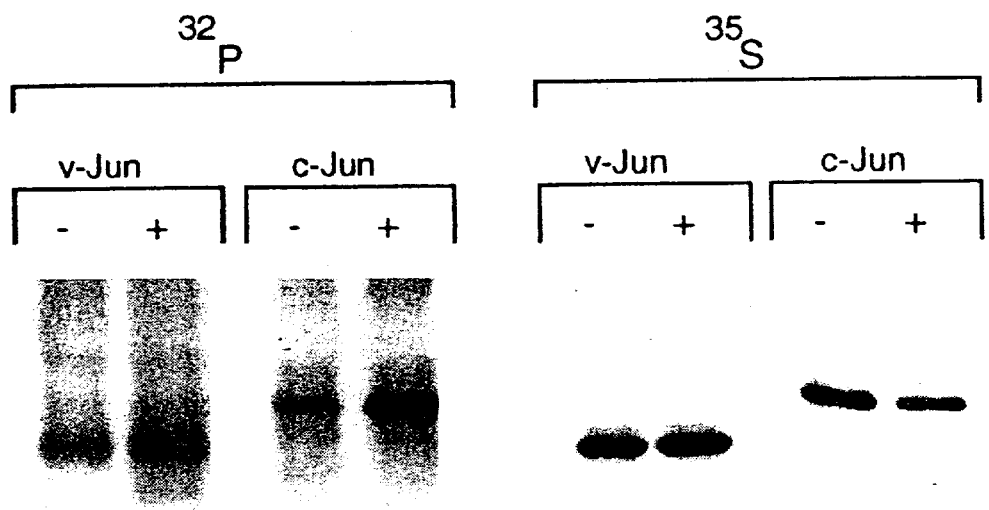
FIG. 9 shows SDS-PAGE analyses of $^{32}$P and $^{35}$S labelled F9 cells transfected with v-Jun and c-Jun in the absence or presence of A) Ha-ras or B) UV exposure.
Figure 9B:
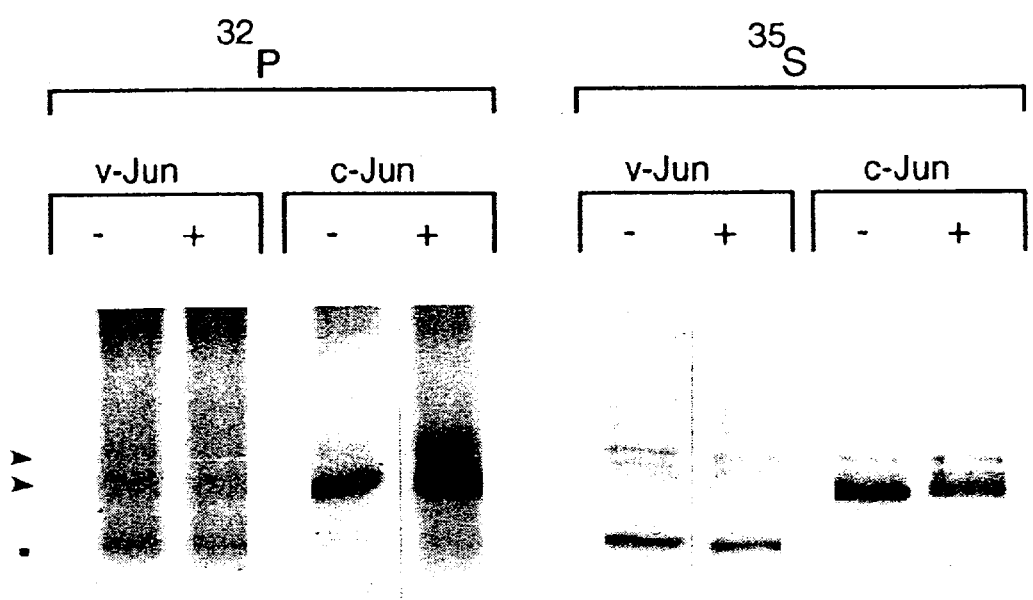

Immunoprecipitation from $^{32}$S-labelled cells showed that c-Jun and v-Jun were expressed at similar levels and that their expression level was not affected by either Ha-Ras (FIG. 9A) or UV (FIG. 9B). Immunoprecipitation from $^{32}$P-labeled cells indicated that both Ha-Ras and UV stimulated the phosphorylation of c-Jun, whereas the phosphbrylation of v-Jun, whose basal level was several-fold lower than that of c-Jun, was not enhanced by either treatment. As observed previously (Devary, et al., supra, 1991), UV was a stronger inducer of c-Jun phosphorylation resulting in its retarded electrophoretic mobility. Phosphopeptide mapping confirmed that Ha-Ras expression had a much smaller effect on the phosphorylation of v-Jun in comparison to its effect on c-Jun. As shown previously (Smeal, et al., supra, 1991), v-Jun was phosphorylated only on one site which is equivalent to Ser 73 of c-Jun.

EXAMPLE 9

Antisera and Proteins c-Jun polyclonal antiserum was described by Binetruy, et al., (Nature, 351:122—127, 1991). The anti-CD3 monoclonal antibody OKT3 (Van Wauwe, et al., J. Immunol., 124:2708–2713, 1980) was obtained from Dr. Amnon Altman, La Jolla Institute for Allergy and Immunology, and the anti-CD28 monoclonal antibody 9.3 is described in Hansen, et al., (Immunogenetics, 10:247–260, 1980). The anti-ERK2 and anti-ERK antibodies were provided by Drs. M. Weber and M. Cobb (University of Texas Southwestern), respectively. Expression and purification of GST-cJun(1-223) was described (Hibi, et al., Genes & Dev., 7:2135, 1993). The bacterial expression vector for kinase-defective ERK-1 was a gift from Dr. M. Cobb and the recombinant protein was prepared and purified by Dr. J. Hagstrom. MBP was purchased from Sigma.

Cell Culture, Metabolic Labeling, and Immunoprecipitation

Jurkat cells were grown in RPMI with 10% fetal calf serum (FCS), 1 mM glutamate, 100 μ/ml penicillin (pen), 100 μg/ml streptomycin (strep) and 250 ng/ml amphotericin (complete medium). HeLa S3, CV-1 and FR3T3 cells were grown in DMEM supplemented with 10% FCS, 100 μ/ml pen, 100 μg/ml strep. All cells were cultured at 37° C. with 5% $CO_2$. Mouse thymocytes were prepared from 8 week old Balb/C mice by gradient centrifugation on lymphocyte separation medium (Pharmacia). The lymphocytes were cultured for 5 hours at 37° C. in RPMI+10% FCS, prior to stimulation. Jurkat cells were labelled for 90 minutes with 0.5 mCi/ml $^{32}$P-orthophosphate (ICN Radiochemicals) in medium lacking sodium phosphate. Labelled cells were treated with TPA (Sigma) and A23187 (Calbiochem) 1 μg/ml as indicated. When used, cyclosporin A (CsA) (Sandoz) 100 ng/ml in ethanol was added 10 minutes prior to cell stimulation. Following stimulation, the labelled cells were washed twice with ice-cold PBS then lysed with RIPA buffer (10 mM Tris pH 7.5, 150 mM NaCl, 2 mM EDTA, 1% Triton-X 100, 1% DOC, 0.1% SDS) supplemented with phosphatase inhibitors (20 mM β-glycerophosphate, 10 mM p-nitrophenylphosphate, 1 mM $Na_3$ $VO_4$), and protease inhibitors (10 μg/ml leupeptin, aprotonin, pepstatin and 1 mM phenylmethyl sulfonylfluoride). c-Jun was immunoprecipitated as described (Binetruy, et al., supra., 1992) and analyzed by SDS-PAGE, followed by peptide mapping (Boyle, et al., Cell, 64:573–584, 1991; Lin, et al. Cell, 70:777–789, 1992). Ha-Ras was immunoprecipitated with Y13-259. Ha-Ras bound nucleotides were extracted and analyzed as described by Satoh, et al., (Proc. Natl. Acad. Sci., USA, 15:5993–5997, 1990).

RNA Extraction and Northern Blot Analysis

Exponentially growing Jurkat cells ($10^6$/ml) grown in complete RPMI medium was pretreated with CsA for 15 minutes when applicable, then subjected to various treatments for another 40 minutes. Total cytoplasmic RNA was extracted as previously described (Angel, et al., Cell, 49:729–739, 1987). 10 μg RNA was denatured by incubating with glyoxal for 60 minutes at 55° C. and fractionated on a 1% agarose gel in phosphate buffer. The fractionated RNA was blotted to Zetabind Nylon membrane (CUNO Labs) and hybridized to $^{32}$P-labelled cDNA probes specific for c-jun, jun-B, jun-D, c-fos, α-tubulin and IL-2.

Protein Kinase Assays

Exponentially growing cells were stimulated for the indicated times and hypotonic detergent cellular extracts were prepared as described (Hibi, et al., Genes and Dev., supra, 1993). The solid-state phosphorylation assay for measuring JNK activity was performed by incubated extracts with GSTcJun(1-223)-GSH agarose beads as described (Hibi, et al., supra., 1993) and as in Example 2. ERK1 and 2 activity was assayed by an immunecomplex kinase assay using MBP as a substrate (Minden, et al., Nature, 1993).

Reporters, Expression Vectors and Transfections

−79 jun-LUC, −73/+63 Col-LUC, −60/+63 Col-LUC were described previously (Deng and Karin, 1993). The IL2-LUC reporter plasmid was constructed by subcloning the IL-2 promoter (298 bp) from IL2CAT/+1 (Serfling, et al., EMBO J., 8:465–473, 1988) into the p20Luc vector (Deng and Karin, Genes and Dev., 7:479, 1993) between the SacI and KpnI site. The c-Jun expression vector pSRαIIc-Jun was constructed by subcloning the human c-jun HindIII-NotI fragment from pRSVc-Jun (Binetruy, et al., supra., 1991) into pSRαII vector by blunt end ligation. pBJ-CNA and pBJ-CNB were from Dr. G. Crabtree, Stanford University. β-Actin-LUC was from Dr. C. Glass, UCSD.

T Ag Jurkat cells, a derivative of the human Jurkat T-cell line stably transfected with the SV40 large T antigen (a gift from Dr. G. Crabtree) were grown to $10^6$/ml, then resuspended at $2\times10^7$/ml in fresh complete medium. $10^7$ cells (0.5 ml) were mixed with reporter plasmids (5 μg, −79 jun-LUC; 10 μg, −73/+63 Col-LUC or −60/+63 Col-LUC; 5 μg IL2-LUC) at room temperature for 10 minutes, then electroporated at 250 V, 960 uF in a 0.4 cm cuvette using a Bio-Rad GenePulser. After electroporation, cells were immediately put on ice for 10 minutes, then resuspended in 10 ml complete medium for 24 hours before stimulation. 0.5 μg of pSRαIIc-Jun were used to transfect $10^7$ Jurkat cells. Luciferase activity was determined as described (Deng and Karin, supra., 1993).

Analysis of GDP and GTP Bound to RAS p21

Jurkat cells $10\times10^6$ were labelled for 3 hours with $^{32}$P-orthophosphate (ICN Radiochemicals) at 1 mCi/ml in 5 mM of $Na_3VO_4$ phosphate-free DMEM supplemented with 1 mg/ml BSA. Before harvest, cells were stimulated with TPA, 10 ng/ml, A23187, 1 μg/ml anti-CD3 antibody (OKT3), 10 μg/ml, anti-CD28 antibody, 2 μg/ml or their combinations. After treatment for a specified period, cells were washed once immediately with ice cold PBS, twice with ice-cold Tris-Buffered saline (50 mM Tris-HCl, pH 7.5, 20 mM $MgCl_2$, 150 mM NaCl, 10.5% Nonidet P-40/1 μg/ml of aprotinin, leupeptin, pepstatin and 1 mM phenylmethyl sulfonylfluoride). Ras p21 was immunoprecipitated with monoclonal antibody Y 12-259 (Santa Cruz Biotechnology, Inc., Santa Cruz, Calif.). The GDP/GTP content of Ras was analyzed by TLC as described (Satoh, et al., Proc. Natl. Acad. Sci., USA, 15:5993, 1990) and quantitated with an Ambis radioanalytic image system (Ambis, San Diego, Calif.).

EXAMPLE 10

Synergistic Induction of AP-1 Activity During T Cell Activation

During the first stage of T lymphocyte activation, early response genes are rapidly included (Crabtree, Science, 243:355,361, 1989; Zipfel, et al., Mol Cell Bio., 9:1041–1048, 1989). Induction of jun and fos genes during activation of the Jurkat T cell line was investigated. Two different co-stimulatory paradigms were used, one employing TPA and the $Ca^{2+}$ ionophore A23187, and the second based on simultaneous stimulation of the TCR complex with an antibody to its CD3 component (OKT3; Van Wauwe, et al., J. Immunol., 124:2708–2713, 1980) and stimulation of the CD28 auxiliary receptor with an anti-CD28 antibody (9.3; Hansen, et al., Immunogenetics, 10:247–260, 1993; June, et al., Immunol. Today, 11:211–216, 1990). Total cytoplasmic RNA was extracted from Jurkat cells that were incubated with 50 ng/ml TPA (T), 1 μg/ml A23187 (A) or 100 ng/ml cyclosporin A (CsA) for 40 minutes, either alone or in combinations, as indicated. After fractionation of 10 μg samples on an agarose gel and transfer to nylon membrane, the level of c-jun, jun-B, jun-D, c-fos and α-tubulin expression was determined by hybridization to random primed cDNA probes.

Second, Jurkat cells were incubated with 10 μg/ml soluble anti-CD3 (OKT3), 2 μg/ml soluble anti-CD28 (9.3) or a combination of 50 ng/ml TPA and 1 μg/ml A23817 (T/A) as indicated for 40 minutes. Total cytoplasmic RNA was isolated and 10 μg samples were analyzed as described above using c-jun, jun-D and c-fos probes. IL-2 induction by the same treatments was measured after 6 hours of stimulation by blot hybridization using IL-2 and α-tubulin specific probes.

Both the first and second costimulatory paradigms induced IL-2 transcription (FIG. 11B). Optimal induction of c-jun also required a combined treatment with TPA and A23187 (FIG. 11A) or anti-CD3 and anti-CD28 (FIG. 11B). The synergistic induction of c-jun by both costimulatory paradigms was partially inhibited by CsA. jun-B was also induced by TPA, but its induction was not affected by A23187 or CsA. Although TPA+A23187 potentiated jun-D expression, this effect was also not inhibited by CsA. As reported by Matilla, et al., (EMBO J., 9: 4425–4433, 1990), maximal induction of c-fos also required treatment with TPA+A23187, but was not inhibited by CsA. Therefore sensitivity to CsA is unique to c-jun. While incubation with soluble anti-CD3 led to induction of c-jun and c-fos, only c-jun expression was augmented by simultaneous exposure to anti-CD28.

The effects of the different stimuli on AP-1 transcriptional activity in Jurkat cells were examined using a truncated, AP-1 responsive, human collagenase promoter (Angel, et al., Cell, 49:729–739, 1987) fused to the luciferase (LUC) reporter gene. Jurkat cells were transfected with 10 μg of either −73Col-LUC or −60Col-LUC reporter plasmids. 24 hours after transfection, the cells were aliquoted into 24 well plates and incubated for 9 hours with 50 ng/ml TPA, 1 μg/ml A23187 or 100 ng/ml CsA, either alone or in combinations, as indicated. The cells were harvested and luciferase activity was determined. The results shown are averages of three experiments done in triplicates.

Figure 11C:
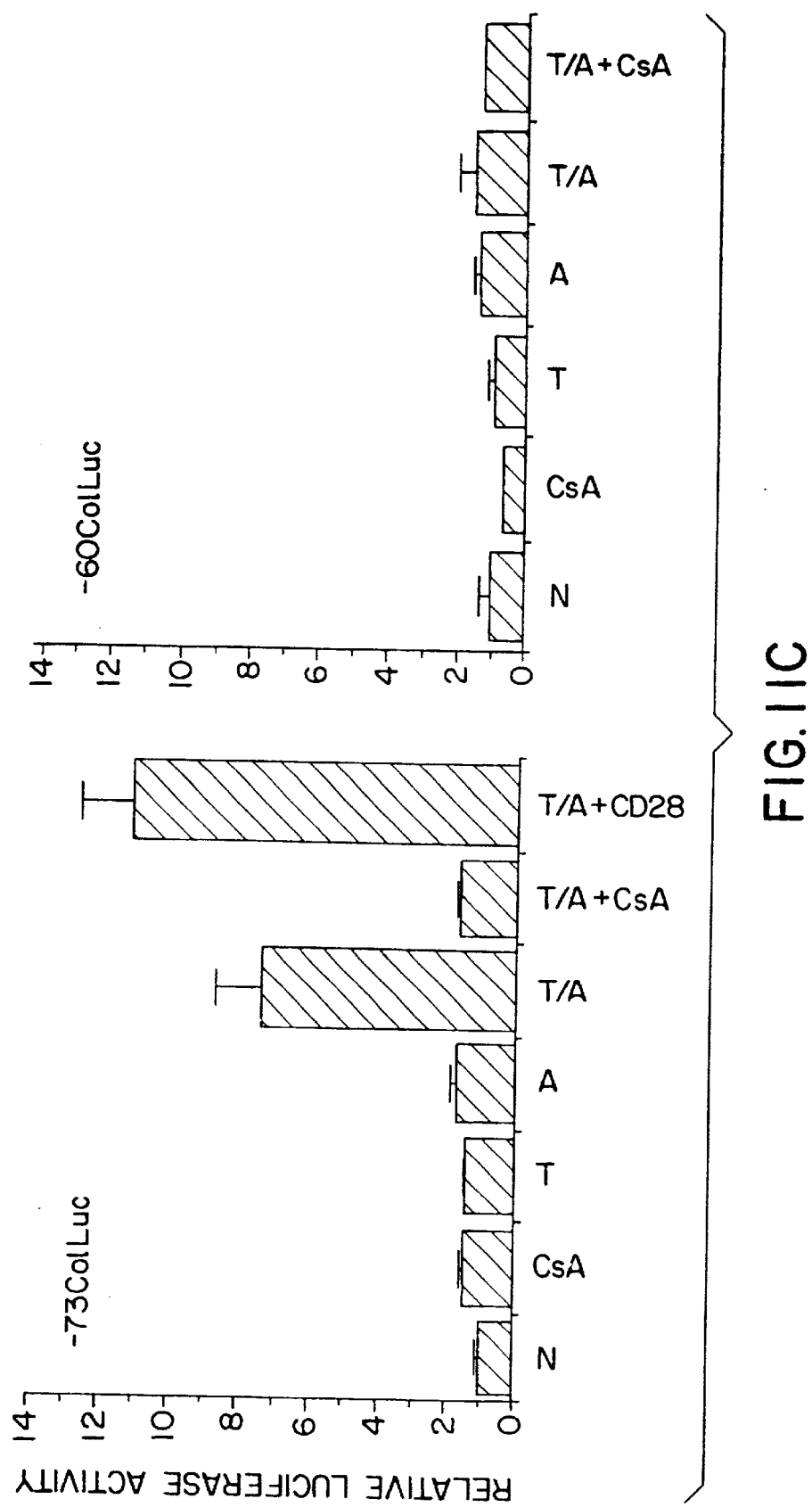
FIG. 11C shows Jurkat cells transfected with 10 µg of either −73Col-LUC or −60Col-LUC reporter plasmids. 24 hours after transfection, the cells were aliquoted into 24 well plates and incubated for 9 hours with 50 ng/ml TPA, 1 µg/ml A23187 or 100 ng/ml CsA, either alone or in combination, as indicated. The cells were harvested and luciferase activity was determined. The results shown are averages of three experiments done in triplicates.

While TPA and A23187 administered alone had marginal effects on −73Col-LUC, the two together resulted in its synergistic activation (FIG. 11C). The −60Col-LUC reporter, lacking an AP-1 binding site, was not induced. Induction of −73Col-LUC was inhibited by CsA. Treatment with anti-CD3 and anti-CD28 also resulted in synergistic activation of −73Col-LUC. Similar results were obtained with the AP-1 responsive c-jun promoter. These findings differ from previous measurements of AP-1 activity in Jurkat cells that relied on the use of synthetic promoters containing multiple AP-1 sites (Matilla, et al., supra, 1993; Ullman, et al., Genes & Dev., 7:188–196, 1993). While these findings were reproducible, previous studies indicate that the physiological collagenase and c-jun promoters provide a more accurate and valid measurement of AP-1 transcriptional activity. Indeed, the expression patterns of the collagenase and c-jun reporters are very similar to that of the c-jun gene.

EXAMPLE 11

Costimulation of c-Jun N-terminal Phosphorylation is Suppressed by CsA

Induction of c-Jun transcription and optimal stimulation of AP-1 correlate with changes in c-jun phosphorylation (Devary, et al., *Cell*, 71:1081–1091, 1992). The effect of TPA and A23187 on c-Jun phosphorylation in Jurkat cells was examined. To elevate c-Jun expression, Jurkat cells were transfected with a c-Jun expression vector. The cells were labelled with $^{32}$P and c-Jun was immunoprecipitated from cells subjected to various stimuli and analyzed by SDS-PAGE (FIG. 12A). Jurkat cells ($10^6$ cells per lane) were transfected with 0.5 µg of a SRα-cJun expression vector and 24 hours later were labeled for 3 hours with $^{32}$P-orthophosphate (1 mCi/ml). After 15 minutes, treatment with 50 ng/ml TPA (T), 1 µg/ml A23187 (A) and 100 ng/ml CsA, either alone or in combination, as indicated, the cells were lysed in RIPA buffer and c-Jun was isolated by immunoprecipitation and analyzed by SDS-PAGE. The c-Jun bands are indicated.

In unstimulated cells, phosphorylated c-Jun migrated as a single band. Treatment with TPA for 15 minutes induced the appearance of slower migrating bands and costimulation with A23187 enhanced this effect, while CsA reduced the $Ca^{++}$ effect. Within the short time frame of this experiment, there were minimal effects on c-Jun expression.

Figure 12C:
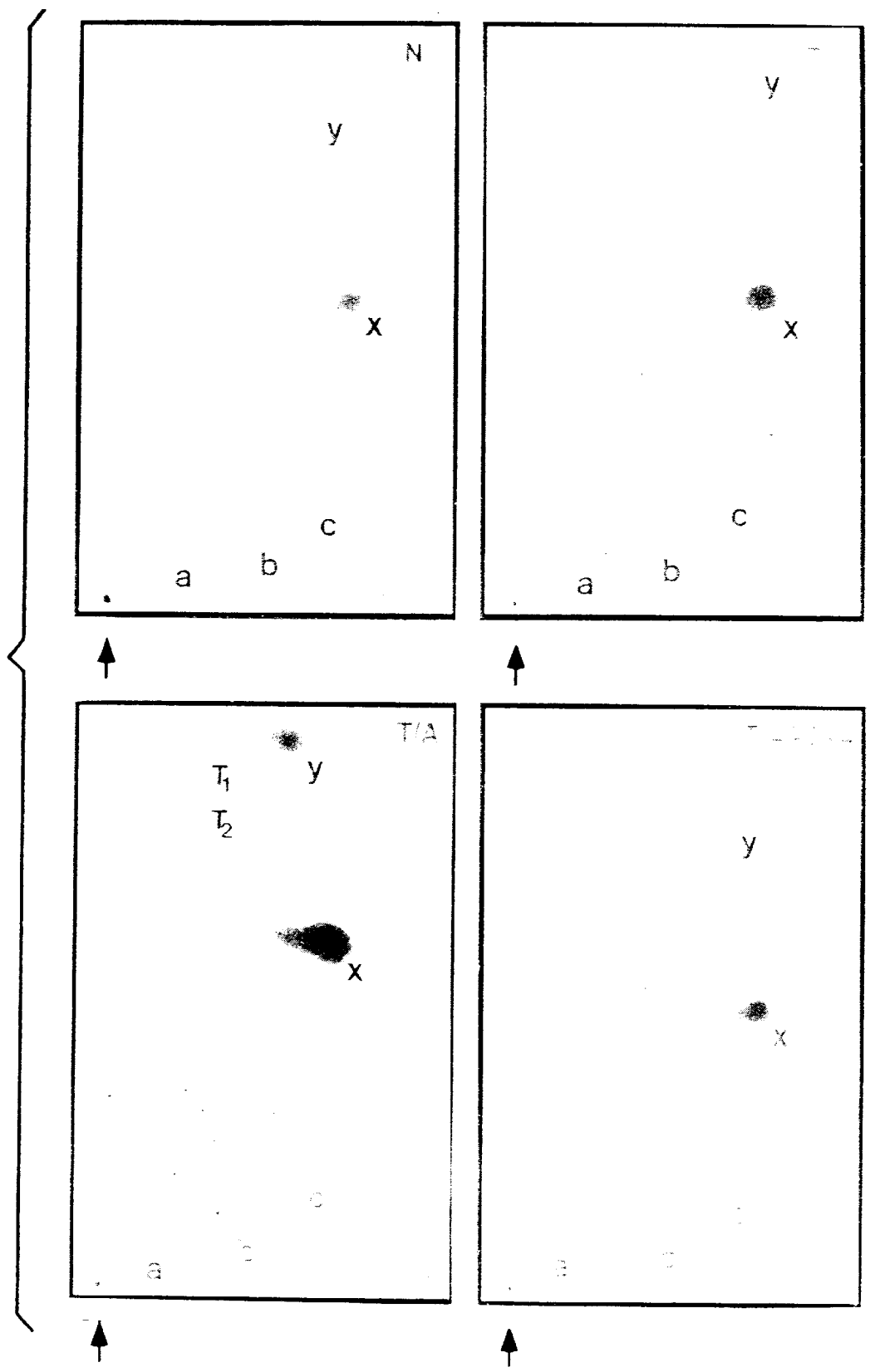
FIG. 12C shows all of the c-Jun specific protein bands shown in FIG. 12A isolated from equal numbers of cells excised from the gel and subjected to tryptic phosphopeptide mapping. Shown is a typical result (this experiment was repeated at least three times). N-nonstimulated cells; T-cells treated with 50 ng/ml TPA; T/A: cells treated with 50 ng/ml TPA and 1 µg/ml A23187; T/A+CsA: cells treated with T/A and 100 ng/ml CsA. a,b,c,x and y correspond to the various tryptic phosphopeptides of c-Jun, previously described by Boyle, et al., (*Cell*, 64:573–584, 1991) and Smeal, et al., (*Nature*, 354:494–496, 1991). T1 and T2 correspond to the minor phosphorylation sites; Thr91, 93 and 95 (Hibi, et al., *Genes & Dev.*, 7:000, 1993).

Similar results were obtained by analysis of endogenous c-Jun expression and phosphorylation (FIG. 12B). $2 \times 10^7$ Jurkat cells were labeled for 3 hours with either $^{35}$S-methionine (900 µCi/ml) or $^{32}$P-orthophosphate (1 mCi/ml). After 15 minutes incubation with 50 ng/ml TPA+1 µg/ml A23178 (T/A) in the absence or presence of and 100 ng/ml CsA or no addition, as indicated, the cells were lysed in RIPA buffer and c-Jun isolated by immunoprecipitation and analyzed by SDS-PAGE. The c-Jun band is indicated. However, due to lower expression levels, some of the slower migrating forms were not clearly visible.

c-Jun phosphorylation was further analyzed by two-dimensional phosphopeptide mapping (FIG. 12C). This analysis included all the isoforms of c-Jun. All of the c-Jun specific protein bands shown in FIG. 12A, isolated from equal numbers of cells, were excised from the gel and subjected to tryptic phosphopeptide mapping. Shown is a typical result (this experiment was repeated at least three times). N-nonstimulated cells; T-cells treated with 50 ng/ml TPA; T/A: cells treated with 50 ng/ml TPA and 1 µg/ml A23187; T/A+CsA: cells treated with T/A and 100 ng/ml CsA. a,b,c,x and y correspond to the various tryptic phosphopeptides of c-Jun, previously described by Boyle, et al., (*Cell*, 64:573–584, 1991) and Smeal, et al., (*Nature*, 354:494–496, 1991). T1 and T2 correspond to the minor phosphorylation sites; Thr91, 93 and 95 (Hibi, et al., *Genes & Dev.*, 7:000, 1993).

While the intensity of spot b, a doubly phosphorylated tryptic peptide containing the C-terminal phosphorylation sites of c-Jun (Boyle, et al., *Cell*, 64:573–584, 1991; Lin, et al., *Cell*, 70:777–789, 1992), was more or less invariant, TPA treatment resulted in a small increase in the intensity of the monophosphorylated form of this peptide (spot c) at the expense of the triple phosphorylated form (spot a). This effect was also observed in response to costimulation with TPA+A23187. In contrast to HeLa cells and fibroblasts (Boyle, et al., supra, 1991; Minden, et al., *Nature*, 1993), TPA treatment of Jurkat cells resulted in increased phosphorylation of the N-terminal sites, corresponding to Ser63 (spot y) and Ser73 (spot x) and this effect was strongly enhanced by A23187. CsA prevented the enhancement of N-terminal phosphorylation by A23187.

EXAMPLE 12

Synergistic Activation of JNK

Figure 13A:
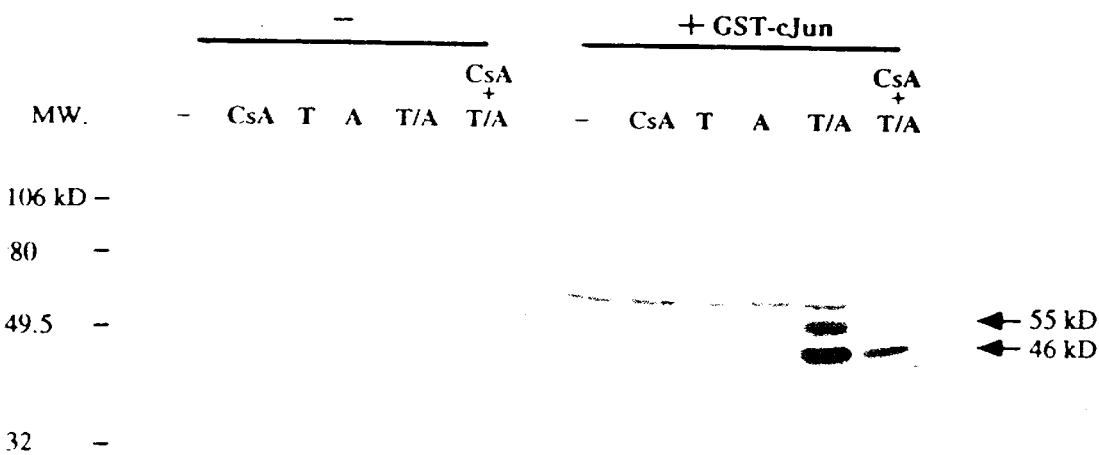
FIG. 13A shows whole cell extracts (WCE) of Jurkat cells incubated with TPA (T, 50 ng/ml), A23187 (A, 1 µg/ml) or CsA (100 ng/ml) for 15 minutes, alone or in combination, and separated by SDS-PAGE (100 µg protein/lane) on gels that were cast in the absence or presence of GST-cJun (1-223). The gels were subjected to renaturation protocol and incubated in kinase buffer containing γ-$^{32}$P-ATP. The protein bands corresponding to the 55 kD and 46 kD forms of JNK are indicated.

Studies were done to determine whether enhanced N-terminal c-Jun phosphorylation in response to TPA+ A23187 was due to synergistic activation of JNK, the protein kinase that binds to c-Jun and phosphorylates its N-terminal sites. JNK exists in two forms, 46 kD and 55 kD in size, both of which are activated by external stimuli (Hibi, et al., supra, 1993; Deng, et al., supra, 1993). In-gel kinase assays indicated that both forms of JNK were activated by TPA (FIG. 13A). Whole cell extracts (WCE) of Jurkat cells incubated with TPA (T, 50 ng/ml), A23187 (A, 1 µg/ml) or CsA (100 ng/ml) for 15 minutes, alone or in combination, were separated by SDS-PAGE (100 µg protein/lane) on gels that were cast in the absence or presence of GST-cJun (1-223). The gels were subjected to renaturation protocol and incubated in kinase buffer containing γ-$^{32}$P-ATP. The protein bands corresponding to the 55 kD and 46 kD forms of JNK are indicated.

While A23187 treatment by itself did not activate JNK, it potentiated its activation by TPA. CsA blocked this costimulatory effect.

Figures 13B, 13C:
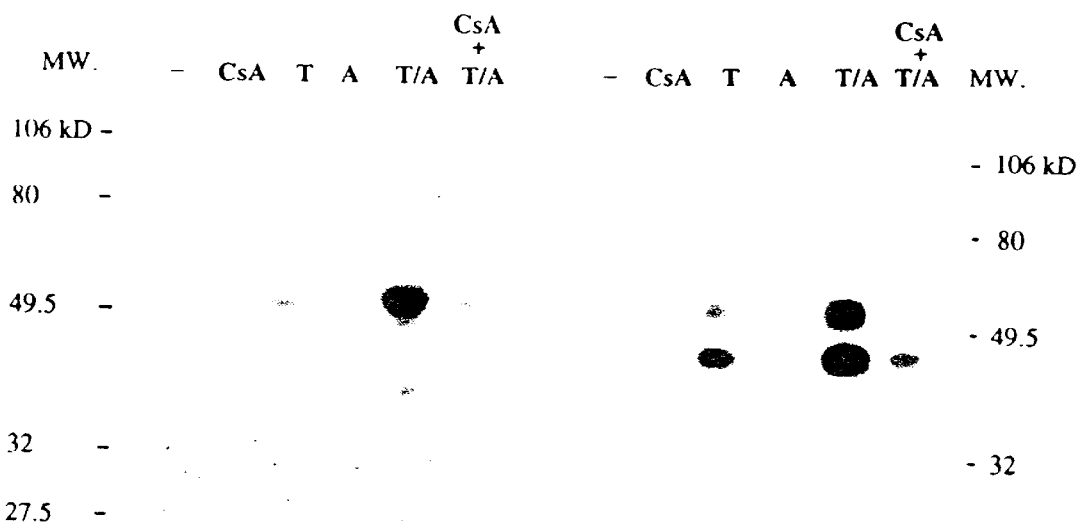
FIG. 13B shows WCE (50 µg) of Jurkat cells treated as described above were incubated with 5 µl of GSH agarose beads coated with 10 µg GST-cJun (1-223) for 12 hours at 4° C. After extensive washing, the beads were incubated in kinase buffer containing γ-$^{32}$P-ATP for 20 minutes at 30° C., after which the proteins were dissociated by incubation in SDS sample buffer and separated by SDS-PAGE. The 49 kD band corresponds to GST-cJun (1-223).
FIG. 13C shows WCE (200 μg) of Jurkat cells treated as described in FIG. 13A and incubated with GST-cJun(1-223)-GSH agarose beads. The bound fraction was eluted in SDS sample buffer and separated by SDS-PAGE on a gel containing GST-cJun(1-223). The gel was renatured and incubated in kinase buffer containing γ-$^{32}$P-ATP to label the JNK polypeptides.

JNK can be retained on GSTcJun-glutathione (GSH) agarose affinity resin and its kinase activity measured by phosphorylation of GSTcJun. WCE (50 µg) of Jurkat cells treated as described above were incubated with 5 µl of GSH agarose beads coated with 10 µg GST-cJun (1-223) for 12 hours at 4° C. After extensive washing, the beads were incubated in kinase buffer containing γ-$^{32}$P-ATP for 20 minutes at 30° C., after which the proteins were dissociated by incubation in SDS sample buffer and separated by SDS-PAGE (FIG. 13B). The 49 kD band corresponds to GST-cJun (1-223). The faster migrating bands are degradation products (Hibi, et al., supra, 1993).

This solid-state assay also indicated that TPA treatment resulted in activation of JNK, which was strongly potentiated by A23187, which by itself had no effect. This synergistic activation of JNK was inhibited by CsA (FIG. 13B). To prove that the solid-state assay measures the activity of the same polypeptides identified by the in-gel kinase assay, JNK was first isolated on GSTcJun-GSH agarose beads and then analyzed it by an in-gel kinase assay. Both the 55 and 46 kD forms of JNK bound to GSTcJun and were regulated in the same manner revealed by the binding assay (FIG. 13C) WCE (200 µg) of Jurkat cells treated as described in FIG. 13A were incubated with GST-cJun(1-223)-GSH agarose beads as described above and the bound fraction was eluted in SDS sample buffer and separated by SDS-PAGE on a gel containing GST-cJun(1-223). The gel was renatured and incubated in kinase buffer containing γ-$^{32}$P-ATP to label the JNK polypeptides.

EXAMPLE 13

Costimulation by $Ca^{++}$ is Unique to JNK and T Lymphocytes

We examined whether elevated intracellular $Ca^{++}$ affects JNK activation in other cells. JNK activity was weakly stimulated by TPA in CV1 and FR3T3 cells, but not in PC12 cells (FIG. 14). Cultures of FR3T3, CV-1, PC12 and mouse thymocytes were incubated for 15 minutes in the presence of TPA (50 ng/ml, T), A23817 (1 µg/ml, A) and/or CsA (100 ng/ml), as indicated. WCE prepared from $2-4 \times 10^5$ cells for the established cell lines and $1.5 \times 10^6$ cells for primary thymocytes were incubated with GSTcJun(1-223)-GSH agarose beads. After washing, JNK activity was determined by solid-state phosphorylation assay as described above.

In none of these cells was JNK activity affected by A23187 or CsA treatment. Similar results were obtained in HeLa, HepG2 and Gc cells. By contrast, the regulation of JNK activity in mouse thymocytes was similar to that observed in Jurkat cells. TPA induced a moderate increase in JNK activity which was enhanced by A23187 and that costimulation was inhibited by CsA (FIG. 14).

JNK is a proline-directed protein kinase activated by extracellular stimuli (Hibi, et al., supra, 1993). In that respect, it resembles the ERK1 and 2 MAP kinases (Boulton, et al., *Cell*, 65:663–675, 1991). Since ERK1 and 2 appear to be involved in induction of c-fos (Gille, et al., *Nature*, 358:414–417, 1992; Marais, et al., *Cell*, 73:381–393, 1993) and could thereby participate in T cell activation, their regulation was examined. ERK1 and ERK2 activities were measured in both Jurkat and mouse thymocytes using an immunecomplex kinase assay and myelin basic protein (MBP) as a substrate. Recombinant, kinase-defective ERK1 was also used a substrate for assaying MEK, the protein kinase responsible for activation of ERK1 and 2 (Crews, et al., *Science*, 258:478–480, 1992). Both ERK and MEK activities were fully stimulated by TPA treatment of either Jurkat cells or mouse thymocytes (FIG. 15).

WCE (5 µg) of Jurkat (FIG. 15, panel A) or mouse thymocytes (panel C) were incubated with 1 µg of kinase-defective ERK1 in kinase buffer containing $\gamma$-$^{32}$P-ATP for 20 minutes. The phosphorylated proteins were separated by SDS-PAGE and the band corresponding to the mutant ERK1 is indicated. WCE (20 µg) of Jurkat (panel B) or mouse thymocytes (panel C) that were treated as described above were immunoprecipitated with anti-ERK antibodies (a gift from Dr. M. Weber). The immune complexes were washed and incubated in kinase buffer containing $\gamma$-$^{32}$P-ATP and 2 µg MBP for 15 minutes at 30° C. The phosphorylated proteins were separated by SDS-PAGE. The band corresponding to phosphorylated MBP is indicated. A23187 and CsA had no effect on either activity.

EXAMPLE 14

Synergistic Activation of JNK by Anti-CD3 and Anti-CD28

If JNK plays a central role in signal integration during T cell activation, then other costimulatory paradigms should also cause its synergistic activation. The regulation of JNK in response to T cell activation with anti-CD3 and anti-CD28 antibodies was examined. Jurkat cells (1×10$^7$) were incubated for 15 minutes with either normal mouse serum, 1 µg/ml anti-CD3 and/or 2 µg/ml anti-CD28, in the absence or presence of 100 ng/ml CsA, as indicated. WCE were prepared and 100 µg samples were analyzed for JNK activation using the in-gel kinase assay, as described above.

Figure 16A:
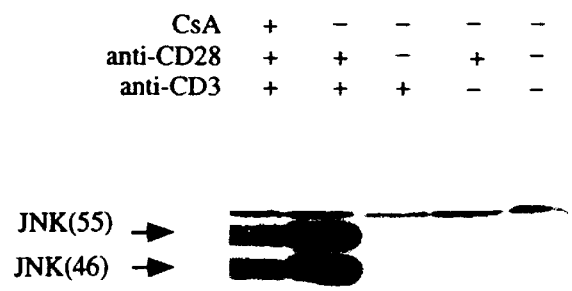
FIG. 16A shows Jurkat cells (1×10$^7$) incubated for 15 minutes with either normal mouse serum, 1 μg/ml anti-CD3 and/or 2 μg/ml anti-CD28, in the absence or presence of 100 ng/ml CsA, as indicated. WCE were prepared and 100 μg samples were analyzed for JNK activation using an in-gel kinase assay.

While incubation of Jurkat cells with either soluble anti-CD3 or soluble anti-CD28 alone had a negligible effect on JNK activity, simultaneous incubation with both antibodies resulted in strong synergistic activation of both forms (FIG. 16A).

Figure 16B:
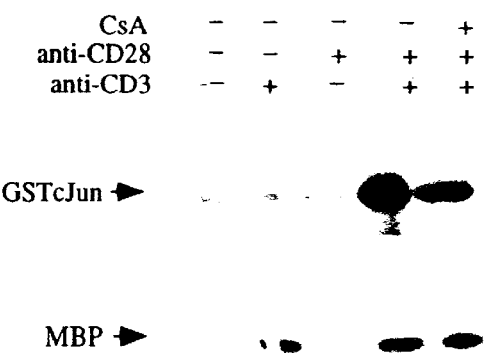
FIG. 16B shows WCE (50 μg) of Jurkat cells treated as described for FIG. 16A incubated with GSTcJun(1-223)-GSH agarose beads and assayed for JNK activity using the solid-state kinase assay. The same WCE (20 μg) were immunoprecipitated with anti-ERK2 antibodies and assayed for MBP-kinase activity.

WCE (50 µg) of Jurkat cells treated as described above were incubated with GSTcJun(1-223)-GSH agarose beads and assayed for JNK activity using the solid-state kinase assay. The same WCE (20 µg) were immunoprecipitated with anti-ERK2 antibodies and assayed for MBP-kinase activity. CsA partially attenuated this effect. By contrast, incubation with soluble anti-CD3 was sufficient for efficient activation of ERK2, which was not enhanced by costimulation with anti-CD28, nor was it inhibited by CsA (FIG. 16B).

Figure 16C:
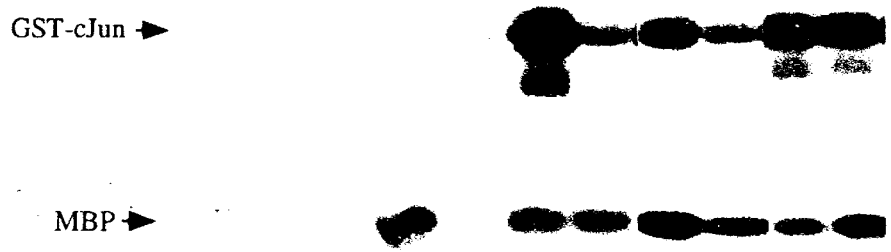
FIG. 16C shows WCE (50 μg) of Jurkat cells treated as described in FIG. 16A with various stimuli alone or their combinations were incubated with GSTcJun(1-223)-GSH agarose beads and assayed for JNK activity using solid-state kinase assay. The same samples (20 μg) were also assayed for MBP-kinase activity as described in FIG. 16B.

To further investigate the nature of signal integration by JNK, the effect of a suboptimal dose of TPA was examined, which by itself does not lead to JNK activation on the responses to either anti-CD3 or anti-CD28 (FIG. 16C). WCE (50 µg) of Jurkat cells treated as described in Panel A with various stimuli alone or their combinations were incubated with GSTcJun(1-223)-GSH agarose beads and assayed for JNK activity using solid-state kinase assay. The same samples (20 µg) were also assayed for MBP-kinase activity as described in FIG. 16B.

Together with A23187, this suboptimal dose of TPA resulted in a strong synergistic activation of JNK but not ERK2. The activation of JNK was completely inhibited by CsA. The suboptimal dose of TPA also led to strong synergistic activation of JNK together with either anti-CD3 or anti-CD28. ERK2, on the other hand, was fully activated by anti-CD3 and suboptimal TPA, which by itself led to partial activation of ERK2, had no further effect. Exposure to anti-CD28 did not augment the activation of ERK2 by TPA. JNK was also efficiently activated by combined treatment with anti-CD3 +A23187, but not by anti-CD28+A23187.

EXAMPLE 15

Activation of Ha-Ras

The effects of the various treatments on Ha-Ras activation were examined and the results shown in FIG. 17. Jurkat cells (2×10$^6$ cells per point) labeled with 0.4 mCi of $^{32}$P-orthophosphate for 3 hours were incubated with nonspecific antibody (1 µg/ml mouse IgG; control), 1 µg/ml anti-CD3, 2 µg/ml anti-CD28, 10 ng/ml TPA or 500 ng/ml A23187 (A), as indicated. After 2 minutes, the cells were harvested, lysed and Ha-Ras was isolated by immunoprecipitation. The guanine nucleotide bound to Ha-Ras were extracted, separated by thin layer chromatography and quantitiated as described in EXAMPLE 9. The values shown represent the averages of two separate experiments done in duplicates. Jurkat cells were labeled with $^{32}$P-orthophosphate and stimulated with either TPA or anti-CD3 as described above. At the indicated time points, the cells were harvested and the GTP content of Ha-Ras was determined as described directly above.

Figure 17A:
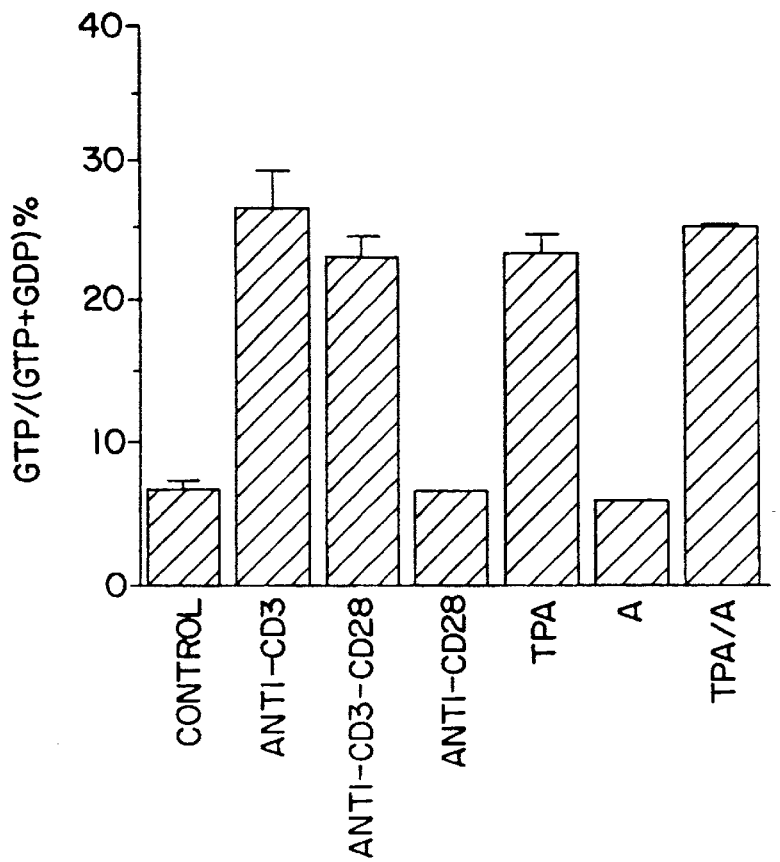
FIG. 17A shows Jurkat cells (2×10$^6$ cells per point) labeled with 0.4 mCi of $^{32}$P-orthophosphate for 3 hours and incubated with nonspecific antibody (1 μg/ml mouse IgG; control), 1 μg/ml anti-CD3, 2 μg/ml anti-CD28, 10 ng/ml TPA or 500 ng/ml A23187 (A), as indicated. After 2 minutes, the cells were harvested, lysed and Ha-Ras was isolated by immunoprecipitation. The guanine nucleotide bound to Ha-Ras was extracted, separated by thin layer chromatography and quantitiated. The values shown represent the averages of two separate experiments done in duplicates.
Figure 17B:
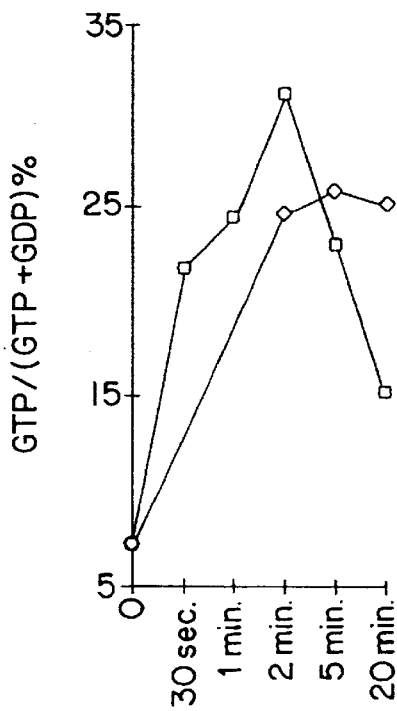
FIG. 17B shows Jurkat cells labeled with $^{32}$P-orthophosphate and stimulated with either TPA or anti-CD3. At the indicated time points, the cells were harvested and the GTP content of Ha-Ras was determined.

Whereas an optimal dose of TPA and exposure to soluble anti-CD3 led to activation of Ha-Ras, measured by an increase in its GTP content, soluble anti-CD28 had no effect on Ha-Ras activity (FIG. 17A). The activation of Ha-Ras by either anti-CD3 or TPA was not augmented by costimulation with either anti-CD28 or A23187, respectively. While the activation of Ha-Ras by TPA persisted for at least 20 minutes, the response to soluble anti-CD3 was highly transient (FIG. 17B). Therefore, signal integration must occur downstream of Ha-Ras.

EXAMPLE 16

Cloning of JNK1 Polynucleotide (46 kD)

To identify novel members of the MAP kinase group, a polymerase chain reaction (PCR) strategy was employed using degenerate primers to amplify sequences from a human liver cDNA library.

cDNA Cloning

Figure 18A:
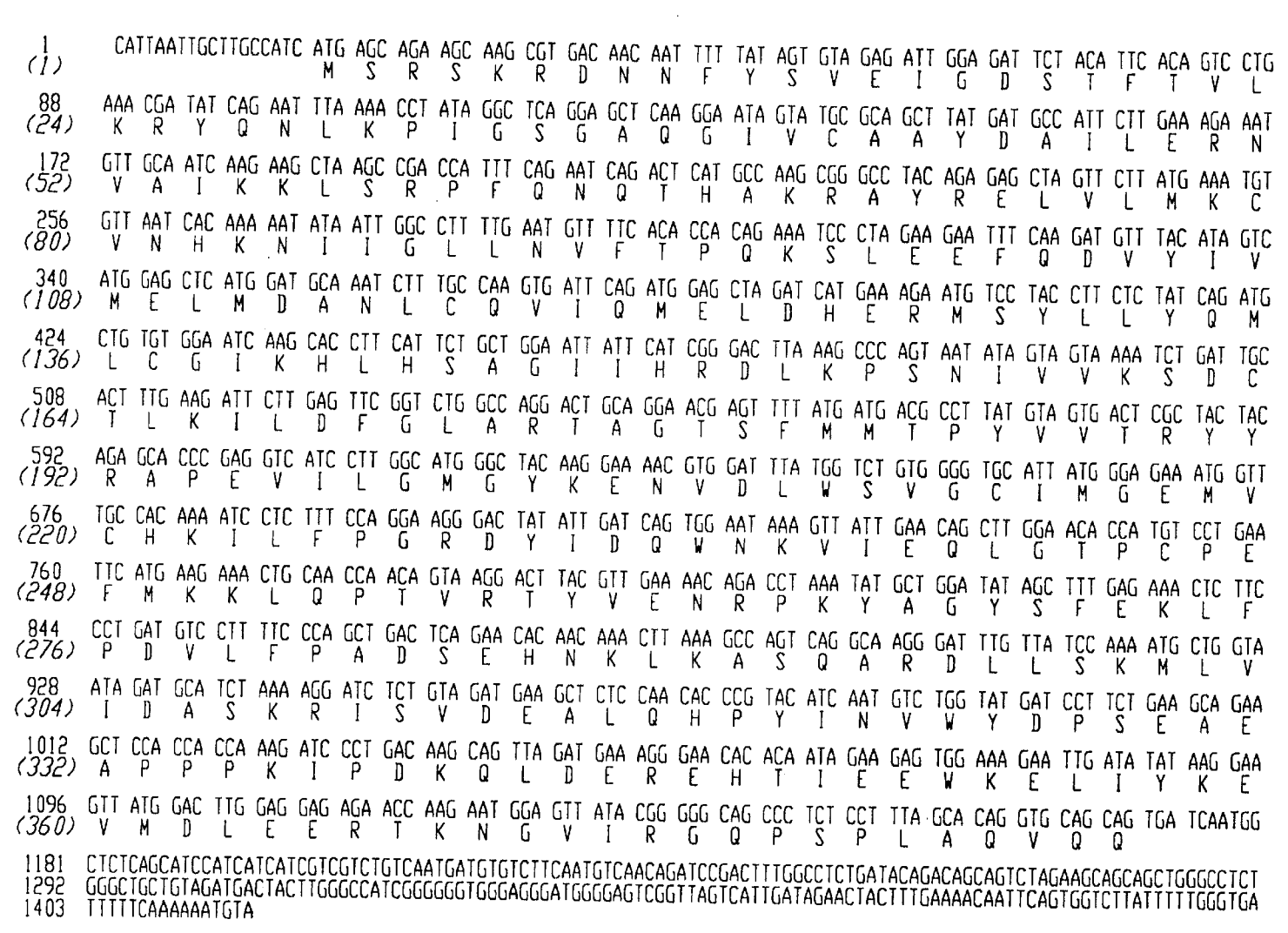
Figure 18B:
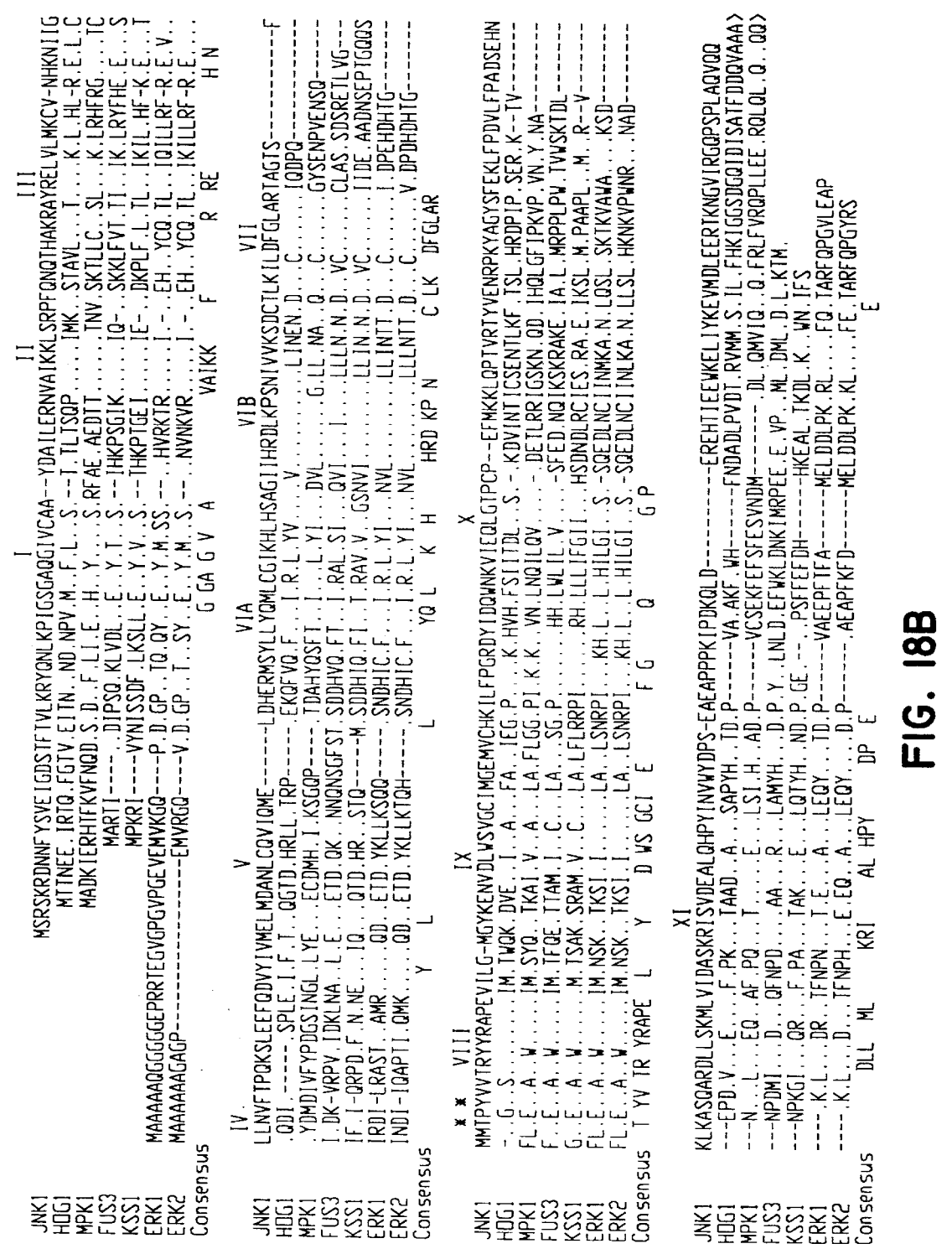

Degenerate oligonucleotides CAYMGNGAYNT-NAARCC (SEQ ID NO: 13) and GAGAGCCCATNSWC-CADATR TC (SEQ ID NO: 14) were designed based on conserved kinase sub-domains and employed as PCR primers to isolate fragments of MAP kinase-related cDNAs from a human liver cDNA library. Comparison of the sequence of 387 clones with the GenBank database (Blast Fileserver, National Center for Biotechnology Information) allowed identification of one clone that exhibited a high level of homology with members of the MAP kinase family. This partial cDNA was used to screen a λZapI human fetal brain cDNA library (Stratagene Inc., La Jolla, Calif.). Three positive clones were obtained after screening 10⁶ phage. DNA sequencing of both strands of each clone was performed using a PCR procedure employing fluorescent dideoxynucleotides and a model 373A automated sequencer (Applied Biosystems). This analysis demonstrated that these clones corresponded to overlapping cDNAs. The sequence of the largest clone (1418 bp) includes the complete JNK1 coding region and is shown in FIGS. 18A and D. A single long open reading frame that encodes a putative protein kinase, JNK1, with a predicted mass of 44.2-kDa was identified. In-frame stop codons in the 5' and 3' regions of the cDNA indicate that this clone contains the entire JNK1 coding region. FIG. 18B shows a comparison of the deduced sequence of JNK1 with other MAP kinases.

The deduced sequence of JNK1 is aligned with those of the MAP kinases HOG1 (Brewster, et al., *Science* 259:1760–1763, 1993), MPK1 (Torres, et al., *Mol. Microbiol.* 5:2845–2854, 1991; Lee, et al., *C. Mol. Cell. Biol.* 13:3067–3075, 1993), FUS3 (Elion, et al., *Cell* 60:649–664, 1990), KSS1 (Courchesne, et al., *Cell* 58:1107–1119, 1989), ERK1 (Boulton, et al., *Science* 249:64–67, 1990) and ERK2 (Boulton, et al., *Cell* 65:663–675, 1991) using the PILEUP program (Wisconsin Genetics Computer Group). Gaps in the sequences that were introduced to optimize the alignment are illustrated with a dash (–). Residues that are identical are indicated with a period (.). The carboxyl termini of HOG1 and MPK1 that extend beyond the kinase domain are truncated (>). The protein kinase sub-domains located within the deduced protein sequence are illustrated and the conserved tyrosine and threonine phosphorylation sites (*) are indicated with asterisks (Davis, *J. Biol. Chem* 268:14553–14556, 1993).

Comparison of the deduced structure of JNK1 with the Genbank data-base (Blast Fileserver, National Center for Biotechnology Information) revealed homology to the MAP kinases ERK1 (Boulton, et al., *Science* 249:64–67, 1990) and ERK2 (Boulton, et al., *Cell* 65:663–675, 1991). Sequence homology was also observed between JNK and the yeast MAP kinases HOG1 (Brewster, et al., *Science* 259:1760–1763,1993), MPK1 (Torres, et al., *Mol. Microbiol.* 5:2845–2854, 1991; Lee, et al., *C. Mol. Cell. Biol.* 13:3067–3075, 1993), FUS3 (Elion, et al., *Cell* 60:649–664, 1990), and KSS1 (Courchesne, et al, *Cell* 58:1107–1119, 1989). Significant regions of identity between JNK1 and other MAP kinases are found throughout the protein kinase domain. Notably, the Thr and Tyr phosphorylation sites located in sub-domain VIII, that are required for MAP kinase activation (Payne, et al., *EMBO J.* 10:885–892, 1991), are conserved in JNK1. Together, these sequence similarities indicate that JNK1 is a distant relative of the MAP kinase group (FIG. 18C).

Figure 18C:
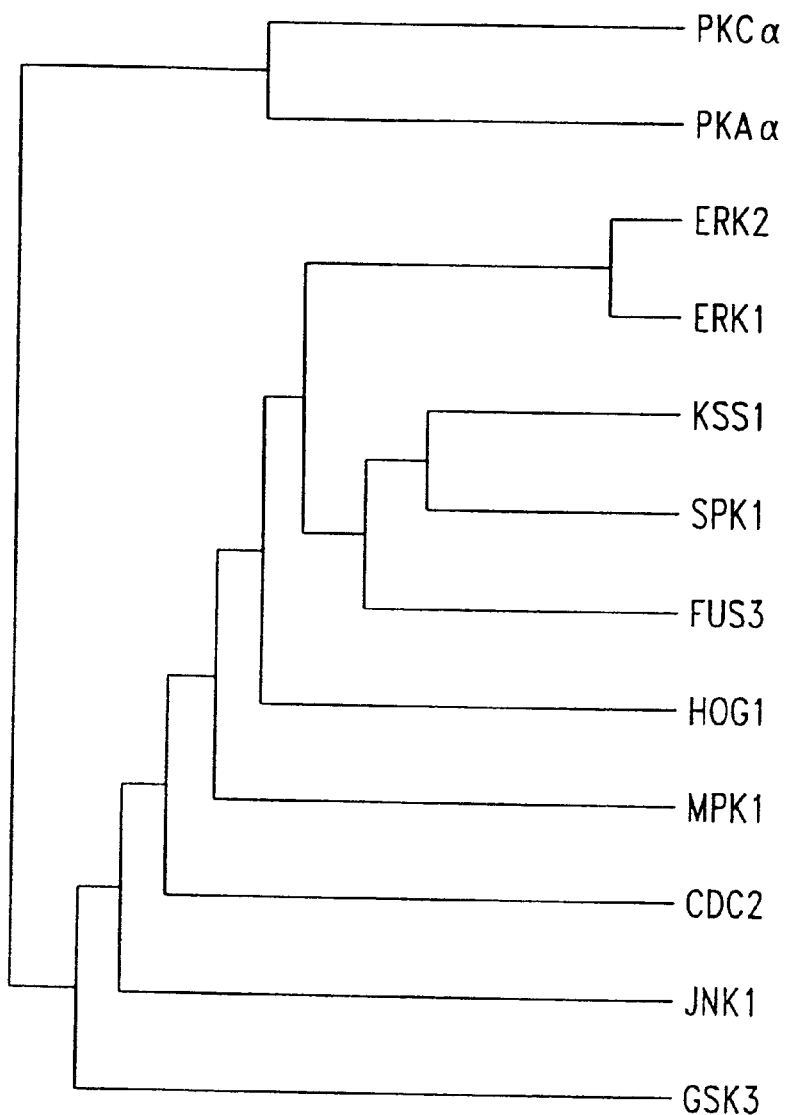
FIG. 18C shows a comparison of the deduced structure of JNK1 with the GenBank data-base.

FIG. 18C shows the comparison which was created by the PILEUP program using a progressive pair-wise alignment and shown as a dendrogram. The identity of the kinases with JNK1 was calculated with the BESTFIT program: ERK1 (39.7%); ERK2 (43.1%); HOG1 (41.1%); FUS3 (41.5%); KSS1 (40.6%); MPK1 (41.0%); SPK1 (40.1%); CDC2 (37.5%); GSK-3a (29.7%); protein kinase Aa (21.5%); and protein kinase Ca (22.6%). The similarity of the kinases to JNK was calculated with the BESTFIT program: ERK1 (64.5%); ERK2 (67.6%); HOG1 (64.2%); FUS3 (63.9%); KSS1 (63.9%); MPK1 (63.7%); SPK1 (63.5%); CDC2 (58.7%); GSK-3a (50.6%); protein kinase Aa (48.8%); and protein kinase Ca (44.2%). The PILEUP and BESTFIT programs were from the Wisconsin Genetics Computer Group.

EXAMPLE 17

Localization of JNK mRNA

To examine the tissue distribution of JNK1, Northern blot analysis was used.
Hybridization Analysis Northern blots were performed using 2 μg of polyA⁺ RNA isolated from different human tissues, fractionated by denaturing agarose gel electrophoresis and transferred onto a nylon membrane (Clontech). The blots were hybridized to a probe that was prepared by labeling the JNK1 cDNA with [α-³²P]dCTP (Amersham International PLC) by random priming (Stratagene Inc.). The integrity of the mRNA samples was confirmed by hybridization to an actin probe. Southern blot analysis was performed using 10 μg of human genomic DNA that was digested with different restriction enzymes, fractionated by agarose gel electrophoresis and transferred onto a nylon membrane. The membrane was probed with a random-primed fragment of JNK1 cDNA (797 bp to 1275 bp). The blots were washed three times with 1×SSC, 0.05% SDS, and 1 mM EDTA prior to autoradiography.

A single major JNK1 transcript (3.5 Kb) was observed in fetal brain (FIG. 19A). In adult tissues there was ubiquitous expression of transcripts that hybridized to the JNK1 probe. However, a tissue-specific heterogeneity of the mRNA was observed in adult tissues (FIG. 19B). This heterogeneity could result from alternative processing of transcripts from a single gene. Alternatively, it is possible that JNK1 represents the prototype for a sub-family of closely-related protein kinases. Consistent with this hypothesis is the observation of multiple bands that hybridized to a JNK1 probe during Southern blot analysis of human genomic DNA (FIG. 19C). Human genomic DNA digested with different restriction enzymes was examined by Southern blot analysis using a JNK1 cDNA probe. The genomic DNA was restricted with EcoRI (lane 1), HindIII (lane 2), BamHI (lane 3), PstI (lane 4), and BgIII (lane 5). The position of DNA size markers in kilobases is illustrated.

EXAMPLE 18

JNK1 is Activated During the UV Response

To characterize the kinase activity of purified JNK1, an expression vector encoding an epitope-tagged JNK1 protein that could be immunoprecipitated using a monoclonal antibody was constructed.

The JNK1 cDNA was first cloned into the expression vector pCMV5 (Andersson, et al., *J. Biol. Chem.* 264:8222–8229, 1989) between the XbaI and HindIII sites. A PCR-based procedure was employed to insert an epitope tag (Asp-Tyr-Lys-Asp-Asp-Asp-Asp-Lys) (SEQ ID NO: 15) between codons 1 and 2 of the JNK1 cDNA (Ho, et al., *Gene* 77:51–59, 1989). A similar method was employed to insert an HA epitope-tag. Substitution of the phosphorylation sites Thr-183 and Tyr-185 by Ala and Phe, respectively, was performed by cassette mutagenesis using a degenerate double-stranded oligonucleotide and the PstI and StyI restriction sites. The sequence of these constructs was confirmed by automated sequencing with a model 373A DNA sequencer (Applied Biosystems).

The plasmid pCMV-Ras/Leu61 was provided by Dr. L. Kozma (University of Massachusetts Medical School). The plasmids encoding GST-Jun fusion proteins were described previously (Hibi, et al., *Genes Dev.* 7:2135–2148, 1993). Plasmid DNA (1 μg) was transfected into COS-1 cells using the lipofectamine method (Gibco-BRL). After 48 hours, the cells were treated without and with TPA, EGF or UV-C.

JNK1 protein kinase activity was detected in the immune-complex. Immunecomplex kinase assays using either M2 immunoprecipitates or purified JNK1, JNK-46, and ERK1 or ERK2 were performed at 30° C. for 20 mins using 3 μg of substrate, 20 μM ATP and 5 μCi of [γ-$^{32}$P]ATP in 30 μl of kinase buffer (25 mM Hepes (pH 7.6), 20 mM MgCl$_2$, 20 mM β-glycerophosphate, 20 mM p-nitrophenyl phosphate, 0.1 mM Na orthovanadate, 2 mM DTT). The reactions were terminated with Laemmli sample buffer and the products were resolved by SDS-PAGE (12% gel). JNK1 protein activity was also measured after SDS-PAGE by the in-gel kinase assay with the substrate GST-cJun(1-79) as described by Hibi, et al., supra, (1993). Solid-phase protein kinase assays were performed as described by Hibi, et al., supra, (1993). Clarified cell extracts were incubated with GST fusion proteins immobilized on GSH-agarose beads. After 3 hours at 4° C., the beads were washed extensively and bound JNK1 was detected by the addition of [γ-$^{32}$P]ATP. The reaction was terminated after 10 mins at 30° C. and the products were resolved by SDS-PAGE. The incorporation of [$^{32}$P]phosphate was visualized by autoradiography and quantitated with a phosphorimager and ImageQuant software (Molecular Dynamics Inc., Sunnyvale, Calif.). The methods used for phosphopeptide mapping (Boyle, et al., *Cell* 64:573–584, 1991) and phosphoamino acid analysis (Alvarez, et al., *J. Biol. Chem* 266:15227–15285, 1991) were described previously.

Figure 20A:
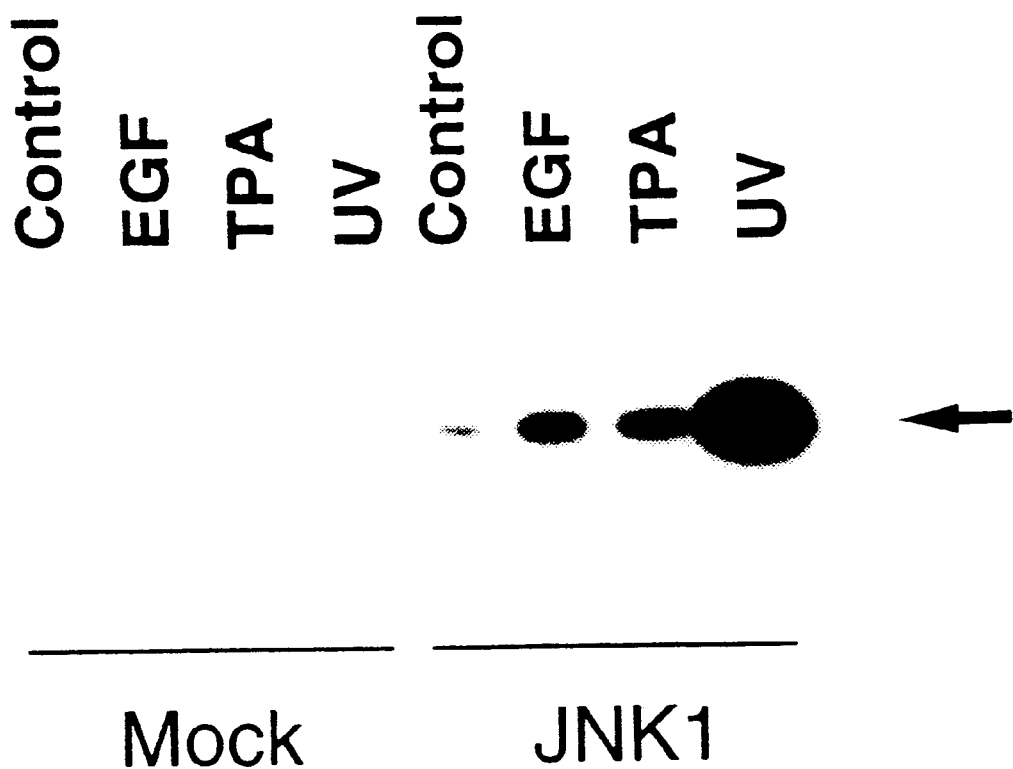
FIG. 20A shows JNK1 kinase activity as measured in an SDS-PAGE using an in-gel kinase assay with GST-c-Jun (1-79) substrate.

In initial studies designed to characterize JNK1 activity, SDS-PAGE and an in-gel kinase assay were used to identify the apparent mass of the JNK1 protein kinase. Essentially identical results were obtained using standard immune-complex kinase assays. Autophosphorylation of JNK1 was not observed in experiments performed in the absence of an exogenous substrate. However, a low level of kinase activity migrating at 46-kDa was detected when a recombinant fragment of the c-Jun activation domain (GST-cJun(1-79)) was used as a substrate (FIG. 20A).

Epitope-tagged JNK1 was expressed in COS cells. Control experiments were performed using mock-transfected cells. After 48 hours, the cells were treated either without or with 100 nM TPA, 10 nM EGF, or 80 J/m$^2$ UV-C and incubated for 1 hr. The cells were lysed in RIPA buffer and the JNK1 proteins were isolated by immunoprecipitation with the M2 monoclonal antibody. JNK1 protein kinase activity was measured after SDS-PAGE using an in-gel kinase assay with the substrate GST-cJun(1-79) polymerized into the gel.

Figure 20B:
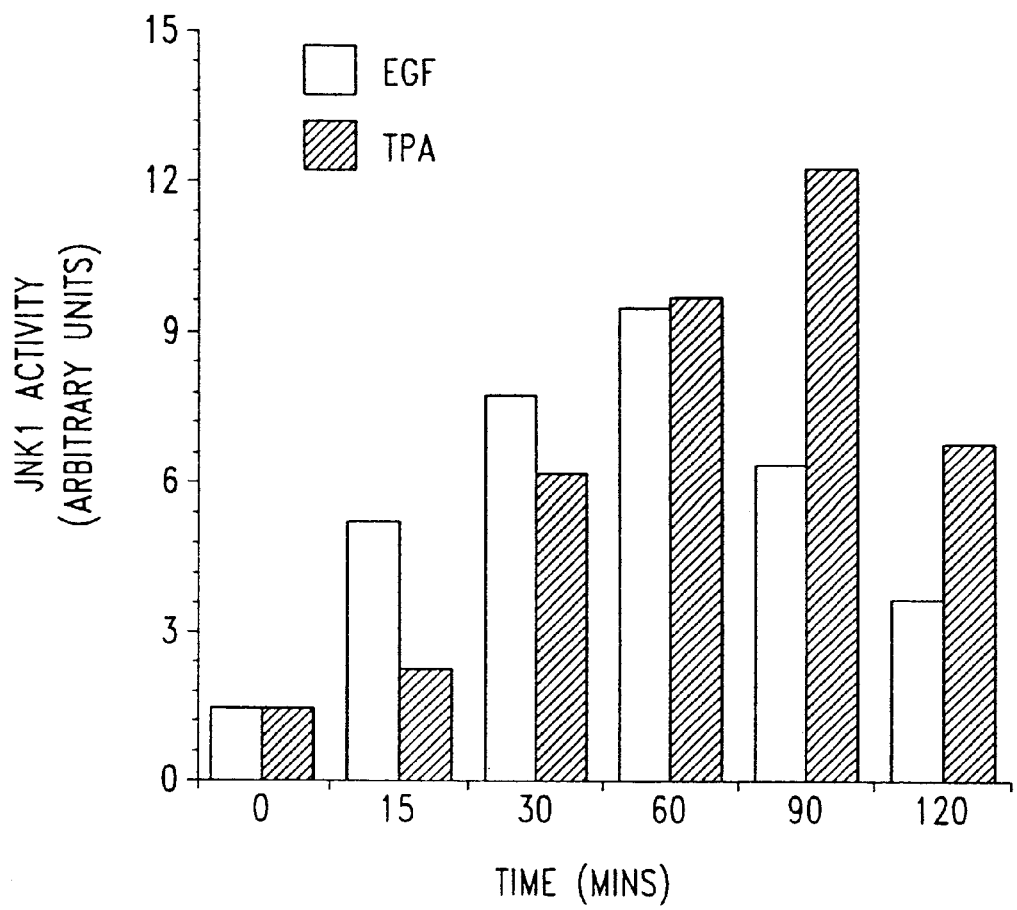
FIG. 20B shows a time course of JNK1 protein kinase activation by EGF and TPA.

COS-1 cells were maintained in. Dulbecco's modified Eagle's medium supplemented with 5% bovine serum albumin (Gibco-BRL). Metabolic labeling with [$^{32}$P]phosphate was performed by incubation of cells in phosphate-free modified Eagle's medium (Flow Laboratories Inc.) supplemented with 0.1% fetal bovine serum and 1 mCi/ml [$^{32}$P] orthophosphate (Dupont-NEN). COS cells were treated with 10 nM EGF or 100 nM thorbol myristate acetate. The cells were then incubated for defined times at 37° C. prior to harvesting and measurement of JNK1 protein kinase activity. The data are presented as arbitrary units. Treatment of the transfected cells with EGF or phorbol ester (TPA) caused a low level of JNK1 activation that was sustained for approximately 2 hours (FIG. 20B). In contrast, exposure to UV radiation caused a marked increase in JNK1 activity.

Significantly, the electrophoretic mobility of the UV-stimulated JNK1 enzymatic activity is similar to JNK-46 (Hibi, et al., supra, 1993). The slightly slower mobility of JNK1 compared with JNK-46 is most likely caused by the octapeptide epitope-tag fused to JNK1.

The UV-dose response was examined by exposing COS cells to UV-C radiation and the cells were harvested after incubation for 1 hr. The time course was investigated by exposure of COS cells to 40 J/m$^2$ UV-C and then incubating the cells for defined times. JNK1 activity was measured by immunoprecipitation with the M2 monoclonal antibody, in-gel kinase assay, and phosphorimager detection.

Phosphorimager Detection

Metabollically labeled cells were lysed in 25 mM Hepes (pH 7.5), 1% Triton X-100, 1% (w/v) deoxycholate, 0.1% (w/v) SDS, 0.5 M NaCl, 50 mM NaF, 1 mM Na orthovanadate, 5 mM EDTA, 10 μg/ml leupeptin, 1 mM PMSF. Soluble extracts were prepared by centrifugation at 100,000×g for 30 mins at 4° C. The extracts were pre-cleared using protein G-Sepharose (Pharmacia-LKB Biotechnologies Inc.) and then incubated with the monoclonal antibody M2 (IBI-Kodak) pre-bound to protein G-Sepharose. The M2 antibody recognizes the epitope Asp-Tyr-Lys-Asp-Asp-Asp-Asp-Lys (Flag; Immunex Corp.) and immunoprecipitates the epitope-tagged JNK1 protein. (In some experiments the monoclonal antibody 12CA5 was used to immunoprecipitate JNK1 tagged with the HA epitope). After 1 hr of incubation, the immunoprecipitates were washed three times with lysis buffer and once with 25 mM Hepes (pH 7.5), 0.2% (w/v) Triton X-100, 1 mM EDTA.

Prior to analysis by Western blotting, protein samples were resolved by SDS-PAGE and electroblotted onto immo-bilon P membranes (Millipore). The membranes were probed with the monoclonal antibody M2 (IBI-Kodak) and immunecomplexes were visualized using enhanced chemi-luminescence detection (Amersham International PLC).

Figure 20C:
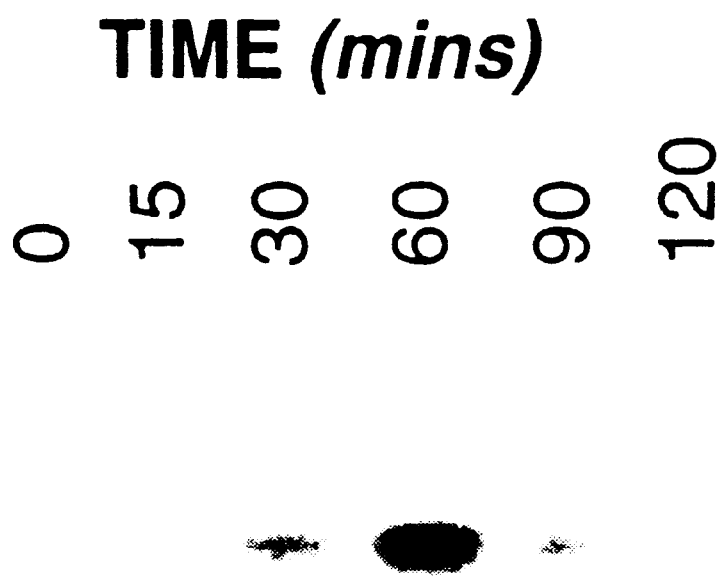
FIGS. 20C and 20D show the time course and dose response of JNK1 activation by UV radiation.
Figure 20D:
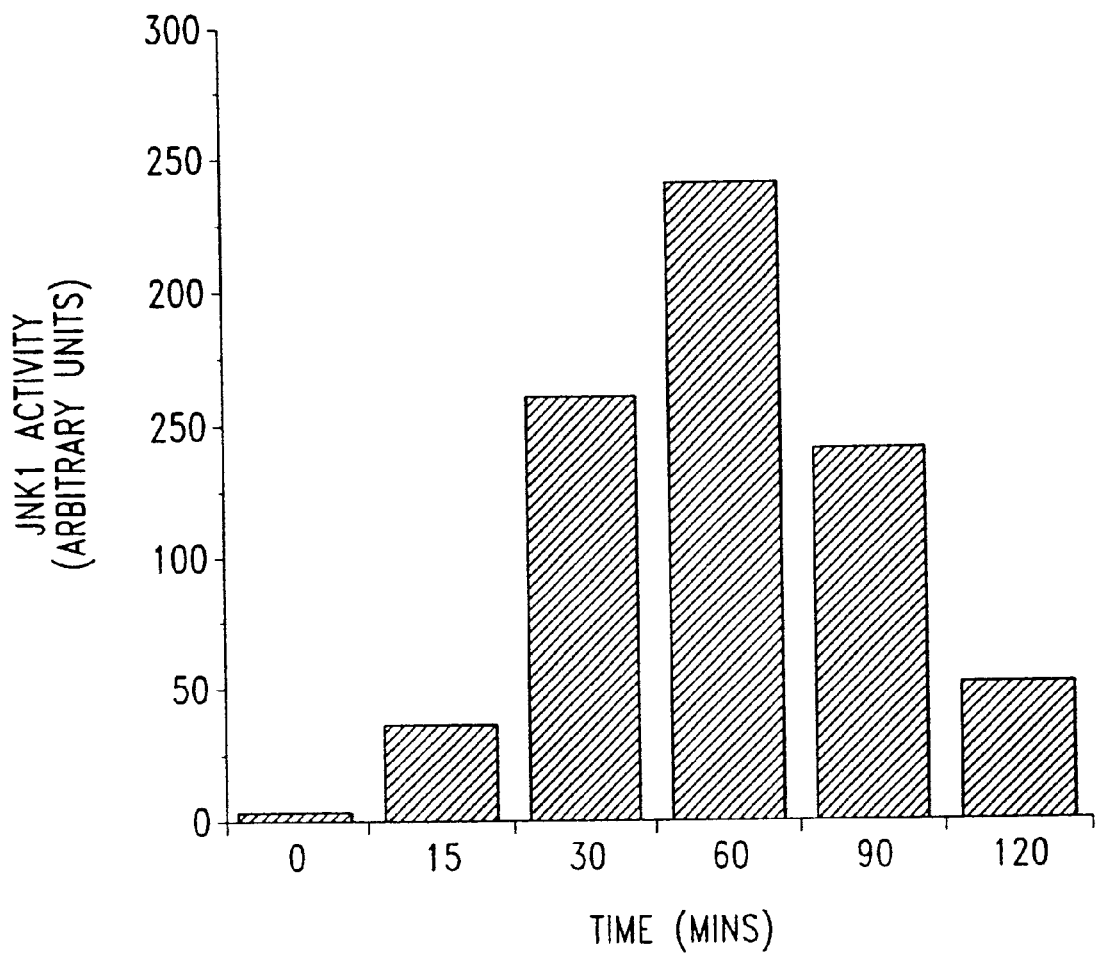
Figure 20E:
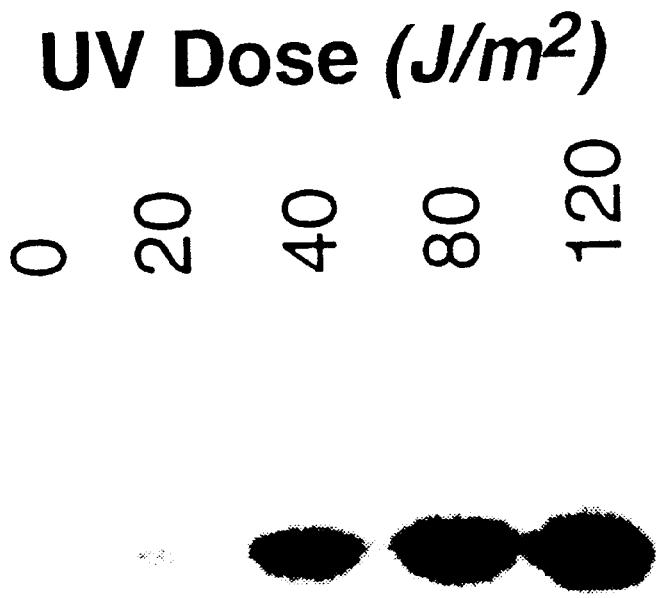
FIGS. 20E and 20F show the dose response of JNK1 UV-induced activation.
Figure 20F:
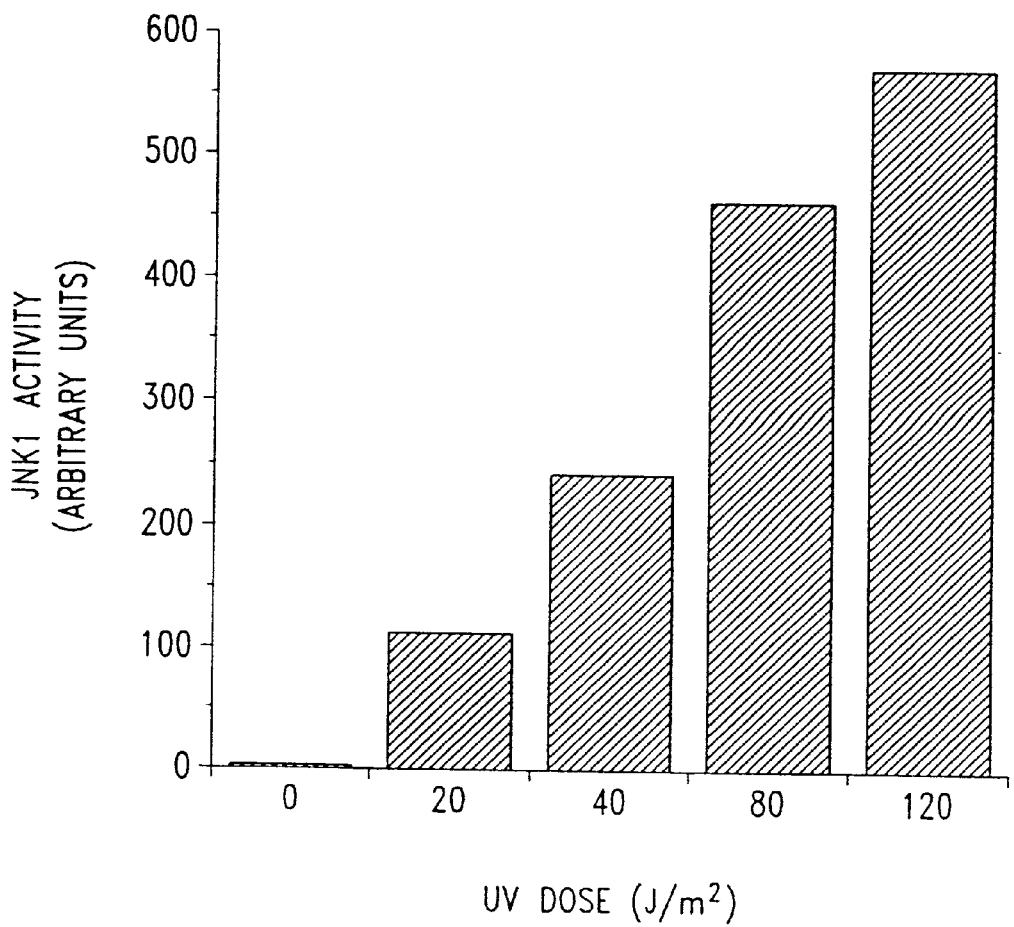
Figure 21A:
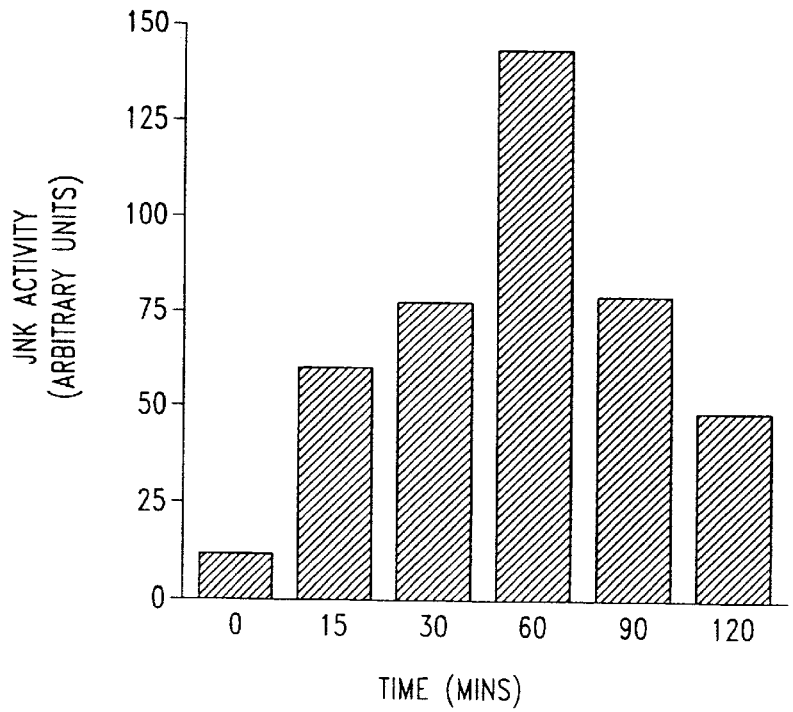
FIGS. 21A and 21B shows a time course and dose response of UV activation of the endogenous JNK1 protein kinase expressed by COS cells.
Figure 21B:
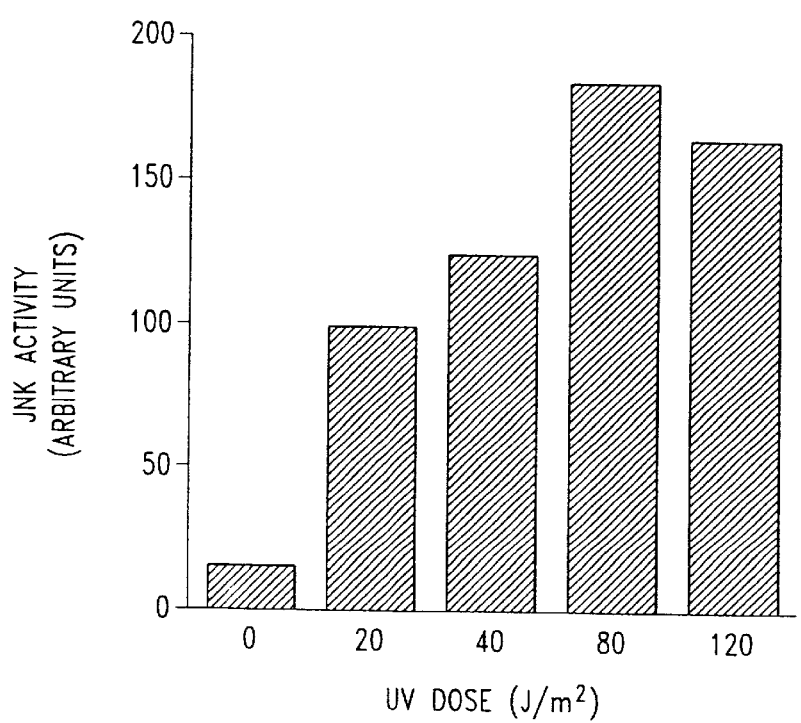

The UV-induced activation of JNK1 occured rapidly after UV-irradiation with maximal activation at 1 hr followed by a progressive decline in JNK1 activity at later times (FIG. 20C). Examination of the UV dose-response revealed detectable JNK1 activation at 20 J/m$^2$ and maximal activation at approximately 80 J/m$^2$ (FIG. 20D). Significantly, the time-course and dose-response of JNK1 activation by UV (FIG. 20) was similar to the regulation of the endogenous JNK-46 protein kinase expressed by COS cells (FIG. 21). FIG. 21 shows the time course and dose response of UV activation of endogenous JNK1 expressed by COS cells. The UV dose-response was examined by exposing COS cells to UV-C radiation and the cells were harvested after 1 hr. The time-course was investigated by exposure of COS cells to 40 J/m$^2$ UV-C and then incubating the cells for defined times. Endogenous JNK1 activity was measured using the solid-phase kinase assay with the substrate GST-cJun(1-79) as described.

The electrophoretic mobility of JNK1, its potent activation by UV, the lack of detectable autophosphorylation, and the efficient phosphorylation of GST-cJun fusion proteins suggests that JNK1 is homologous or identical to the protein kinase activity JNK-46 that has been identified in UV-irradiated cells (Hibi, et al., supra, 1993).

EXAMPLE 19

Ha-Ras Activates JNK1 and Potentiates the UV Response Pathway

The results of previous studies have shown that onco-genically activated Ras stimulates the NH$_2$-terminal phosphorylation of c-Jun (Binetruy, et al., supra., 1991; Smeal, et al., supra., 1991; 1992). In addition, Ras is involved in the UV-response leading to increased c-Jun activity (Devary, et al., supra, 1992; Radler-Pohl, et al., EMBO J. 12:1005–1012, 1993). The effect of oncogenically activated Ras on JNK1 was studied. Epitope-tagged JNK1 was coexpressed in COS cells without or with activated Ha-Ras. After 48 hours, the cells were exposed to different doses of UV-C and then incubated for 1 hr at 37° C. JNK1 was isolated by immunoprecipitation with the M2 monoclonal antibody and JNK1 activity was measured using an immunecomplex kinase assay with the substrate GST-cJun(1-79).

Figure 22A:
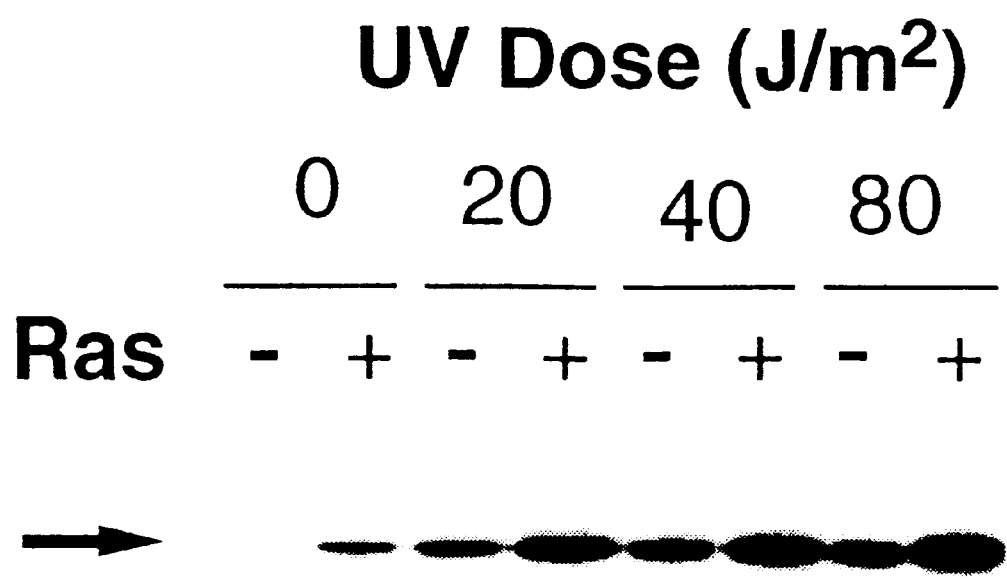
FIGS. 22A and 22B show an immunocomplex kinase assay with substrate GST-c-Jun (1-79) to show the effect of Ha-Ras and UV on JNK1 activity.
Figure 22B:
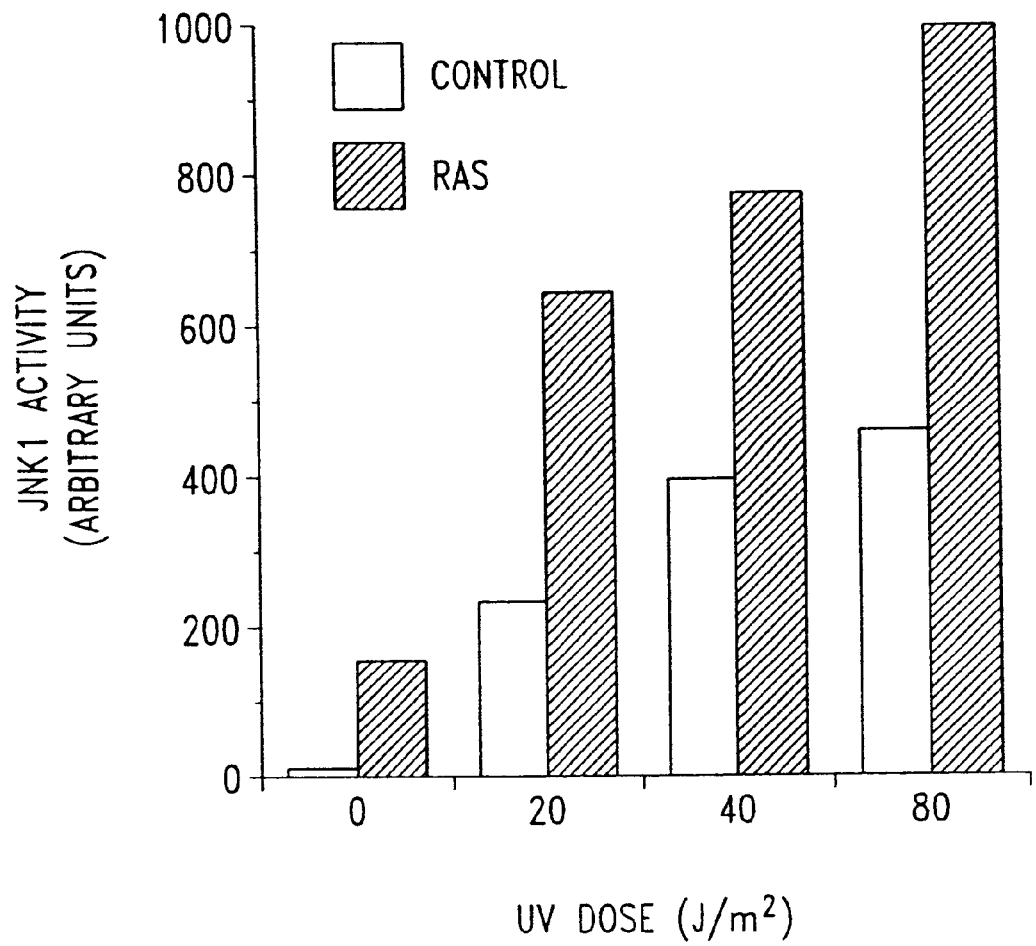

Significantly, expression of activated Ha-Ras potentiated UV-stimulated JNK1 activity (FIG. 22). By itself, Ha-Ras caused JNK1 activation that was approximately 40% of that obtained with 40 J/m$^2$ UV-irradiation. These data indicate that Ha-Ras partially activates JNK1 and that Ha-Ras potentiates the activation caused by UV. JNK1 was expressed in COS cells and activated by exposure to UV light. JNK1 was isolated by immunoprecipitation with the M2 monoclonal antibody and used to phosphorylate 3 μg of GST (control, lane 1), GST-cJun(1-223) (lane 2), GST-cJun(43-233) (lane 3), GST-cJun(1-79) (lane 4), GST-cJun(1-223/Ala63, Ala-73) (lane 5), GST-chcJun(1-144) (chicken c-Jun, lane 6), GST-chvJun(1-144) (chicken v-Jun, lane 7), or MBP (lane 8). After the phosphorylation reaction, the different proteins were separated by SDS-PAGE and visualized by autoradiography. The same proteins were used as substrates for JNK-46 purified from UV-irradiated HeLa cells (B) or a mixture of purified ERK1 and ERK2 (C). The Coomassie-blue stain of the protein substrates is also shown (D). The migration positions of the full-length substrate proteins are indicated by the dots.

EXAMPLE 20

JNK1 Phosphorylates C-JUN at SER-63 and SER-73

To investigate the relationship between JNK1 and JNK-46, the substrate specificity of JNK was examined.

FIG. 23 (panel A) shows that both GST-vJun and myelin basic protein (MBP) are very poor substrates for JNK1, while GST-cJun fusion proteins are excellent JNK1 substrates. This pattern of substrate specificity is identical to JNK-46 purified from UV-irradiated HeLa cells (FIG. 23, panel B). Like JNK-46, JNK1 efficiently phosphorylated GST-cJun fusion proteins containing residues 1-223 and 1-79 of c-Jun. However, a deletion of c-Jun NH$_2$-terminal sequences including the d-domain (residues 1-42) caused a marked decrease in phosphorylation by JNK1. Replacement of Ser-63 and Ser-73 with Ala also decreased the observed phosphorylation. On the other hand, the substrate specificity of the MAP kinases ERK1 and ERK2 was markedly different from that of JNK1 (FIG. 23, panel C). In this-case myelin basic protein (MBP) was a significantly better substrate than GST-cJun. In addition, there was no discrimination between GST-cJun, GST-vJun, and the mutants lacking JNK1 phosphorylation sites [GST-cJun(Ala)] or the JNK1 binding site [GST-CJun(43-223)]. The Coomasie blue stain of the protein substrates is also shown (FIG. 23, panel D).

To further establish the substrate specificity of JNK1, the sites of c-Jun phosphorylation were determined by phosphopeptide mapping. GST-cjun(1-223), GST-cJun(1-223/Ala63,73), GST-cJun(1-79) and full-length c-Jun were phosphorylated by epitope-tagged JNK1 immunopurified from UV-irradiated transfected COS cells. Full-length c-Jun was also phosphorylated by JNK-46 purified from UV-irradiated HeLa cells. The phosphorylated proteins were isolated by SDS-PAGE, eluted from the gel, and digested with trypsin. The tryptic digests were separated by thin layer electrophoresis (horizontal dimension) followed by ascending chromatography (vertical dimension) and visualized by autoradiography. The origin and the phosphopeptides X, Y, T1, and T2 are indicated.

The major phosphopeptides observed were X and Y (FIG. 24). These phosphopeptides were also found in maps of c-Jun phosphorylated by purified JNK-46. In previous studies, these phosphopeptides were shown to correspond to the phosphorylation of the regulatory sites Ser-63 and Ser-73 (Binetruy, et al., Nature 351:122–127, 1991; Pulverer, et al., Nature 353:670–674, 1991; Smeal, et al., supra, 1991; 1992). Examination of the primary sequence surrounding these phosphorylation sites indicates the consensus sequence motif Leu/Ala-Ser*-Pro-Asp/Glu (SEQ ID NO: 16). A low level phosphorylation of sites other than Ser-63 and Ser-73 was also observed, and was not affected by substitution of Ser-63 and Ser-73 with Ala (phosphopeptides T1 and T2). These sites correspond to phosphorylation at Thr-Pro motifs (Thr-91, Thr-93, or Thr-95) that were previously identified as minor JNK1 sites (Hibi, et al., supra, 1993). Importantly, no phosphorylation of the COOH-terminal sites (Boyle, et al., Cell 64:573–584, 1991; Lin, et al., Cell 70:777–789,1992) including Ser-243, which is phosphorylated by purified ERKs (Alvarez et al., J. Biol. Chem. 266:15227–15285, 1991) was observed. The low level of COOH-terminal phosphorylation previously observed with partially purified JNK1 preparations (Hibi, et al., supra, 1993) is most likely due to contamination with other protein kinases.

EXAMPLE 21

JNK1 Associates With the c-JUN Transactivation Domain

The observation that v-Jun is not a good JNK1 substrate is intriguing because both v-Jun and c-Jun contain the phosphoacceptor sites Ser-63 and Ser-73. This suggests that the presence of the primary sequence encoding a phosphorylation site may be insufficient for efficient substrate recognition by JNK1. In previous studies a small region of the c-Jun transactivation domain, the δ sub-domain (Vogt, et al., Adv. Cancer Res. 55:1–35, 1990), was proposed to mediate the direct interaction of c-Jun with a physiologically relevant protein kinase that phosphorylates Ser-63 and Ser-73 (Adler, et al., Proc. Natl. Acad. Sci. USA, 89:5341–5345, 1992) and was identified as a binding site for JNK1. According to this hypothesis, the inefficient phosphorylation of v-Jun is due to defective JNK1 binding.

To investigate whether JNK1 is a physiologically relevant c-Jun protein kinase, the binding of immunopurified JNK1 isolated from UV-stimulated COS cells was studied. The binding of JNK1 to c-Jun was detected using a solid-phase kinase assay in which JNK1 binds to an immobilized GST-cJun fusion protein and, after the addition of ATP, phosphorylates Ser-63 and Ser-73.

COS cells expressing epitope-tagged JNK1 were lysed in Buffer A and a soluble extract was obtained after centrifugation at 100,000×g for 20 mins. COS cell extracts (250 μg) were incubated with 20 μg GST or GST-cJun immobilized on 10 μl GSH-agarose at 4° C. for 5 hours. The beads were washed four times with Buffer A and JNK1 was eluted with Laemmli sample buffer.

Detection of JNK1 binding to the c-Jun transactivation domain was examined using a solid-state protein kinase assay. Epitope-tagged JNK1 was expressed in COS cells and activated by UV-irradiation. Mock-transfected COS cells were used as a control. After 1 hour, the cells were lysed and subjected to immunoprecipitation with the M2 monoclonal antibody. The immunecomplexes were eluted with urea and, after dialysis, the isolated JNK1 was incubated with GST-Jun fusion proteins bound to GSH-agarose beads. The beads were washed extensively and bound JNK1 was detected using a solid-phase kinase assay as described. The phosphorylated proteins were resolved by SDS-PAGE and detected by autoradiography. The dots indicate the migration of GST and the different GST-cJun proteins (see FIG. 25A).

To examine whether the binding of JNK1 to c-Jun was altered by the state of JNK1 activation, the binding of epitope-tagged JNK1 to immobilized c-Jun was examined by Western blotting. JNK1 from either unstimulated or UV-irradiated cells bound to GST-cJun. Epitope-tagged JNK1 was expressed in COS cells (lanes 3–5). Mock-transfected COS cells were used in control experiments (lanes 1 & 2). The cells were either untreated (lanes 1 & 3) or irradiated with 40 J/m$^2$ UV-C (lanes 2, 4, & 5). Cell lysates were prepared and incubated with GST-cJun(1-79) (lanes 1–4) or GST (lane 5) immobilized on GSH-agarose beads. The beads were washed extensively and bound JNK1 was detected by Western blot analysis using the M2 monoclonal antibody. Lane 6 represents an unfractionated lysate of cells expressing JNK1 (see FIG. 25B).

Figure 25A:
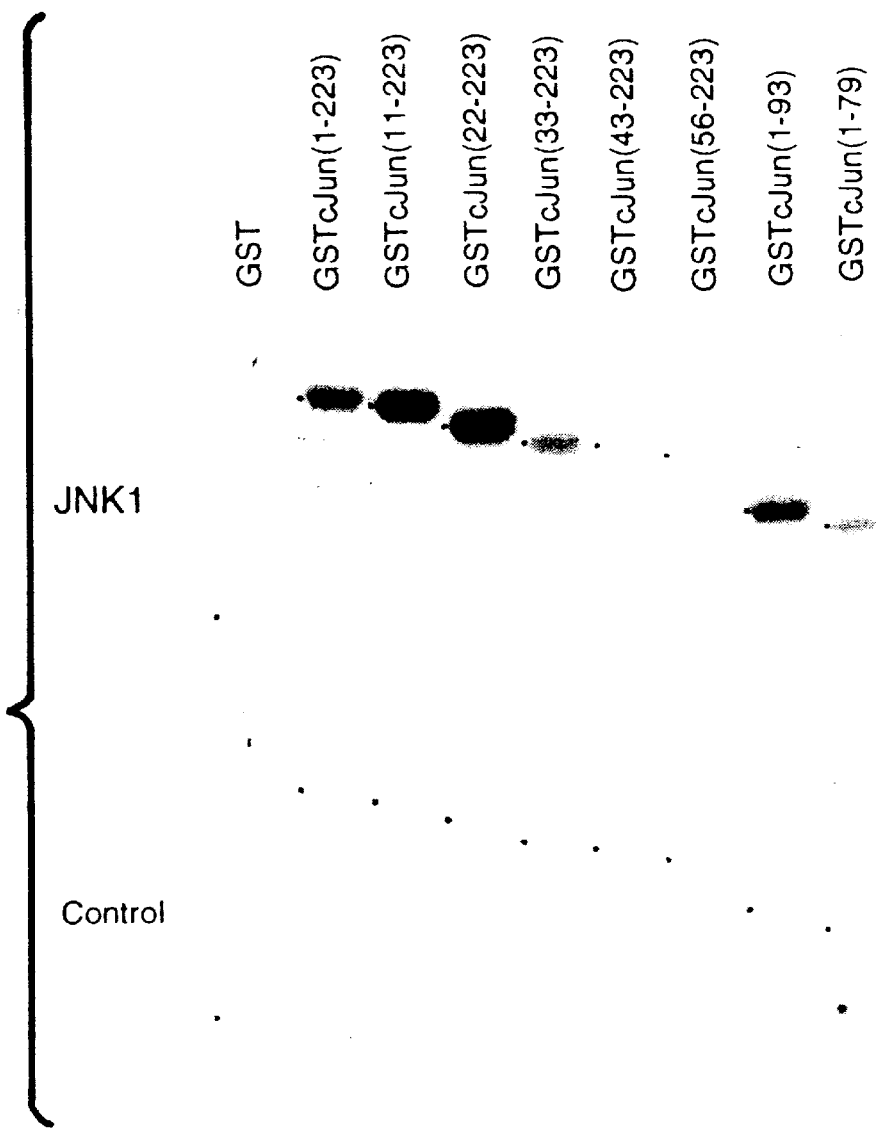
FIG. 25A shows phosphorlated GST-c-Jun proteins detected by a solid state protein kinase assay.
Figure 25B:
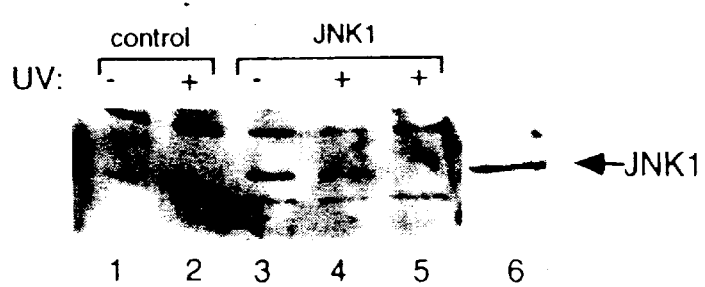
FIG. 25B shows Western blot analysis of epitope-tagged JNK1 expressed in COS cells.

Deletion of residues 1–42 or 1–55 of the c-Jun transactivation domain, which includes the γ sub-domain, prevented binding of JNK1 (FIG. 25A). Deletion of c-Jun residues 1–32 reduced, but did not eliminate, JNK1 binding. However, deletion of residues 1–22 had no effect on JNK1 binding. Previous studies have demonstrated that the effect of these deletions on GST-cJun phosphorylation is due to changes in JNK1 binding rather than the presentation of the phosphoacceptor sites. Taken together, these observations demonstrate that a region of the c-Jun NH$_2$-terminus adjacent to the major phosphorylation sites (Ser-63 and Ser-73) is required for binding to JNK1.

These data demonstrate that JNK1 binds to a specific region (residues 23–79) of the NH$_2$-terminal transactivation domain of c-Jun. It is likely that this binding reflects the direct interaction of JNK1 with c-Jun. However, these experiments do not exclude the possibility that an accessory protein is required for JNK1 binding to c-Jun or that an accessory protein may stabilize this interaction.

EXAMPLE 22

Phosphorylation at Thr and Tyr is Required for UV-Induced JNK1 Activation

MAP kinases are activated by dual phosphorylation at Thr and Tyr residues within sub-domain VIII. Therefore tested whether phosphorylation at these sites is required for JNK1 activation by UV. The predicted phosphorylation sites Thr-183 and Tyr-185 were replaced by Ala and Phe, respectively, using site-directed mutagenesis.

FIG. 26, panels A, B and C show the results indicating that substitution of Thr-183 or Tyr-185 blocks the UV-stimulated phosphorylation of JNK1. Site-directed mutagenesis was used to replace the JNK1 phosphorylation sites Thr-183 with Ala and Tyr-185 with Phe. The epitope-tagged wild-type JNK1 (TPY) and the mutated JNK1 proteins (APY, TPF, and APF) were expressed in COS cells. The cells were either exposed or not exposed to 80 J/m$^2$ UV-C, incubated for 1 hr at 37° C., and then lysed in RIPA buffer. JNK1 was isolated by immunoprecipitation with the M2 monoclonal antibody and SDS-PAGE. The level of expression of the wild-type and mutated JNK1 proteins was examined by Western blot analysis using the M2 monoclonal antibody and enhanced chemiluminescence detection (FIG. 26A). The phosphorylation state of JNK1 was examined using cells metabolically-labeled with [$^{32}$P]phosphate (FIG. 26B). The phosphorylated JNK1 proteins were subjected to phosphoamino acid analysis (FIG. 26C).

Figure 26A:
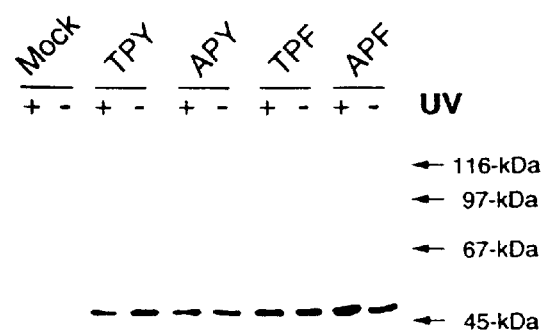
FIG. 26 show analyses of UV-stimulated phosphorylation of JNK1 after substitution of Thr-183 or Tyr-185. Panel A & B show Western blot analysis using chemiluminescence detection or cells metabolically labeled with $^{32}$P-phosphate, respectively. Panel C shows phosphoamino acid analysis. Panel D shows an SDS-PAGE using an in-gel kinase assay with the substrate GST-c-Jun (1-79).
Figure 26B:
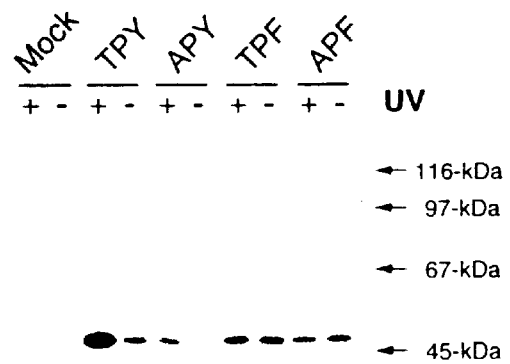
Figure 26C:
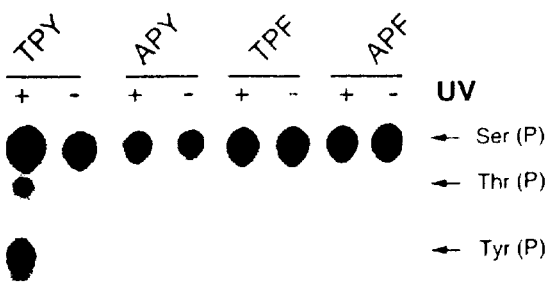
Figure 26D:
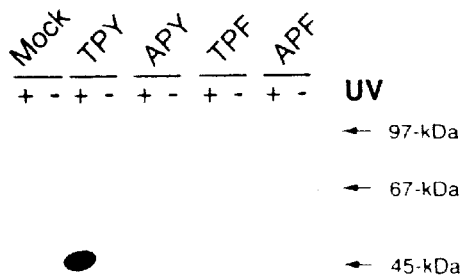

JNK1 protein kinase activation by UV is inhibited by substitution of Tir-183 or Tyr-185 as shown in FIG. 26D. Epitope-tagged JNK proteins were immunoprecipitated from COS cell lysates using the M2 monoclonal antibody. JNK1 protein kinase activity was measured after SDS-PAGE using an in-gel kinase assay with the substrate GST-cJun(1-79).

A similar level of expression of the wild-type and mutated JNK1 proteins was obtained in transiently transfected COS cells (FIG. 26A). JNK1 phosphorylation was examined using cells metabolically-labeled with [$^{32}$F]phosphate. FIG. 26B shows that UV-treatment caused increased phosphorylation of wild-type JNK1. Phosphoamino acid analysis demonstrated a high level of basal serine phosphorylation of JNK1 (FIG. 26C). The UV-stimulated phosphorylation of JNK1 was accounted for by increased [$^{32}$P] phosphothreonine and [$^{32}$P]phosphotyrosine (FIG. 26C).

F9 cells were transfected with 10 μg of expression vector encoding epitope-tagged (HA) JNK1. The cells were labeled 12 hours after transfection for 4 hours with [$^{32}$P]phosphate (0.5 mCi/ml). One dish was exposed to 100 J/m$^2$ UV-C and the cells were harvested 45 mins later. HA-JNK1 was purified by immunoprecipitation (12CA5 antibody) and SDS-PAGE. Phosphorylated JNK1 was eluted from the gel and digested with trypsin. The tryptic digests were separated by thin layer electrophoresis (horizontal dimension) followed by ascending chromatography (vertical dimension) and visualized by autoradiography (9 days at −80° C.). The constitutive phosphopeptide (C), the induced phosphopeptide (I), and the origin (arrow head) are indicated in FIG. 27.

Tryptic phosphopeptide mapping demonstrated that this dual phosphorylation was associated with the appearance of one major [$^{32}$P] phosphopeptide (FIG. 27). The presence of this novel phosphopeptide is consistent with the identification of Thr-183 and Tyr-185 as the sites of UV-stimulated phosphorylation of JNK1. This hypothesis was confirmed by demonstrating that mutations at Thr-183 and Tyr-185 blocked the UV-stimulated phosphorylation of JNK1 (FIG. 26C). Significantly, these mutated JNK1 proteins did not exhibit kinase activity when isolated from either unstimulated or UV-irradiated cells (FIG. 26D). Together, these data demonstrate that the mechanism of JNK1 activation involves increased phosphorylation at Thr-183 and Tyr-185.

EXAMPLE 23

Cloning of JNK2(55 kD)

The JNK isoform, JNK2, was molecularly cloned by screening a human HeLa cell cDNA library by hybridization with a random-primed probe prepared from the JNK1 cDNA. The sequence of the JNK2 cDNA shown in FIG. 28, indicates that it encodes an approximately 55-kDa protein (FIG. 29) that is related to JNK1. The cDNA is 1782 base pairs long and contains an open reading frame from nucleotides 59 to 1330, encoding a 424 amino acid protein (SEQ ID NO: 17 and 18, respectively). There is a high level of protein sequence identity between JNK1 and JNK2 indicating that these enzymes are closely related. The major sequence difference between JNK1 and JNK2 is that JNK2 contains a COOH terminal extension compared with JNK1. The functional properties of JNK2 are similar to JNK1 indicating that these protein kinases form a group with related biological functions.

JNK2 activity was induced by UV treatment as determined by the methods utilized for examining UV activation of JNK1, in Examples 3 and 18 above. Although similarly regulated, the 46 kD polypeptide of JNK1 exhibits a higher affinity for binding to c-Jun than the 55 kD polypeptide (Example 6 and Hibi, et al., supra, 1993). The activity of both forms of JNK (46 and 55) is rapidly and potently stimulated by UV radiation. Although the molecular mechanisms mediating the tumor-promoting activity of UV are not completely understood, it is apparent that JNK1 and JNK2 are involved in the potentiation of AP-1 activity and activated by Ha-Ras and are likely involved as mediators of UV-induced tumor promotion.

The foregoing is meant to illustrate, but not to limit, the scope of the invention. Indeed, those of ordinary skill in the art can readily envision and produce further embodiments, based on the teachings herein, without undue experimentation.

SEQUENCE ID LISTING

SEQ ID NO: 1 is the amino acid sequence of residues 33–79 of c-Jun.

SEQ ID NO: 2 is the nucleotide sequence for an N-terminal primer used for producing c-Jun truncation mutants.

SEQ ID NO: 3 is the nucleotide sequence for an N-terminal primer used for producing c-Jun truncation mutants.

SEQ ID NO: 4 is the nucleotide sequence for an N-terminal primer used for producing c-Jun truncation mutants.

SEQ ID NO: 5 is the nucleotide sequence for an N-terminal primer used for producing c-Jun truncation mutants.

SEQ ID NO: 6 is the nucleotide sequence for an N-terminal primer used for producing c-Jun truncation mutants.

SEQ ID NO: 7 is the nucleotide sequence for a C-terminal primer used for producing c-Jun truncation mutants.

SEQ ID NO: 8 is the nucleotide sequence for a C-terminal primer used for producing c-Jun truncation mutants.

SEQ ID NO: 9 is the nucleotide sequence and deduced amino acid sequence for c-jun and c-Jun.

SEQ ID NO: 10 is the deduced amino acid sequence of c-Jun.

SEQ ID NO: 11 is the nucleotide sequence and deduced amino acid sequence of JNK1.

SEQ ID NO: 12 is the deduced amino acid sequence of JNK1.

SEQ ID NO: 13 and 14 are the nucleotide sequences of degenerate oligonucleotides for cloning JNK1.

SEQ ID NO: 15 is the amino acid sequence of an epitope tag between codons 1 and 2 of JNK1 cDNA.

SEQ ID NO: 16 is the amino acid sequence of a consensus sequence motif surrounding phosphorylation sites Ser-63 and Ser-73.

SEQ ID NO:17 is the nucleotide and deduced amino acid sequence of JNK2.

SEQ ID NO:18 is the deduced amino acid sequence of JNK2.

SEQ ID NO:19 is the deduced amino acid sequence of HOG1.

SEQ ID NO:20 is the deduced amino acid sequence of MPK1.

SEQ ID NO:21 is the deduced amino acid sequence of FUS3.

SEQ ID NO:22 is the deduced amino acid sequence of KSS1.

SEQ ID NO:23 is the deduced amino acid sequence of ERK1.

SEQ ID NO:24 is the deduced amino acid sequence of ERK2.

SEQ ID NO:25 is the amino acid sequence of a MAP kinase consensus sequence.

What is claimed is:

1. An isolated polynucleotide encoding a c-Jun N-terminal kinase, wherein said polynucleotide hybridizes to SEQ ID No. 13 and SEQ ID No. 14 under stringent conditions and wherein said polynucleotide encodes a polypeptide that phosphorylates the c-Jun N-terminal activation domain.

2. An isolated polynucleotide encoding a c-Jun N-terminal kinase, wherein said polynucleotide hybridizes to the complement of SEQ ID No. 11 under stringent conditions and wherein said polynucleotide encodes a polypeptide that phosphorylates the c-Jun N-terminal activation domain.

3. The polynucleotide of claim 1 or 2 wherein the hybridization conditions comprise washing with 1×SSC, 0.05% SDS and 1 mM EDTA.

4. The polynucleotide of claim 1 or 2 wherein the polynucleotide is isolated from brain.

5. The polynucleotide of claim 1 or 2 wherein the polynucleotide is expressed in brain.

6. An isolated nucleic acid encoding a c-Jun N-terminal kinase wherein said nucleic acid hybridizes to the complement of SEQ ID No. 11 under stringent conditions and wherein said nucleic acid encodes a polypeptide that phosphorylates the c-Jun N-terminal activation domain.

7. An isolated nucleic acid encoding a c-Jun N-terminal kinase wherein said nucleic acid hybridizes to the complement of SEQ ID No. 17 under stringent conditions and wherein said nucleic acid encodes a polypeptide that phosphorylates the c-Jun N-terminal activation domain.

8. The nucleic acid of claim 6 or 7 wherein the hybridization conditions comprise washing 1×SSC, 0.05% SDS and 1 mM EDTA.

9. The nucleic acid of claim 6 or 7 wherein the nucleic acid is isolated from brain.

10. The nucleic acid of claim 6 or 7 wherein the nucleic acid is expressed in brain.

11. A host cell containing the polynucleotide of claim 1 or 2.

12. A host cell containing the polynucleotide of claim 4.

13. A host cell containing the polynucleotide of claim 5.

14. A host cell containing the nucleic acid of claim 6 or 7.

15. A host cell containing the nucleic acid of claim 9.

16. A host cell containing the nucleic acid of claim 10.

17. An expression vector comprising a polynucleotide of claim 1 or 2.

18. An expression vector comprising the polynucleotide of claim 4.

19. An expression vector comprising the polynucleotide of claim 5.

20. An expression vector comprising the nucleic acid of claim 6 or 7.

21. An expression vector comprising the nucleic acid of claim 9.

22. An expression vector comprising the nucleic acid of claim 10.

23. An isolated polypeptide with serine threonine kinase activity that binds to residues 33–79 of c-Jun (SEQ ID No. 1) and is capable of phosphorylating the c-Jun N-terminal activation domain.

24. The polypeptide of claim 23 wherein the polypeptide is expressed in brain.

25. The polypeptide of claim 23 or 24 which is approximately 46 kD as determined by SDS-PAGE.

26. The polypeptide of claim 23 or 24 which is approximately 55 kD as determined by SDS-PAGE.

27. The polypeptide of claim 23 or 24 which is approximately 46 kD or 55 kD as determined by SDS-PAGE.

* * * * *

```
SEQUENCE LISTING

<160> NUMBER OF SEQ ID NOS: 25

<210> SEQ ID NO 1
<211> LENGTH: 47
<212> TYPE: PRT
<213> ORGANISM: Artificial sequence
<220> FEATURE:
<223> OTHER INFORMATION: Synthetic peptide

<400> SEQUENCE: 1

Ile Leu Lys Gln Ser Met Thr Leu Asn Leu Ala Asp Pro Val Gly Ser
1               5                   10                  15

Leu Lys Pro His Leu Arg Ala Lys Asn Ser Asp Leu Leu Thr Ser Pro
            20                  25                  30

Asp Val Gly Leu Leu Lys Leu Ala Ser Pro Glu Leu Glu Arg Leu
        35                  40                  45
```

```
<210> SEQ ID NO 2
<211> LENGTH: 35
<212> TYPE: DNA
<213> ORGANISM: Artificial sequence
<220> FEATURE:
<223> OTHER INFORMATION: PCR primer

<400> SEQUENCE: 2
tctgcaggat ccccatgact gcaaagatgg aaacg                          35

<210> SEQ ID NO 3
<211> LENGTH: 34
<212> TYPE: DNA
<213> ORGANISM: Artificial sequence
<220> FEATURE:
<223> OTHER INFORMATION: PCR primer

<400> SEQUENCE: 3
tctgcaggat cccgacgat gccctcaacg cctc                            34

<210> SEQ ID NO 4
<211> LENGTH: 35
<212> TYPE: DNA
<213> ORGANISM: Artificial sequence
<220> FEATURE:
<223> OTHER INFORMATION: PCR primer

<400> SEQUENCE: 4
tctgcaggat ccccgagagc ggaccttatg gctac                          35

<210> SEQ ID NO 5
<211> LENGTH: 35
<212> TYPE: DNA
<213> ORGANISM: Artificial sequence
<220> FEATURE:
<223> OTHER INFORMATION: PCR primer

<400> SEQUENCE: 5
tctgcaggat ccccgccgac ccagtgggga gcctg                          35

<210> SEQ ID NO 6
<211> LENGTH: 35
<212> TYPE: DNA
<213> ORGANISM: Artificial sequence
<220> FEATURE:
<223> OTHER INFORMATION: PCR primer

<400> SEQUENCE: 6
tctgcaggat ccccaagaac tcggacctcc tcacc                          35

<210> SEQ ID NO 7
<211> LENGTH: 30
<212> TYPE: DNA
<213> ORGANISM: Artificial sequence
<220> FEATURE:
<223> OTHER INFORMATION: PCR primer

<400> SEQUENCE: 7
tgaattctgc aggcgctcca gctcgggcga                                30

<210> SEQ ID NO 8
<211> LENGTH: 33
<212> TYPE: DNA
<213> ORGANISM: Artificial sequence
<220> FEATURE:
<223> OTHER INFORMATION: PCR primer
```

<400> SEQUENCE: 8

```
tgaattcctg caggtcggcg tggtggtgat gtg                            33
```

<210> SEQ ID NO 9
<211> LENGTH: 2096
<212> TYPE: DNA
<213> ORGANISM: Homo Sapiens
<220> FEATURE:
<221> NAME/KEY: CDS
<222> LOCATION: (412)..(1404)
<223> OTHER INFORMATION:

<400> SEQUENCE: 9

```
gaattccggg gcggccaaga cccgccgccg gccggccact gcagggtccg cactgatccg      60
ctccggcgga gagccgctgc tctgggaagt cagttcgcct gcggactccg aggaaccgct     120
gcgcacgaag agccgtcagt gagtgaccgc gacttttcaa gcccgggtag ggcgcgcgag     180
tcgacaagta agagtgcggg aggcatctta attaaccctg cgctccctgg agcagctggt     240
gaggagggcg cacgggacg acagccagcg ggtgcgtgcg ctcttagaga aactttccct      300
gtcaaaggct ccgggggggcg cgggtgtccc ccgcttgcca cagccctgtt gcggccccga    360
aacttgtgcg cgcacgccaa actaacctca cgtgaagtga cggactgttc t atg act     417
                                                         Met Thr
                                                           1
```

```
gca aag atg gaa acg acc ttc tat gac gat gcc ctc aac gcc tcg ttc      465
Ala Lys Met Glu Thr Thr Phe Tyr Asp Asp Ala Leu Asn Ala Ser Phe
        5                  10                  15 ctc ccg tcc gag agc gga cct tat ggc tac agt aac ccc aag atc ctg      513
Leu Pro Ser Glu Ser Gly Pro Tyr Gly Tyr Ser Asn Pro Lys Ile Leu
     20                  25                  30 aaa cag agc atg acc ctg aac ctg gcc gac cca gtg ggg agc ctg aag      561
Lys Gln Ser Met Thr Leu Asn Leu Ala Asp Pro Val Gly Ser Leu Lys
 35                  40                  45                  50 ccg cac ctc cgc gcc aag aac tcg gac ctc ctc acc tcg ccc gac gtg      609
Pro His Leu Arg Ala Lys Asn Ser Asp Leu Leu Thr Ser Pro Asp Val
                 55                  60                  65 ggg ctg ctc aag ctg gcg tcg ccc gag ctg gag cgc ctg ata atc cag      657
Gly Leu Leu Lys Leu Ala Ser Pro Glu Leu Glu Arg Leu Ile Ile Gln
             70                  75                  80 tcc agc aac ggg cac atc acc acc acg ccg acc ccc acc cag ttc ctg      705
Ser Ser Asn Gly His Ile Thr Thr Thr Pro Thr Pro Thr Gln Phe Leu
         85                  90                  95 tgc ccc aag aac gtg aca gat gag cag gag ggg ttc gcc gag ggc ttc      753
Cys Pro Lys Asn Val Thr Asp Glu Gln Glu Gly Phe Ala Glu Gly Phe
    100                 105                 110 gtg cgc gcc ctg gcc gaa ctg cac agc cag aac acg ctg ccc agc gtc      801
Val Arg Ala Leu Ala Glu Leu His Ser Gln Asn Thr Leu Pro Ser Val
115                 120                 125                 130 acg tcg gcg gcg cag ccg gtc aac ggg gca ggc atg gtg gct ccc gcg      849
Thr Ser Ala Ala Gln Pro Val Asn Gly Ala Gly Met Val Ala Pro Ala
                135                 140                 145 gta gcc tcg gtg gca ggg ggc agc ggc agc ggc ggc ttc agc gcc agc      897
Val Ala Ser Val Ala Gly Gly Ser Gly Ser Gly Gly Phe Ser Ala Ser
            150                 155                 160 ctg cac agc gag ccg ccg gtc tac gca aac ctc agc aac ttc aac cca      945
Leu His Ser Glu Pro Pro Val Tyr Ala Asn Leu Ser Asn Phe Asn Pro
        165                 170                 175 ggc gcg ctg agc agc ggc ggc ggg gcg ccc tcc tac ggc gcg gcc ggc      993
Gly Ala Leu Ser Ser Gly Gly Gly Ala Pro Ser Tyr Gly Ala Ala Gly
```

```
            180                 185                 190
ctg gcc ttt ccc gcg caa ccc cag cag cag cag ccg ccg cac cac        1041
Leu Ala Phe Pro Ala Gln Pro Gln Gln Gln Gln Pro Pro His His
195                 200                 205                 210 ctg ccc cag cag atg ccc gtg cag cac ccg cgg ctg cag gcc ctg aag    1089
Leu Pro Gln Gln Met Pro Val Gln His Pro Arg Leu Gln Ala Leu Lys
        215                 220                 225 gag gag cct cag aca gtg ccc gag atg ccc ggc gag aca ccg ccc ctg    1137
Glu Glu Pro Gln Thr Val Pro Glu Met Pro Gly Glu Thr Pro Pro Leu
230                 235                 240 tcc ccc atc gac atg gag tcc cag gag cgg atc aag gcg gag agg aag    1185
Ser Pro Ile Asp Met Glu Ser Gln Glu Arg Ile Lys Ala Glu Arg Lys
        245                 250                 255 cgc atg agg aac cgc atc gct gcc tcc aag tgc cga aaa agg aag ctg    1233
Arg Met Arg Asn Arg Ile Ala Ala Ser Lys Cys Arg Lys Arg Lys Leu
260                 265                 270 gag aga atc gcc cgg ctg gag gaa aaa gtg aaa acc ttg aaa gct cag    1281
Glu Arg Ile Ala Arg Leu Glu Glu Lys Val Lys Thr Leu Lys Ala Gln
275                 280                 285                 290 aac tcg gag ctg gcg tcc acg gcc aac atg ctc agg gaa cag gtg gca    1329
Asn Ser Glu Leu Ala Ser Thr Ala Asn Met Leu Arg Glu Gln Val Ala
            295                 300                 305 cag ctt aaa cag aaa gtc atg aac cac gtt aac agt ggg tgc caa ctc    1377
Gln Leu Lys Gln Lys Val Met Asn His Val Asn Ser Gly Cys Gln Leu
310                 315                 320 atg cta acg cag cag ttg caa aca ttt tgaagagaga ccgtcggggg          1424
Met Leu Thr Gln Gln Leu Gln Thr Phe
        325                 330 ctgaggggca acgaagaaaa aaataacac agagagacag acttgagaac ttgacaagtt   1484
gcgacggaga gaaaaaagaa gtgtccgaga actaaagcca agggtatcca agttggactg   1544
ggttcggtct gacggcgccc ccagtgtgca cgagtgggaa ggacctggtc gcgccctccc   1604
ttggcgtgga gccagggagc ggccgcctgc gggctgcccc gctttgcgga cgggctgtcc   1664
ccgcgcgaac ggaacgttgg actttcgtta acattgacca agaactgcat ggacctaaca   1724
ttcgatctca ttcagtatta aaggggcag ggggagggg ttacaaactg caatagagac   1784
tgtagattgc ttctgtagta ctccttaaga acacaaagcg gggggagggt tggggagggg   1844
cggcaggagg gaggtttgtg agagcgaggc tgagcctaca gatgaactct ttctggcctg   1904
ctttcgttaa ctgtgtatgt acatatatat attttttaat ttgattaaag ctgattactg   1964
tcaataaaca gcttcatgcc tttgtaagtt atttcttgtt tgtttgtttg ggatcctgcc   2024
cagtgttgtt tgtaaataag agatttggag cactctgagt ttaccatttg taataaagta   2084
tataattttt tt                                                       2096
```

<210> SEQ ID NO 10
<211> LENGTH: 331
<212> TYPE: PRT
<213> ORGANISM: Homo sapiens

<400> SEQUENCE: 10

Met Thr Ala Lys Met Glu Thr Thr Phe Tyr Asp Asp Ala Leu Asn Ala
1               5                   10                  15

Ser Phe Leu Pro Ser Glu Ser Gly Pro Tyr Gly Tyr Ser Asn Pro Lys
            20                  25                  30

Ile Leu Lys Gln Ser Met Thr Leu Asn Leu Ala Asp Pro Val Gly Ser
        35                  40                  45

-continued

```
Leu Lys Pro His Leu Arg Ala Lys Asn Ser Asp Leu Leu Thr Ser Pro
 50                  55                  60

Asp Val Gly Leu Leu Lys Leu Ala Ser Pro Glu Leu Glu Arg Leu Ile
 65                  70                  75                  80

Ile Gln Ser Ser Asn Gly His Ile Thr Thr Pro Thr Pro Thr Gln
                 85                  90                  95

Phe Leu Cys Pro Lys Asn Val Thr Asp Glu Gln Glu Gly Phe Ala Glu
                100                 105                 110

Gly Phe Val Arg Ala Leu Ala Glu Leu His Ser Gln Asn Thr Leu Pro
            115                 120                 125

Ser Val Thr Ser Ala Ala Gln Pro Val Asn Gly Ala Gly Met Val Ala
        130                 135                 140

Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Pro Pro
        195                 200                 205

His His Leu Pro Gln Gln Met Pro Val Gln His Pro Arg Leu Gln Ala
    210                 215                 220

Leu Lys Glu Glu Pro Gln Thr Val Pro Glu Met Pro Gly Glu Thr Pro
225                 230                 235                 240

Pro Leu Ser Pro Ile Asp Met Glu Ser Gln Glu Arg Ile Lys Ala Glu
                245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
        275                 280                 285

Ala Gln Asn Ser Glu Leu Ala Ser Thr Ala Asn Met Leu Arg Glu Gln
    290                 295                 300

Val Ala Gln Leu Lys Gln Lys Val Met Asn His Val Asn Ser Gly Cys
305                 310                 315                 320

Gln Leu Met Leu Thr Gln Gln Leu Gln Thr Phe
                325                 330

<210> SEQ ID NO 11
<211> LENGTH: 1418
<212> TYPE: DNA
<213> ORGANISM: Homo sapiens
<220> FEATURE:
<221> NAME/KEY: CDS
<222> LOCATION: (19)..(1170)
<223> OTHER INFORMATION:

<400> SEQUENCE: 11
cattaattgc ttgccatc atg agc aga agc aag cgt gac aac aat ttt tat      51
                    Met Ser Arg Ser Lys Arg Asp Asn Asn Phe Tyr
                      1               5                   10 agt gta gag att gga gat tct aca ttc aca gtc ctg aaa cga tat cag      99
Ser Val Glu Ile Gly Asp Ser Thr Phe Thr Val Leu Lys Arg Tyr Gln
             15                  20                  25 aat tta aaa cct ata ggc tca gga gct caa gga ata gta tgc gca gct     147
Asn Leu Lys Pro Ile Gly Ser Gly Ala Gln Gly Ile Val Cys Ala Ala
         30                  35                  40 tat gat gcc att ctt gaa aga aat gtt gca atc aag aag cta agc cga     195
```

-continued

```
Tyr Asp Ala Ile Leu Glu Arg Asn Val Ala Ile Lys Lys Leu Ser Arg
     45                  50                  55 cca ttt cag aat cag act cat gcc aag cgg gcc tac aga gag cta gtt        243
Pro Phe Gln Asn Gln Thr His Ala Lys Arg Ala Tyr Arg Glu Leu Val
 60                  65                  70                  75 ctt atg aaa tgt gtt aat cac aaa aat ata att ggc ctt ttg aat gtt        291
Leu Met Lys Cys Val Asn His Lys Asn Ile Ile Gly Leu Leu Asn Val
                     80                  85                  90 ttc aca cca cag aaa tcc cta gaa gaa ttt caa gat gtt tac ata gtc        339
Phe Thr Pro Gln Lys Ser Leu Glu Glu Phe Gln Asp Val Tyr Ile Val
                 95                 100                 105 atg gag ctc atg gat gca aat ctt tgc caa gtg att cag atg gag cta        387
Met Glu Leu Met Asp Ala Asn Leu Cys Gln Val Ile Gln Met Glu Leu
             110                 115                 120 gat cat gaa aga atg tcc tac ctt ctc tat cag atg ctg tgt gga atc        435
Asp His Glu Arg Met Ser Tyr Leu Leu Tyr Gln Met Leu Cys Gly Ile
         125                 130                 135 aag cac ctt cat tct gct gga att att cat cgg gac tta aag ccc agt        483
Lys His Leu His Ser Ala Gly Ile Ile His Arg Asp Leu Lys Pro Ser
140                 145                 150                 155 aat ata gta gta aaa tct gat tgc act ttg aag att ctt gac ttc ggt        531
Asn Ile Val Val Lys Ser Asp Cys Thr Leu Lys Ile Leu Asp Phe Gly
                 160                 165                 170 ctg gcc agg act gca gga acg agt ttt atg atg acg cct tat gta gtg        579
Leu Ala Arg Thr Ala Gly Thr Ser Phe Met Met Thr Pro Tyr Val Val
             175                 180                 185 act cgc tac tac aga gca ccc gag gtc atc ctt ggc atg ggc tac aag        627
Thr Arg Tyr Tyr Arg Ala Pro Glu Val Ile Leu Gly Met Gly Tyr Lys
         190                 195                 200 gaa aac gtg gat tta tgg tct gtg ggg tgc att atg gga gaa atg gtt        675
Glu Asn Val Asp Leu Trp Ser Val Gly Cys Ile Met Gly Glu Met Val
205                 210                 215 tgc cac aaa atc ctc ttt cca gga agg gac tat att gat cag tgg aat        723
Cys His Lys Ile Leu Phe Pro Gly Arg Asp Tyr Ile Asp Gln Trp Asn
220                 225                 230                 235 aaa gtt att gaa cag ctt gga aca cca tgt cct gaa ttc atg aag aaa        771
Lys Val Ile Glu Gln Leu Gly Thr Pro Cys Pro Glu Phe Met Lys Lys
                 240                 245                 250 ctg caa cca aca gta agg act tac gtt gaa aac aga cct aaa tat gct        819
Leu Gln Pro Thr Val Arg Thr Tyr Val Glu Asn Arg Pro Lys Tyr Ala
             255                 260                 265 gga tat agc ttt gag aaa ctc ttc cct gat gtc ctt ttc cca gct gac        867
Gly Tyr Ser Phe Glu Lys Leu Phe Pro Asp Val Leu Phe Pro Ala Asp
         270                 275                 280 tca gaa cac aac aaa ctt aaa gcc agt cag gca agg gat tta tta tcc        915
Ser Glu His Asn Lys Leu Lys Ala Ser Gln Ala Arg Asp Leu Leu Ser
285                 290                 295 aaa atg ctg gta ata gat gca tct aaa agg atc tct gta gat gaa gct        963
Lys Met Leu Val Ile Asp Ala Ser Lys Arg Ile Ser Val Asp Glu Ala
300                 305                 310                 315 ctc caa cac ccg tac atc aat gtc tgg tat gat cct tct gaa gca gaa       1011
Leu Gln His Pro Tyr Ile Asn Val Trp Tyr Asp Pro Ser Glu Ala Glu
                 320                 325                 330 gct cca cca cca aag atc cct gac aag cag tta gat gaa agg gaa cac       1059
Ala Pro Pro Pro Lys Ile Pro Asp Lys Gln Leu Asp Glu Arg Glu His
             335                 340                 345 aca ata gaa gag tgg aaa gaa ttg ata tat aag gaa gtt atg gac ttg       1107
Thr Ile Glu Glu Trp Lys Glu Leu Ile Tyr Lys Glu Val Met Asp Leu
         350                 355                 360
```

```
gag gag aga acc aag aat gga gtt ata cgg ggg cag ccc tct cct tta     1155
Glu Glu Arg Thr Lys Asn Gly Val Ile Arg Gly Gln Pro Ser Pro Leu
    365                 370                 375 gca cag gtg cag cag tgatcaatgg ctctcagcat ccatcatcat cgtcgtctgt    1210
Ala Gln Val Gln Gln
380 caatgatgtg tcttcaatgt caacagatcc gactttggcc tctgatacag acagcagtct   1270 agaagcagca gctgggcctc tgggctgctg tagatgacta cttgggccat cgggggggtgg  1330 gagggatggg gagtcggtta gtcattgata gaactacttt gaaaacaatt cagtggtctt   1390 atttttgggt gatttttcaa aaaatgta                                      1418

<210> SEQ ID NO 12
<211> LENGTH: 384
<212> TYPE: PRT
<213> ORGANISM: Homo sapiens

<400> SEQUENCE: 12

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205

Trp Ser Val Gly Cys Ile Met Gly Glu Met Val Cys His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
```

```
                290                 295                 300
Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
            355                 360                 365

Asn Gly Val Ile Arg Gly Gln Pro Ser Pro Leu Ala Gln Val Gln Gln
            370                 375                 380

<210> SEQ ID NO 13
<211> LENGTH: 17
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (1)..(17)
<223> OTHER INFORMATION: n is any nucleotide

<400> SEQUENCE: 13
caymgngayn tnaarcc                                                  17

<210> SEQ ID NO 14
<211> LENGTH: 22
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (11)..(11)
<223> OTHER INFORMATION: n is any nucleotide

<400> SEQUENCE: 14
gagagcccat nswccadatr tc                                            22

<210> SEQ ID NO 15
<211> LENGTH: 8
<212> TYPE: PRT
<213> ORGANISM: Artificial Sequence
<220> FEATURE:
<223> OTHER INFORMATION: Epitope tag

<400> SEQUENCE: 15

Asp Tyr Lys Asp Asp Asp Asp Lys
1               5

<210> SEQ ID NO 16
<211> LENGTH: 4
<212> TYPE: PRT
<213> ORGANISM: Artificial sequence
<220> FEATURE:
<223> OTHER INFORMATION: Consensus sequence motif
<220> FEATURE:
<221> NAME/KEY: MISC_FEATURE
<222> LOCATION: (1)..(1)
<223> OTHER INFORMATION: Xaa is Leu or Ala
<220> FEATURE:
<221> NAME/KEY: MISC_FEATURE
<222> LOCATION: (4)..(4)
<223> OTHER INFORMATION: Xaa is Asp or Glu

<400> SEQUENCE: 16
```

Xaa Ser Pro Xaa
1

<210> SEQ ID NO 17
<211> LENGTH: 1780
<212> TYPE: DNA
<213> ORGANISM: Homo sapiens
<220> FEATURE:
<221> NAME/KEY: CDS
<222> LOCATION: (59)..(1330)
<223> OTHER INFORMATION:

<400> SEQUENCE: 17

| | | |
|---|---|---|
| gggcgggcga gggatctgaa acttgcccac ccttcgggat attgcaggac gctgcatc | | 58 |
| atg agc gac agt aaa tgt gac agt cag ttt tat agt gtg caa gtg gca<br>Met Ser Asp Ser Lys Cys Asp Ser Gln Phe Tyr Ser Val Gln Val Ala<br>1               5                  10                  15 | | 106 |
| gac tca acc ttc act gtc cta aaa cgt tac cag cag ctg aaa cca att<br>Asp Ser Thr Phe Thr Val Leu Lys Arg Tyr Gln Gln Leu Lys Pro Ile<br>            20                  25                  30 | | 154 |
| ggc tct ggg gcc caa ggg att gtt tgt gct gca ttt gat aca gtt ctt<br>Gly Ser Gly Ala Gln Gly Ile Val Cys Ala Ala Phe Asp Thr Val Leu<br>        35                  40                  45 | | 202 |
| ggg ata agt gtt gca gtc aag aaa cta agc cgt cct ttt cag aac caa<br>Gly Ile Ser Val Ala Val Lys Lys Leu Ser Arg Pro Phe Gln Asn Gln<br>    50                  55                  60 | | 250 |
| act cat gca aag aga gct tat cgt gaa ctt gtc ctc tta aaa tgt gtc<br>Thr His Ala Lys Arg Ala Tyr Arg Glu Leu Val Leu Leu Lys Cys Val<br>65                  70                  75                  80 | | 298 |
| aat cat aaa aat ata att agt ttg tta aat gtg ttt aca cca caa aaa<br>Asn His Lys Asn Ile Ile Ser Leu Leu Asn Val Phe Thr Pro Gln Lys<br>                85                  90                  95 | | 346 |
| act cta gaa gaa ttt caa gat gtg tat ttg gtt atg gaa tta atg gat<br>Thr Leu Glu Glu Phe Gln Asp Val Tyr Leu Val Met Glu Leu Met Asp<br>            100                 105                 110 | | 394 |
| gct aac tta tgt cag gtt att cac atg gag ctg gat cat gaa aga atg<br>Ala Asn Leu Cys Gln Val Ile His Met Glu Leu Asp His Glu Arg Met<br>        115                 120                 125 | | 442 |
| tcc tac ctt ctt tac cag atg ctt tgt ggt att aaa cat ctg cat tca<br>Ser Tyr Leu Leu Tyr Gln Met Leu Cys Gly Ile Lys His Leu His Ser<br>    130                 135                 140 | | 490 |
| gct ggt ata att cat aga gat ttg aag cct agc aac att gtt gtg aaa<br>Ala Gly Ile Ile His Arg Asp Leu Lys Pro Ser Asn Ile Val Val Lys<br>145                 150                 155                 160 | | 538 |
| tca gac tgc acc ctg aag atc ctt gac ttt ggc ctg gcc cgg aca gcg<br>Ser Asp Cys Thr Leu Lys Ile Leu Asp Phe Gly Leu Ala Arg Thr Ala<br>                165                 170                 175 | | 586 |
| tgc act aac ttc atg atg acc cct tac gtg gtg aca cgg tac tac cgg<br>Cys Thr Asn Phe Met Met Thr Pro Tyr Val Val Thr Arg Tyr Tyr Arg<br>            180                 185                 190 | | 634 |
| gcg ccc gaa gtc atc ctg ggt atg ggc tac aaa gag aac gtt gat atc<br>Ala Pro Glu Val Ile Leu Gly Met Gly Tyr Lys Glu Asn Val Asp Ile<br>        195                 200                 205 | | 682 |
| tgg tca gtg ggt tgc atc atg gga gag ctg gtg aaa ggt tgt gtg ata<br>Trp Ser Val Gly Cys Ile Met Gly Glu Leu Val Lys Gly Cys Val Ile<br>    210                 215                 220 | | 730 |
| ttc caa ggc act gac cat att gat cag tgg aat aaa gtt att gag cag<br>Phe Gln Gly Thr Asp His Ile Asp Gln Trp Asn Lys Val Ile Glu Gln<br>225                 230                 235                 240 | | 778 |
| ctg gga aca cca tca gca gag ttc atg aag aaa ctt cag cca act gtg | | 826 |

```
Leu Gly Thr Pro Ser Ala Glu Phe Met Lys Lys Leu Gln Pro Thr Val
                245                 250                 255 agg aat tat gtc gaa aac aga cca aag tat cct gga atc aaa ttt gaa      874
Arg Asn Tyr Val Glu Asn Arg Pro Lys Tyr Pro Gly Ile Lys Phe Glu
            260                 265                 270 gaa ctc ttt cca gat tgg ata ttc cca tca gaa tct gag cga gac aaa      922
Glu Leu Phe Pro Asp Trp Ile Phe Pro Ser Glu Ser Glu Arg Asp Lys
        275                 280                 285 ata aaa aca agt caa gcc aga gat ctg tta tca aaa atg tta gtg att      970
Ile Lys Thr Ser Gln Ala Arg Asp Leu Leu Ser Lys Met Leu Val Ile
    290                 295                 300 gat cct gac aag cgg atc tct gta gac gaa gct ctg cgt cac cca tac     1018
Asp Pro Asp Lys Arg Ile Ser Val Asp Glu Ala Leu Arg His Pro Tyr
305                 310                 315                 320 atc act gtt tgg tat gac ccc gcc gaa gca gaa gcc cca cca cct caa     1066
Ile Thr Val Trp Tyr Asp Pro Ala Glu Ala Glu Ala Pro Pro Pro Gln
                325                 330                 335 att tat gat gcc cag ttg gaa gaa aga gaa cat gca att gaa gaa tgg     1114
Ile Tyr Asp Ala Gln Leu Glu Glu Arg Glu His Ala Ile Glu Glu Trp
            340                 345                 350 aaa gag cta att tac aaa gaa gtc atg gat tgg gaa gaa aga agc aag     1162
Lys Glu Leu Ile Tyr Lys Glu Val Met Asp Trp Glu Glu Arg Ser Lys
        355                 360                 365 aat ggt gtt gta aaa gat cag cct tca gat gca gca gta agt agc aac     1210
Asn Gly Val Val Lys Asp Gln Pro Ser Asp Ala Ala Val Ser Ser Asn
    370                 375                 380 gcc act cct tct cag tct tca tcg atc aat gac att tca tcc atg tcc     1258
Ala Thr Pro Ser Gln Ser Ser Ser Ile Asn Asp Ile Ser Ser Met Ser
385                 390                 395                 400 act gag cag acg ctg gcc tca gac aca gac agc agt ctt gat gcc tcg     1306
Thr Glu Gln Thr Leu Ala Ser Asp Thr Asp Ser Ser Leu Asp Ala Ser
                405                 410                 415 acg gga ccc ctt gaa ggc tgt cga tgataggtta gaaatagcaa acctgtcagc    1360
Thr Gly Pro Leu Glu Gly Cys Arg
                420 attgaaggaa ctctcacctc cgtgggcctg aaatgcttgg gagttgatgg aaccaaatag   1420 aaaaactcca tgttctgcat gtaagaaaca caatgcttg  ccctattcag acctgatagg   1480 attgcctgct tagatgataa aatgaggcag aatatgtctg aagaaaaaaa ttgcaagcca   1540 cacttctaga gattttgttc aagatcattt caggtgagca gttagagtag gtgaatttgt   1600 ttcaaattgt actagtgaca gtttctcatc atctgtaact gttgagatgt atgtgcatgt   1660 gaccacaaat gcttgcttgg acttgcccat ctagcacttt ggaaatcagt atttaaatgc   1720 caaataatct tccaggtagt gctgcttctg aagttatctc ttaatcctct taagtaattt   1780

<210> SEQ ID NO 18
<211> LENGTH: 424
<212> TYPE: PRT
<213> ORGANISM: Homo sapiens

<400> SEQUENCE: 18

Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
            20                  25                  30

Gly Ser Gly Ala Gln Gly Ile Val Cys Ala Ala Phe Asp Thr Val Leu
        35                  40                  45

Gly Ile Ser Val Ala Val Lys Lys Leu Ser Arg Pro Phe Gln Asn Gln
```

-continued

```
                 50                  55                  60
Thr His Ala Lys Arg Ala Tyr Arg Glu Leu Val Leu Leu Lys Cys Val
 65                  70                  75                  80

Asn His Lys Asn Ile Ile Ser Leu Leu Asn Val Phe Thr Pro Gln Lys
                     85                  90                  95

Thr Leu Glu Glu Phe Gln Asp Val Tyr Leu Val Met Glu Leu Met Asp
                100                 105                 110

Ala Asn Leu Cys Gln Val Ile His Met Glu Leu Asp His Glu Arg Met
            115                 120                 125

Ser Tyr Leu Leu Tyr Gln Met Leu Cys Gly Ile Lys His Leu His Ser
        130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Leu Val Lys Gly Cys Val Ile
210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
            260                 265                 270

Glu Leu Phe Pro Asp Trp Ile Phe Pro Ser Glu Ser Glu Arg Asp Lys
        275                 280                 285

Ile Lys Thr Ser Gln Ala Arg Asp Leu Leu Ser Lys Met Leu Val Ile
290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
            340                 345                 350

Lys Glu Leu Ile Tyr Lys Glu Val Met Asp Trp Glu Glu Arg Ser Lys
        355                 360                 365

Asn Gly Val Val Lys Asp Gln Pro Ser Asp Ala Ala Val Ser Ser Asn
    370                 375                 380

Ala Thr Pro Ser Gln Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
                405                 410                 415

Thr Gly Pro Leu Glu Gly Cys Arg
            420
```

```
<210> SEQ ID NO 19
<211> LENGTH: 227
<212> TYPE: PRT
<213> ORGANISM: Yeast HOG1

<400> SEQUENCE: 19
```

```
Met Thr Thr Asn Glu Glu Ile Arg Thr Gln Phe Gly Thr Val Glu Ile
1               5                   10                  15

Thr Asn Asn Asp Asn Pro Val Met Phe Leu Ser Thr Thr Leu Thr Ser
            20                  25                  30

Gln Pro Ile Met Lys Ser Thr Ala Val Leu Thr Lys Leu His Leu Arg
        35                  40                  45

Glu Leu Cys Gln Asp Ile Ser Pro Leu Glu Ile Phe Thr Gln Gly Thr
    50                  55                  60

Asp His Arg Leu Leu Thr Arg Pro Glu Lys Gln Phe Val Gln Phe Ile
65                  70                  75                  80

Arg Leu Tyr Val Val Leu Ile Asn Glu Asn Asp Cys Ile Gln Asp Pro
                85                  90                  95

Gln Gly Ser Ile Met Thr Trp Gln Lys Asp Val Glu Ile Ala Phe Ala
            100                 105                 110

Ile Glu Gly Pro Lys His Val His Phe Ser Ile Ile Thr Asp Leu Ser
        115                 120                 125

Lys Asp Val Ile Asn Thr Ile Cys Ser Glu Asn Thr Leu Lys Phe Thr
130                 135                 140

Ser Leu His Arg Asp Pro Ile Pro Ser Glu Arg Lys Thr Val Glu Pro
145                 150                 155                 160

Asp Val Glu Phe Pro Lys Thr Ala Ala Asp Ala Ser Ala Pro Tyr His
                165                 170                 175

Thr Asp Pro Val Ala Ala Lys Phe Trp His Phe Asn Asp Ala Asp Leu
            180                 185                 190

Pro Val Asp Thr Arg Val Met Met Ser Ile Leu Phe His Lys Ile Gly
        195                 200                 205

Gly Ser Asp Gly Gln Ile Asp Ile Ser Ala Thr Phe Asp Asp Gln Val
    210                 215                 220

Ala Ala Ala
225

<210> SEQ ID NO 20
<211> LENGTH: 243
<212> TYPE: PRT
<213> ORGANISM: Yeast MPK1

<400> SEQUENCE: 20

Met Ala Asp Lys Ile Glu Arg His Thr Phe Lys Val Phe Asn Gln Asp
1               5                   10                  15

Ser Asp Phe Leu Ile Glu His Tyr Ser Arg Phe Ala Glu Ala Glu Asp
            20                  25                  30

Thr Thr Thr Asn Val Ser Lys Thr Leu Leu Cys Ser Leu Lys Leu Arg
        35                  40                  45

His Phe Arg Gly Thr Cys Tyr Asp Met Asp Ile Val Phe Tyr Pro Asp
    50                  55                  60

Gly Ser Ile Asn Gly Leu Leu Tyr Glu Glu Cys Asp Met His Ile Lys
65                  70                  75                  80

Ser Gly Gln Pro Thr Asp Ala His Tyr Gln Ser Phe Thr Ile Leu Tyr
            85                  90                  95

Ile Asp Val Leu Gly Leu Leu Asn Ala Gln Cys Gly Tyr Ser Glu Asn
            100                 105                 110

Pro Val Glu Asn Ser Gln Phe Leu Glu Ala Trp Ile Met Ser Tyr Gln
        115                 120                 125

Thr Lys Ala Ile Val Ala Leu Ala Phe Leu Gly Gly Pro Ile Lys Lys
130                 135                 140
```

Val Asn Leu Asn Gln Ile Leu Gln Val Asp Glu Thr Leu Arg Arg Ile
145                 150                 155                 160

Gly Ser Lys Asn Gln Asp Ile His Gln Leu Gly Phe Ile Pro Lys Val
                165                 170                 175

Pro Val Asn Tyr Asn Ala Asn Leu Glu Gln Ala Phe Pro Gln Thr Glu
            180                 185                 190

Leu Ser Ile His Ala Asp Pro Val Cys Ser Glu Lys Phe Glu Phe Ser
        195                 200                 205

Phe Glu Ser Val Asn Asp Met Asp Leu Gln Met Val Ile Gln Gln Phe
    210                 215                 220

Arg Leu Phe Val Arg Gln Pro Leu Leu Glu Glu Arg Gln Leu Gln Leu
225                 230                 235                 240

Gln Gln Gln

<210> SEQ ID NO 21
<211> LENGTH: 230
<212> TYPE: PRT
<213> ORGANISM: Yeast FUS3

<400> SEQUENCE: 21

Met Ala Arg Thr Ile Asp Ile Pro Ser Gln Lys Leu Val Asp Leu Glu
1               5                   10                  15

Tyr Thr Ser Ile His Lys Pro Ser Gly Ile Lys Ile Gln Ser Lys Lys
            20                  25                  30

Leu Phe Val Thr Thr Ile Ile Lys Leu Arg Tyr Phe His Glu Glu Ser
        35                  40                  45

Ile Asp Lys Val Arg Pro Val Ile Asp Lys Leu Asn Ala Leu Glu Glu
    50                  55                  60

Thr Asp Gln Lys Asn Asn Gln Asn Ser Gly Phe Ser Thr Ser Asp Asp
65                  70                  75                  80

His Val Gln Phe Thr Ile Arg Ala Leu Ser Ile Gln Val Ile Ile Leu
                85                  90                  95

Leu Leu Asn Asn Asp Val Cys Cys Leu Ala Ser Ser Asp Ser Arg Glu
            100                 105                 110

Thr Leu Val Gly Phe Glu Ala Trp Ile Met Thr Phe Gln Glu Thr Thr
        115                 120                 125

Ala Met Ile Cys Leu Ala Ser Gly Pro His His Leu Trp Leu Ile Leu
130                 135                 140

Val Ser Phe Glu Asp Asn Gln Ile Lys Ser Lys Arg Ala Lys Glu Ile
145                 150                 155                 160

Ala Leu Met Arg Pro Pro Leu Pro Trp Thr Val Trp Ser Lys Thr Asp
                165                 170                 175

Leu Asn Pro Asp Met Ile Asp Gln Phe Asn Pro Asp Ala Ala Arg Leu
            180                 185                 190

Ala Met Tyr His Asp Pro Tyr Leu Asn Leu Asp Glu Phe Trp Lys Leu
        195                 200                 205

Asp Asn Lys Ile Met Arg Pro Glu Glu Glu Val Pro Met Leu Asp Met
    210                 215                 220

Leu Asp Leu Lys Thr Met
225                 230

<210> SEQ ID NO 22
<211> LENGTH: 221
<212> TYPE: PRT
<213> ORGANISM: Yeast KSS1

```
<400> SEQUENCE: 22

Met Pro Lys Arg Ile Val Tyr Asn Ile Ser Ser Asp Phe Leu Lys Ser
1               5                   10                  15

Leu Leu Glu Tyr Val Ser Thr His Lys Pro Thr Gly Glu Ile Ile Glu
            20                  25                  30

Asp Lys Pro Leu Phe Leu Thr Leu Ile Lys Ile Leu His Phe Lys Glu
        35                  40                  45

Thr Ile Phe Ile Gln Arg Pro Asp Phe Asn Asn Glu Ile Gln Gln Thr
    50                  55                  60

Asp His Arg Ser Thr Gln Met Ser Asp His Ile Gln Phe Ile Thr
65                  70                  75                  80

Arg Ala Val Val Gly Ser Asn Val Ile Leu Ile Asn Asn Asp Val
                85                  90                  95

Cys Ile Ile Asp Glu Ala Ala Asp Asn Ser Glu Pro Thr Gly Gln Gln
            100                 105                 110

Ser Gly Glu Ala Trp Met Thr Ser Ala Lys Ser Arg Ala Met Val Cys
        115                 120                 125

Leu Ala Leu Phe Leu Arg Arg Pro Ile Arg His Leu Leu Ile Phe
130                 135                 140

Gly Ile Ile His Ser Asp Asn Asp Leu Arg Cys Ile Glu Ser Arg Ala
145                 150                 155                 160

Glu Ile Lys Ser Leu Met Pro Ala Ala Pro Leu Met Arg Val Asn Pro
                165                 170                 175

Lys Gly Ile Gln Arg Phe Pro Ala Thr Ala Lys Glu Leu Gln Thr Tyr
            180                 185                 190

His Asn Asp Pro Gly Glu Pro Ser Phe Glu Phe Asp His His Lys
        195                 200                 205

Glu Ala Leu Thr Lys Asp Leu Lys Trp Asn Ile Phe Ser
    210                 215                 220

<210> SEQ ID NO 23
<211> LENGTH: 242
<212> TYPE: PRT
<213> ORGANISM: Yeast ERK1

<400> SEQUENCE: 23

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
            20                  25                  30

Gly Gln Pro Asp Gly Pro Thr Gln Gln Tyr Glu Tyr Met Ser Ser His
        35                  40                  45

Val Arg Lys Thr Arg Ile Glu His Tyr Cys Gln Thr Leu Ile Gln Ile
    50                  55                  60

Leu Leu Arg Phe Arg Glu Val Ile Arg Asp Ile Leu Arg Ala Ser Thr
65                  70                  75                  80

Ala Met Arg Gln Asp Glu Thr Asp Tyr Lys Leu Leu Lys Ser Gln Gln
                85                  90                  95

Ser Asn Asp His Ile Cys Phe Ile Arg Leu Tyr Ile Asn Val Leu Leu
            100                 105                 110

Leu Ile Asn Thr Thr Asp Cys Ile Asp Pro Glu His Asp His Thr Gly
        115                 120                 125

Phe Leu Glu Ala Trp Ile Met Asn Ser Lys Thr Lys Ser Ile Ile Leu
    130                 135                 140
```

```
Ala Leu Ser Asn Arg Pro Ile Lys His Leu His Ile Leu Gly Ile
145                 150                 155                 160

Ser Ser Gln Glu Asp Leu Asn Cys Ile Ile Asn Met Lys Ala Asn Leu
            165                 170                 175

Gln Ser Leu Ser Lys Thr Lys Val Ala Trp Ala Lys Ser Asp Lys Leu
            180                 185                 190

Asp Arg Thr Phe Asn Pro Asn Thr Glu Ala Leu Glu Gln Tyr Thr Asp
            195                 200                 205

Pro Val Ala Glu Glu Pro Phe Thr Phe Ala Met Glu Leu Asp Asp Leu
            210                 215                 220

Pro Lys Arg Leu Phe Gln Thr Ala Arg Phe Gln Pro Gly Val Leu Glu
225                 230                 235                 240

Ala Pro

<210> SEQ ID NO 24
<211> LENGTH: 220
<212> TYPE: PRT
<213> ORGANISM: Yeast ERK2

<400> SEQUENCE: 24

Met Ala Ala Ala Ala Ala Gly Ala Gly Pro Glu Met Val Arg Gly
1               5                   10                  15

Gln Val Asp Gly Pro Thr Ser Tyr Glu Tyr Met Ser Asn Val Asn Lys
            20                  25                  30

Val Arg Ile Glu His Tyr Cys Gln Thr Leu Ile Lys Ile Leu Leu Arg
            35                  40                  45

Phe Arg Glu Ile Asn Asp Ile Ile Gln Ala Pro Thr Ile Gln Met Lys
50                  55                  60

Gln Asp Glu Thr Asp Tyr Lys Leu Leu Lys Thr Gln His Ser Asn Asp
65                  70                  75                  80

His Ile Cys Phe Ile Arg Leu Tyr Ile Asn Val Leu Leu Leu Leu Asn
                85                  90                  95

Thr Thr Asp Cys Val Asp Pro Asp His Asp His Thr Gly Phe Leu Glu
                100                 105                 110

Ala Trp Ile Met Asn Ser Lys Thr Lys Ser Ile Ile Leu Ala Leu Ser
            115                 120                 125

Asn Arg Pro Ile Lys His Leu Leu His Ile Leu Gly Ile Ser Ser Gln
130                 135                 140

Glu Asp Leu Asn Cys Ile Ile Asn Leu Lys Ala Asn Leu Leu Ser Leu
145                 150                 155                 160

His Lys Asn Lys Val Pro Trp Asn Arg Asn Ala Asp Lys Leu Asp Thr
                165                 170                 175

Phe Asn Pro His Glu Glu Gln Ala Leu Glu Gln Tyr Asp Pro Ala Glu
            180                 185                 190

Ala Pro Phe Lys Phe Asp Met Glu Leu Asp Asp Leu Pro Lys Lys Leu
            195                 200                 205

Phe Glu Thr Ala Arg Phe Gln Pro Gly Tyr Arg Ser
            210                 215                 220

<210> SEQ ID NO 25
<211> LENGTH: 81
<212> TYPE: PRT
<213> ORGANISM: Artificial sequence
<220> FEATURE:
<223> OTHER INFORMATION: Consensus sequence
```

<400> SEQUENCE: 25

```
Gly Gly Ala Gly Val Ala Val Ala Ile Lys Lys Phe Arg Arg Glu His
1               5                   10                  15
Asn Tyr Leu Leu Tyr Gln Leu Lys His His Arg Asp Lys Pro Asn Cys
            20                  25                  30
Leu Lys Asp Phe Gly Leu Ala Arg Thr Tyr Val Thr Arg Tyr Arg Ala
        35                  40                  45
Pro Glu Leu Tyr Asp Trp Ser Gly Cys Ile Glu Phe Gly Gln Gly Pro
    50                  55                  60
Asp Leu Leu Met Leu Lys Arg Ile Ala Leu His Pro Tyr Asp Pro Glu
65                  70                  75                  80
Glu
```